(12) United States Patent
Drnevich et al.

(10) Patent No.: US 9,696,292 B2
(45) Date of Patent: Jul. 4, 2017

(54) TIME DOMAIN REFLECTOMETRY FOR CHARACTERIZING SOILS

(71) Applicant: Purdue Research Foundation, West Lafayette, IN (US)

(72) Inventors: Vincent P. Drnevich, West Lafayette, IN (US); Sochan Jung, Houston, TX (US); Majdi Abou Najm, Bchamoun (LB)

(73) Assignee: Purdue Research Foundation, West Lafayette, IN (US)

( * ) Notice: Subject to any disclaimer, the term of this patent is extended or adjusted under 35 U.S.C. 154(b) by 1092 days.

(21) Appl. No.: 13/662,933

(22) Filed: Oct. 29, 2012

(65) Prior Publication Data

US 2013/0110398 A1    May 2, 2013

Related U.S. Application Data

(60) Provisional application No. 61/553,141, filed on Oct. 28, 2011.

(51) Int. Cl.
*G01N 33/24* (2006.01)

(52) U.S. Cl.
CPC .................. *G01N 33/246* (2013.01)

(58) Field of Classification Search
USPC ....................................... 702/2, 11
See application file for complete search history.

(56) References Cited

U.S. PATENT DOCUMENTS

| | | | |
|---|---|---|---|
| 5,136,249 A | 8/1992 | White et al. | |
| 5,646,537 A | 7/1997 | Skaling et al. | |
| 5,801,537 A | 9/1998 | Siddiqui et al. | |
| 5,933,015 A | 8/1999 | Siddiqui et al. | |
| 6,215,317 B1 | 4/2001 | Siddiqui et al. | |
| 7,040,145 B2 | 5/2006 | Drnevich et al. | |
| 2004/0201385 A1* | 10/2004 | Drnevich ............. | G01N 33/246 324/643 |

OTHER PUBLICATIONS

ASTM; Standard test method for water content and density of soil in place by time domain reflectometry (TDR). D6780-05, 2005; West Conshohocken, PA.
Stogryn, A.; Equations for calculating the dielectric constant of saline water. Microwave Theory 357 Tech., IEEE Transactions on, MIT-19; 1971; 733-736.
Weast, R.C.; CRC handbook of chemistry and physics, 67th ed. 1986; CRC Press, Boca Raton, FL.

* cited by examiner

*Primary Examiner* — Mohamed Charioui
(74) *Attorney, Agent, or Firm* — John V. Daniluck; Brian W. Chellgren; Bingham Greenebaum Doll LLP

(57) ABSTRACT

New time-domain response system calibration techniques are described for determining dry density and water content of soil based on electromagnetic wave propagation through it. For example, one disclosed technique use the ratio between $V_1$, the voltage difference between the peak and trough of the response signal, and $V_f$, the long-term (i.e., steady-state) response of the system to the input pulse. These values are measurable, even for highly conductive soils, and calibration done in a laboratory can be applied to measurements taken in an uncontrolled field environment.

25 Claims, 47 Drawing Sheets

TIME DOMAIN REFLECTOMETRY FOR CHARACTERIZING SOILS

CROSS REFERENCE TO RELATED APPLICATION

This application claims the benefit of priority to U.S. Provisional Patent Application Ser. No. 61/553,141, filed on Oct. 28, 2011, entitled "TDR FOR WATER CONTENT AND DRY DENSITY OF SOILS," incorporated herein by reference.

FIELD OF THE INVENTION

The present invention relates to analysis of soil. More specifically, the present invention relates to analysis of the Time Domain Reflectometry (TDR) of a soil sample to estimate water content and dry density of the sample.

BACKGROUND OF THE INVENTION

TDR was developed assuming one-dimensional electromagnetic wave propagation in dielectric materials. In one embodiment, it is applied to detect the breaks in cables of coaxial transmission lines, telecommunications, and more recently applied to TV and computer networks. As one example, a voltage is applied to an end of a cable and a discontinuity in the cable causes a voltage reflection. By recording the reflection time, the distance to the discontinuity can be calculated if the apparent dielectric properties of the cable are known. FIG. 3-1 shows a schematic description of TDR system as a multi-section transmission line. It includes a TDR apparatus with step voltage generator and data acquisition system, a coaxial cable, and a measurement probe (non-insulated) embedded in a soil. The measurement probe includes a probe head and a plurality of spaced apart TDR probes or "spikes." The apparent dielectric constant, $K_a$, can be determined by the travel time analysis of the TDR waveform for a known probe or spike length.

The current used Purdue One-step TDR method provides a procedure for measuring the water content w and dry density $\rho_d$ of soil in the field, using the TDR device, with use of soil-specific calibration coefficients obtained from laboratory TDR tests. The method utilizes $K_a$ and the bulk electrical conductivity of soil, $EC_b$, for predicting w and $\rho_d$, where $EC_b$ for a given probe configuration can be obtained from measuring the waveform reflections and characteristic impedance of a cable. The Purdue One-step TDR method can be used with a range of water contents, especially if assisted with modeling between density-normalized $EC_b$ and w. However, the method may be sensitive to variation in compaction energies.

SUMMARY OF THE INVENTION

One aspect of this study was to develop a reliable method for predicting the soil density and water content. The Purdue One-step TDR method was revisited and the Siddiqui-Drnevich equation (Eq. (1-1)) was confirmed a valuable calibration relationship. The first voltage drop, $V_1$, was introduced along with the new calibration equation relating $$\frac{V_1}{V_f} \frac{\rho_w}{\rho_d}$$

to $K_a$. The new method was validated at a wide range of soil water contents and soil textures ranging from coarse-grained soils to high plastic clays. The method proved independent of soil compaction energy level, as it produced, using calibration coefficients from standard compaction tests, predictions at reduced, standard, and modified compaction levels. It also produced predictions over a wide range of temperatures (after applying temperature correction factors for $K_a$ and $V_1/V_f$), and under different pore fluid properties and probe configurations.

Overall, the method presents an improvement to the existing Purdue One-step TDR method (ASTM D6780 (ASTM 2005)). Calibration coefficients determined from the laboratory were validated in engineered and non-engineered field sites, in an attempt to show that the new method can be extended to in-situ field measurements of water content and dry density. Thus, the new method is proposed as a new tool for estimating water content and density for the field sites commonly used in geotechnical and other geo-environmental applications.

The objective of this application is to present a new method, independent of compaction energy, for predicting w and $\aleph_d$. This method introduces a new TDR-measured parameter, $V_1$, termed "first voltage drop". $V_1$ is utilized along with the TDR-measured final voltage, $V_f$. Investigations showed that a unique and soil-specific relationship exists between the ratio $$\frac{V_1}{V_f} \frac{\rho_w}{\rho_d}$$

and $K_a$ which is independent of compaction energy.

In some embodiments, a method for measuring a property of soil comprises providing a plurality of spikes adapted to be driven into the soil; driving the plurality of spikes into the soil in spaced relationship; applying to the plurality of spikes an electrical signal suitable for time domain reflectometry; analyzing a reflected signal using time domain reflectometry to measure a voltage parameter; calculating dry density $\rho_d$ of the soil using a predetermined relationship between the voltage parameter and $\rho_d$; and calculating gravimetric water content w of the soil using a predetermined relationship between $\rho_d$, and w.

In some embodiments, a method for measuring a property of soil comprises providing a plurality of spikes adapted to be driven into the soil; driving the plurality of spikes into the soil in spaced relationship; applying to the plurality of spikes an electrical signal suitable for time domain reflectometry; analyzing a reflected signal using time domain reflectometry to determine electrical parameters; adjusting the electrical parameters using predetermined temperature compensation functions; and calculating dry density $\rho_d$ of the soil using a predetermined relationship between the electrical parameters and $\rho_d$.

Disclosed herein is an apparatus for measuring a property of soil that, in some embodiments, comprises a plurality of spikes adapted to be driven into the soil; means for applying to the plurality of spikes an electrical signal suitable for time domain reflectometry; means for analyzing a reflected signal using time domain reflectometry; means for calculating dry density ρd of the soil using a predetermined relationship between V1 and ρd; and means for calculating gravimetric water content w of the soil using a predetermined relationship between ρd, and w. In some embodiments, the means for applying the electrical signal is a TDR apparatus. In some embodiments, the means for analyzing the reflected signal and the means for calculating water content and dry density are a computer.

It will be appreciated that the various apparatus and methods described in this summary section, as well as elsewhere in this application, can be expressed as a large number of different combinations and subcombinations. All such useful, novel, and inventive combinations and subcombinations are contemplated herein, it being recognized that the explicit expression of each of these combinations is unnecessary.

BRIEF DESCRIPTION OF THE DRAWINGS

Some of the figures shown herein may include dimensions. Further, some of the figures shown herein may have been created from scaled drawings or from photographs that are scalable. It is understood that such dimensions, or the relative scaling within a figure, are by way of example, and not to be construed as limiting.

FIG. 1-2 is a set of graphs comparing dry density to water contents for three compaction values, and TDR waveforms at particular water content levels: (a) Modified (MC), Standard (SC) and Reduced Compaction (RC) tests data, and (b), (c) graphs of TDR waveforms at water contents of 10% and 20%, respectively, for ASTM CH soil.

FIG. 1-3($a$) is a cross-sectional schematic diagram of a probe used for taking TDR measurements in a compaction mold. FIGS. 1-3($b$-$c$) are graphs of TDR waveforms for ASTM CH soil (SC) with a water content of 20% and for deionized (DI) water, respectively.

FIG. 1-4 is a voltage and density normalization plot against $K_a$. Voltage and density normalization are plotted against $K_a$ using Modified (MC), Standard (SC) and Reduced Compaction (RC) test data for ASTM CH soils.

FIG. 1-5 is a graph comparing dry density by TDR with direct measurement of moist density and oven-drying water content. Tests were performed for ASTM CH soils with RC, SC, and MC levels. TDR data points generated using the Purdue One-step method (ASTM D6780-05) are denoted by the symbol "X."

FIG. 1-6 is a graph comparing water content determined by TDR with water content determined by direct measurement using the oven-drying method. Tests were performed for ASTM CH soils with RC, SC, and MC levels. TDR data points generated using the Purdue One-step method (ASTM D6780-05) are denoted by the symbol "X."

FIG. 1-7 is a graph comparing compaction curves by TDR and by direct measurements with oven-drying method for ASTM CH soils.

FIG. 1-8 is a graph illustrating determination of a first reflection point by curve fitting. The symbol "+" data points indicate measured x and y coordinates on a TDR waveform. The curved line indicates the $2^{nd}$ order polynomial calculated from the data points.

FIG. 1-9 is a graph illustrating determination of a second reflection point by curve fitting. The symbol "+" data points indicate measured x and y coordinates on a TDR waveform. The curved line indicates a compound arc tangent function given as Equation (1-12), calculated from the data points.

FIG. 1-10 is a flowchart illustrating a method for calculating dry density and water content of soil.

FIG. 2-1 is a set of graphs. FIGS. 2-1($a$) and ($b$) illustrate calibration equations ((a) Eq. (1-1), (b) Eq. (1-9)) from compaction (SC, RC, MC) tests for fine-grained (ASTM ML) and coarse-grained (ASTM SP) soils. FIGS. 2-1($c$) and ($d$) depict comparisons of compaction curves by TDR with dry density by direct measurements of total density and oven-drying water content, plotting with data from (2-1($c$)) ASTM ML and (2-1($d$)) coarse-grained (ASTM SP) soils. "ZAV" denotes the zero air voids line at 100% degree of saturation.

FIG. 2-2 is a set of graphs illustrating comparisons of (a) water content determined by TDR with water content determined by oven drying and (b) dry density determined by TDR with dry density from direct measurements of total density and oven-drying water content for compaction (SC, RC, and MC) tests on ASTM Reference Soils and M soils (Note: The results of water content are plotted with the percentage point of 1:1 line, while the results of dry density are plotted with the percentage of 1:1 line).

FIG. 2-3 is an image showing cracks adjacent to the center rod in a cylindrical mold probe for ASTM CH soils at 15% of water content.

FIG. 2-4 is a set of graphs illustrating comparisons of (a) water content and (b) dry density by TDR (existing Purdue One-step method vs. new method) with direct measurements of total density and oven-drying water content in lab testing for ASTM Reference Soils and M soils, plotting with data from standard compaction (SC), reduced compaction (RC), and modified compaction (MC) tests (Note: The results of water content (2-4($a$)) are plotted with the percentage point of 1:1 line, while the results of dry density (2-4($b$)) are plotted with the percentage of 1:1 line).

FIG. 3-1 is a schematic diagram of one embodiment of an apparatus for measuring a property of soil.

FIG. 3-2 is a graph of a TDR waveform for ASTM CH soil with 20% of water content.

FIG. 3-3 is a set of graphs illustrating comparisons of (a) $K_a$ and (b) temperature correction factor for $K_a$ of water determined by Eq. (3-3) with earlier results (Weast (1986)).

FIG. 3-4 is a set of graphs illustrating temperature correction factor for $K_a$ on (a) cohesionless soils (CON, OTT, KLS) and (b) cohesive soils (CRO, KAO, ILL, MSL, BSL, RYO).

FIG. 3-5 is a set of graphs illustrating temperature correction factor for $V_1$ on (a) cohesionless soils (CON, OTT) and (b) cohesive soils (CRO, KAO, ILL).

FIG. 3-6 is a set of graphs illustrating temperature correction factor for $EC_b$ on soils. (a) individual soil types, (b) dry soils versus soils with medium to high water contents. FIG. 3-6($b$) also compares temperature correction factor for $EC_b$ on soils with earlier results (Stogryn (1971)).

FIG. 3-7 is a set of graphs illustrating temperature correction factor for $V_1/V_f$ as a function of temperature and $V_f/V_{in}$ for (a) cohesionless soil, and (b) cohesive soil.

FIG. 3-8 is a set of graphs illustrating temperature correction factors for $K_a$ on (a), (b), (c) cohesionless soils CON, OTT, and KLS, and (d), (e), (f) cohesive soils CRO, MSL, and BSL and RYO. Included are comparisons between measured data from TDR tests and calculated data from dielectric mixing models.

FIG. 3-9 is a set of graphs of $V_1/V_f$ versus $K_a$ for (a) multiple soil types, (b) soils delineated as cohesionless and cohesive.

FIG. 3-10 is a set of graphs of data from TDR tests on CRO soil for determining TDR parameters for Eq. (1-9): (a)

Figure 1:
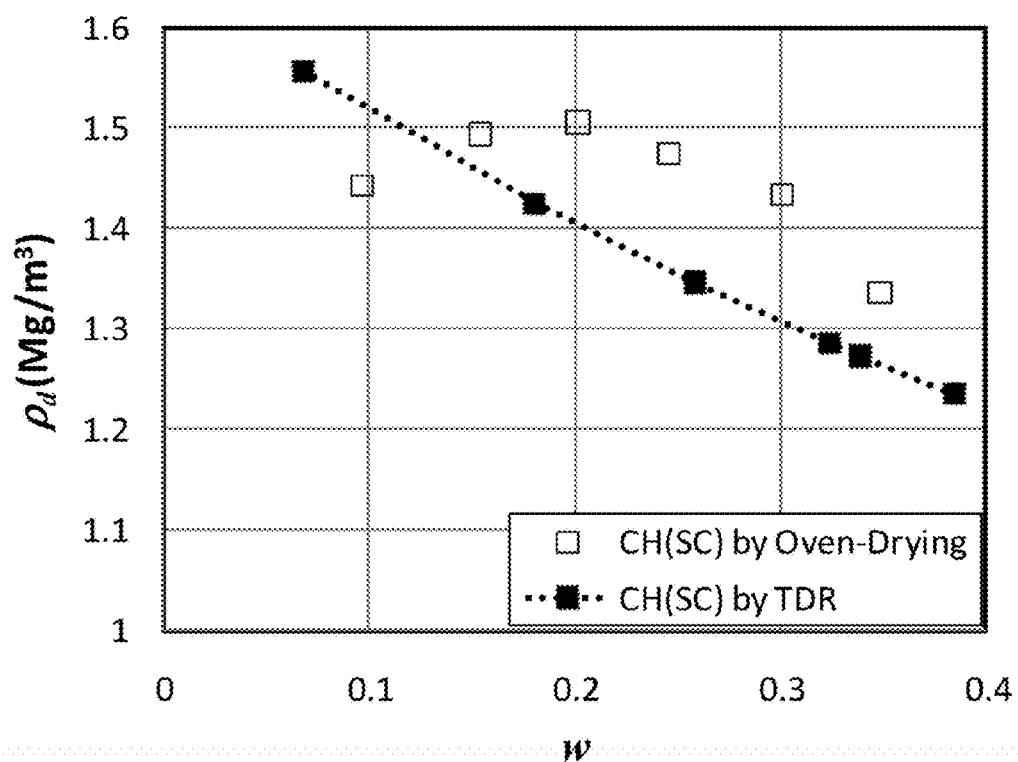
FIG. 1-1 is a graph comparing TDR-predicted water content and dry density using the Purdue One-step method to that obtained from direct measurements. Comparison of TDR-predicted water content and dry density (solid squares) relationship to that obtained from direct measurements for ASTM CH soils (at standard compaction "SC").

data as measured at temperatures at 4° C., 10° C., 20° C., 30° C., and 40° C., (b) data adjusted to 20° C. by use of Eqs. (3-6) and (3-17).

FIG. 3-11 is a set of graphs comparing (a) water content by TDR with oven-drying water content and (b) dry density by TDR with dry density from direct measurements of total density and oven-drying water content in testing for CRO, CON, and OTT soils (Note: The results of water content (3-11(a)) are plotted with the percentage point of 1:1 line, while the results of dry density (3-11(b)) are plotted with the percentage of 1:1 line).

DESCRIPTION

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. At least one embodiment of the present invention will be described and shown, and this application may show and/or describe other embodiments of the present invention. It is understood that any reference to "the invention" is a reference to an embodiment of a family of inventions, with no single embodiment including an apparatus, process, or composition that should be included in all embodiments, unless otherwise stated. Further, although there may be discussion with regards to "advantages" provided by some embodiments of the present invention, it is understood that yet other embodiments may not include those same advantages, or may include yet different advantages. Any advantages described herein are not to be construed as limiting to any of the claims.

The use of an N-series prefix for an element number (NXX.XX) refers to an element that is the same as the non-prefixed element (XX.XX) except as shown and described thereafter The usage of words indicating preference, such as "preferably," refers to features and aspects that are present in at least one embodiment, but which are optional for some embodiments. As an example, an element 1020.1 would be the same as element 20.1, except for those different features of element 1020.1 shown and described. Further, common elements and common features of related elements are drawn in the same manner in different figures, and/or use the same symbology in different figures. As such, it is not necessary to describe the features of 1020.1 and 20.1 that are the same, since these common features are apparent to a person of ordinary skill in the related field of technology. This description convention also applies to the use of prime ('), double prime ("), and triple prime ("') suffixed element numbers. Therefore, it is not necessary to describe the features of 20.1, 20.1', 20.1", and 20.1'" that are the same, since these common features are apparent to persons of ordinary skill in the related field of technology.

Although various specific quantities (spatial dimensions, temperatures, pressures, times, force, resistance, current, voltage, concentrations, wavelengths, frequencies, heat transfer coefficients, dimensionless parameters, etc.) may be stated herein, such specific quantities are presented as examples only, and further, unless otherwise noted, are approximate values, and should be considered as if the word "about" prefaced each quantity. Further, with discussion pertaining to a specific composition of matter, that description is by example only, and does not limit the applicability of other species of that composition, nor does it limit the applicability of other compositions unrelated to the cited composition.

What will be shown and described herein, along with various embodiments of the present invention, is discussion of one or more tests that were performed. It is understood that such examples are by way of examples only, and are not to be construed as being limitations on any embodiment of the present invention. It is understood that embodiments of the present invention are not necessarily limited to or described by the mathematical analysis presented herein.

Generally, one form of the present system uses novel calibration equations and techniques to evaluate "time-domain reflectometry" (TDR) waveforms in order to characterize soil, especially in the context of construction projects.

Most data presented herein are of ASTM CH Reference Soil. Data from other soils and their analysis and discussions will be developed by those skilled in the art in view of this disclosure. The first portion of this disclosure is organized into three main sections. The first presents current calibration equations in the Purdue One-step method (U.S. Pat. No. 7,040,145 B2, issued May 9, 2006). The second provides hypotheses for new calibration equations. The third and FIGS. 1-2(b) and 1-2(c) suggest a "voltage and density normalization method" using new calibration equations with the introduction of newly utilized parameter, $V_1$, and explains the procedure to determine $V_1$ from a TDR waveform.

Figures 1, 2:
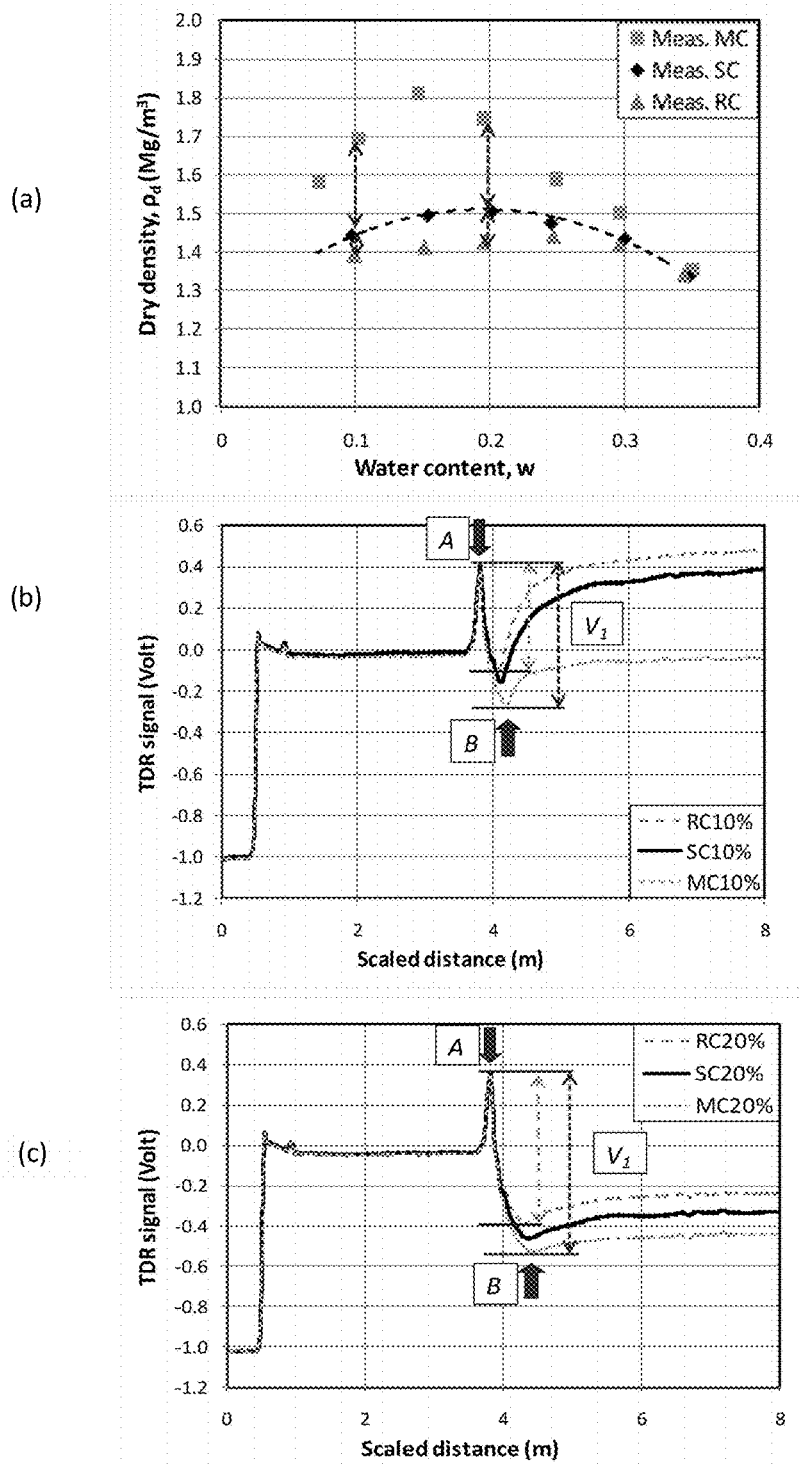
Figures 1, 2, 3, 3A:
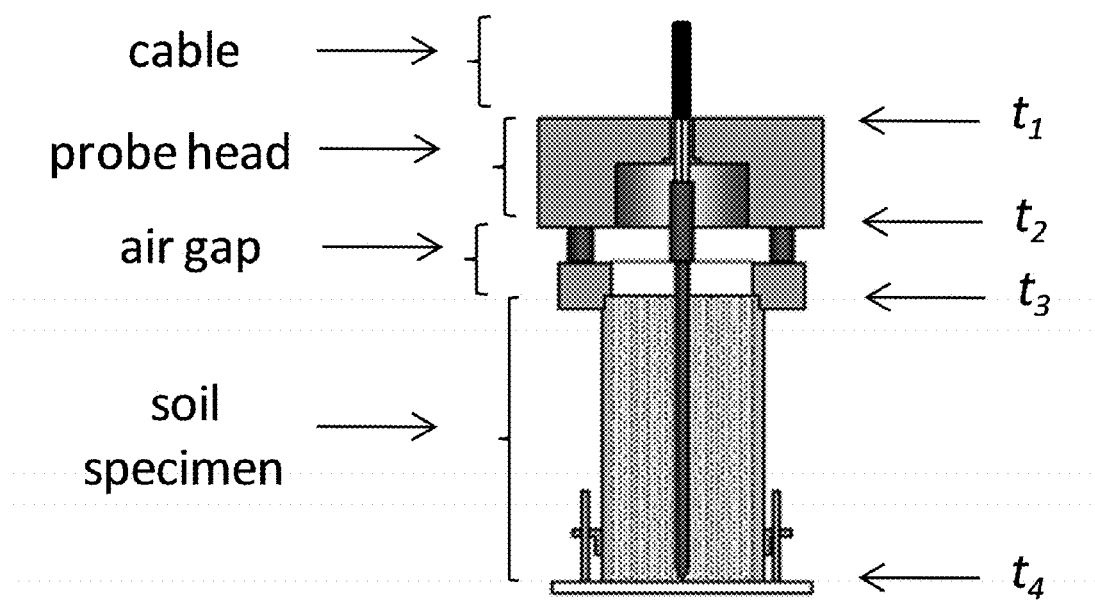

An exemplary TDR waveform is provided in FIG. 3-2, which illustrates the signal produced from ASTM CH soil at standard compaction (SC) with 20% water content. This figure shows the parameters measured in a TDR test where the abscissa is the travel time of the electromagnetic wave converted to a travel distance and the ordinate is the voltage measured at the source. The horizontal travel distance from the first peak (reflection from the soil surface) to the first trough (reflection from the end of the probe) is used to determine the apparent length of travel in the soil specimen.

Measurements include the initial voltage applied by the voltage generator, $V_s$, and the final voltage, $V_f$, after wave propagation has ceased. The measurement of $l_a$, along with the length of the probe $l_p$ embedded in the soil allows for calculating the apparent dielectric constant, $K_a$. The values of $V_s$ and $V_f$ are used in calculating the bulk d.c. electrical conductivity, $EC_b$, for a given probe configuration and voltage generator impedance. The newly utilized parameter, $V_1$, is discussed below.

The existing Purdue One-step method specifies a standard test method for the water content, w, and dry density, $\rho_d$, of soil in place by TDR, and they are outlined in this section. The calibration equations used in the Purdue One-step method are:

$$\sqrt{K_a}\frac{\rho_w}{\rho_d} = a + b \cdot w \tag{1-1}$$

$$\sqrt{EC_b}\frac{\rho_w}{\rho_d} = c + d \cdot w \tag{1-2}$$

where $K_a$ and $EC_b$ are dielectric constant and bulk electrical conductivity of soil measured by TDR test, respectively, a, b, c, and d are soil-type dependent calibration coefficients, and $\rho_w$ is the density of water.

However, w and $\rho_d$ calculated by Equations (1-1) and (1-2) do not generally have satisfactory reliability. Since Equation (1-2) is dependent on pore fluid conductivity, and the field sample has generally different pore fluid conductivity from that of the laboratory sample, c and d in Equation (1-2) obtained from laboratory tests do not apply for the sample measured in the field. Thus, the current Purdue One-step method (Equations (1-1) and (1-2)) requires another equation since $EC_b$ for pore fluid conductivity used in the field is not easily determined. In other words, $EC_b$ is adjusted by utilizing $K_a$ since $K_a$ is relatively independent of pore fluid conductivity as follows:

$$\sqrt{EC_{b,adj}} = f + g \cdot \sqrt{K_a} \tag{1-3}$$

where $EC_{b,adj}$ is "adjusted" value from TDR-measured $EC_b$, and f and g are soil-type dependent calibration coefficients.

As a result, $EC_b$ is coupled with $K_a$ using the empirical relationship given in Equation (1-3), allowing for the prediction of w and $\rho_d$ of soil in place using the following equations:

$$w = \frac{c \cdot \sqrt{K_a} - a \cdot \sqrt{EC_{b,adj}}}{b \cdot \sqrt{EC_{b,adj}} - d \cdot \sqrt{K_a}} \tag{1-4}$$

$$\rho_d = \frac{d \cdot \sqrt{K_a} - b \cdot \sqrt{EC_{b,adj}}}{a \cdot d - c \cdot b} \cdot \rho_w \tag{1-5}$$

FIG. 1-1 presents the results of w and $\rho_d$ calculated by Equations (1-4) and (1-5) (denoted by solid squares with dashed lines), compared to the results from the direct measurements of oven-drying w and $\rho_d$ measured from moist density and water content (denoted by hollow squares with no line). It is noteworthy that the results obtained through the use of Equations (1-4) and (1-5) give an almost linear relationship between water content and dry density which yields only approximate answers. However, it is also noteworthy that this example used data for ASTM CH Reference Soils which contains more than 98% of fine materials and has a wide range of w (approximately from 50 to 200% of optimum water content). Some aspects of the current Purdue One-step method include: 1) the methodology uses on measured values of $K_a$ to determine "adjusted" values of $EC_b$, and 2) the results from the methodology are reliable only over a range of water contents, since the assumed linear relationship between $\sqrt{EC_b}$ and $\sqrt{K_a}$ (Equation 1-3) assumes a linear relationship between w and $\rho_d$ of soil.

Since Topp's Equation is not adequate for all soils, the efforts have been made to develop different types of calibration relationships between $K_a$ and volumetric water content, $\theta$. It has been shown that the density of soil affects the relationship between $K_a$ and $\theta$. They also reported that calibration can be improved if dry density of soil is included or normalized in the relationship.

Gravimetric water content, w, can be used along with soil dry density, $\rho_d$, as given in Equation (1-1) for application to geotechnical practice after examining different calibration equations for a broad range of soil types and densities. Equation (1-1) is relatively insensitive to the soil type. Equation (1-1) can be expressed in terms of the volumetric water content, $\theta$ by multiplying by $$\frac{\rho_w}{\rho_d}$$

as follows:

$$\sqrt{K_a} = a \cdot \frac{\rho_d}{\rho_w} + b \cdot \theta \tag{1-6}$$

where $$\theta = w \frac{\rho_d}{\rho_w}.$$

When $\theta$ is zero (dry soil), Equation (1-6) reduces to:

$$a = \sqrt{(K_a)_{solids}} \cdot \frac{\rho_w}{\rho_d} \tag{1-7}$$

where $(K_a)_{solids}$ is $K_a$ of soil solids.

Thus, the value of coefficient a is related to both $\rho_d$ and $K_a$ of soil solids. Values of $K_a$ for common dry soils and rock materials commonly vary from about 2 to about 7. Values of $\rho_d$ are commonly about 1.4 to 2.2 times that of water, $\rho_w$. Substituting these values into Equation (1-7), the value of a varies from approximately 0.6 to 1.9.

When $\theta$ is 100% (water only), the value of $\rho_d$ becomes zero and Equation (1-6) reduces to:

$$b = \sqrt{(K_a)_{water}} \tag{1-8}$$

where $(K_a)_{water}$ is $K_a$ of water.

Thus, the value of coefficient b is related to $K_a$ of water, and for deionized water at room temperature, it is approximately 9. Some measured values of b for a variety of soils vary from 7 to 12, with the majority falling between 8 and 9.

It has also been found that Equation (1-1) remains largely unaffected by changes in soil density, compaction energy, and pore fluid conductivity for sandy and clayey soils commonly used in geotechnical earthwork construction. Thus, attempts were made to replace Equations (1-2) and (1-3) with new calibration equations that overcome the shortcomings of their use.

Figures 1A, 2:
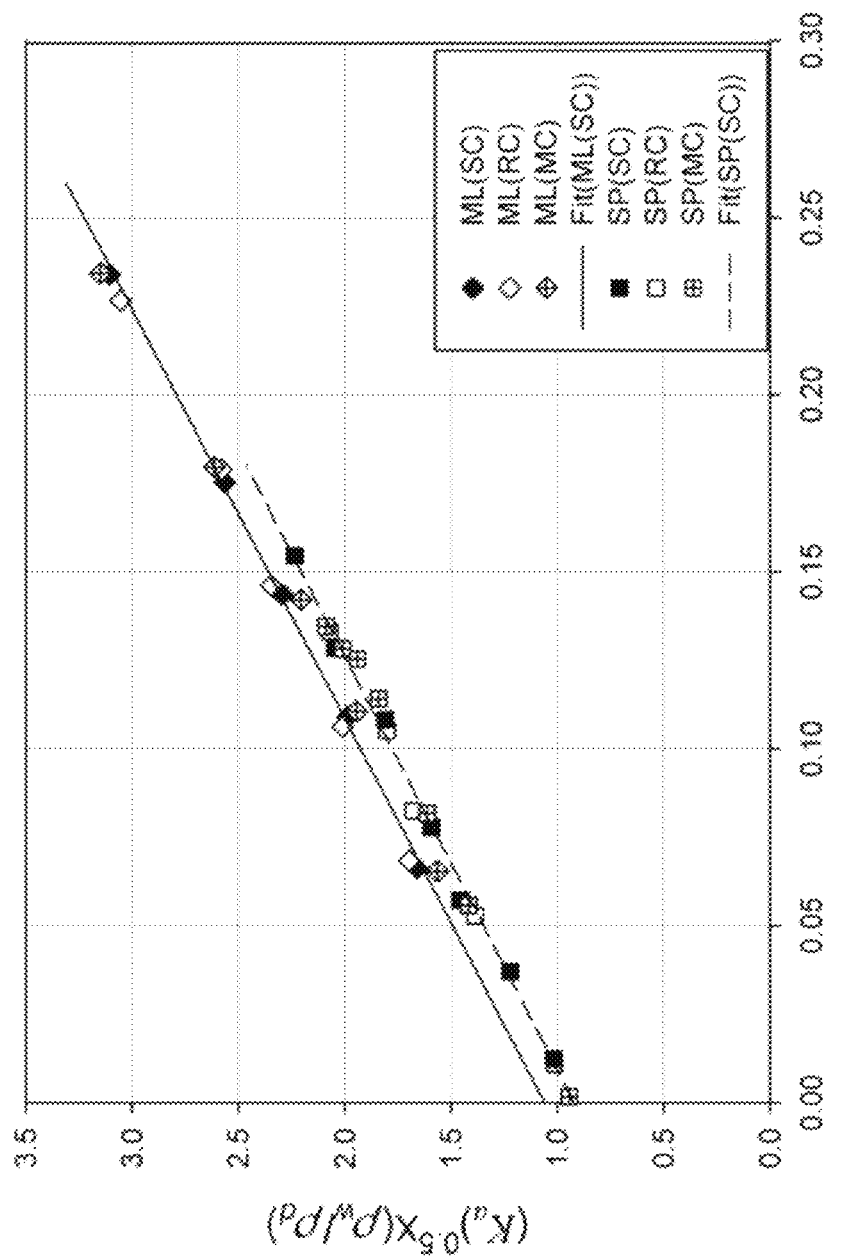
Figures 1B, 2:
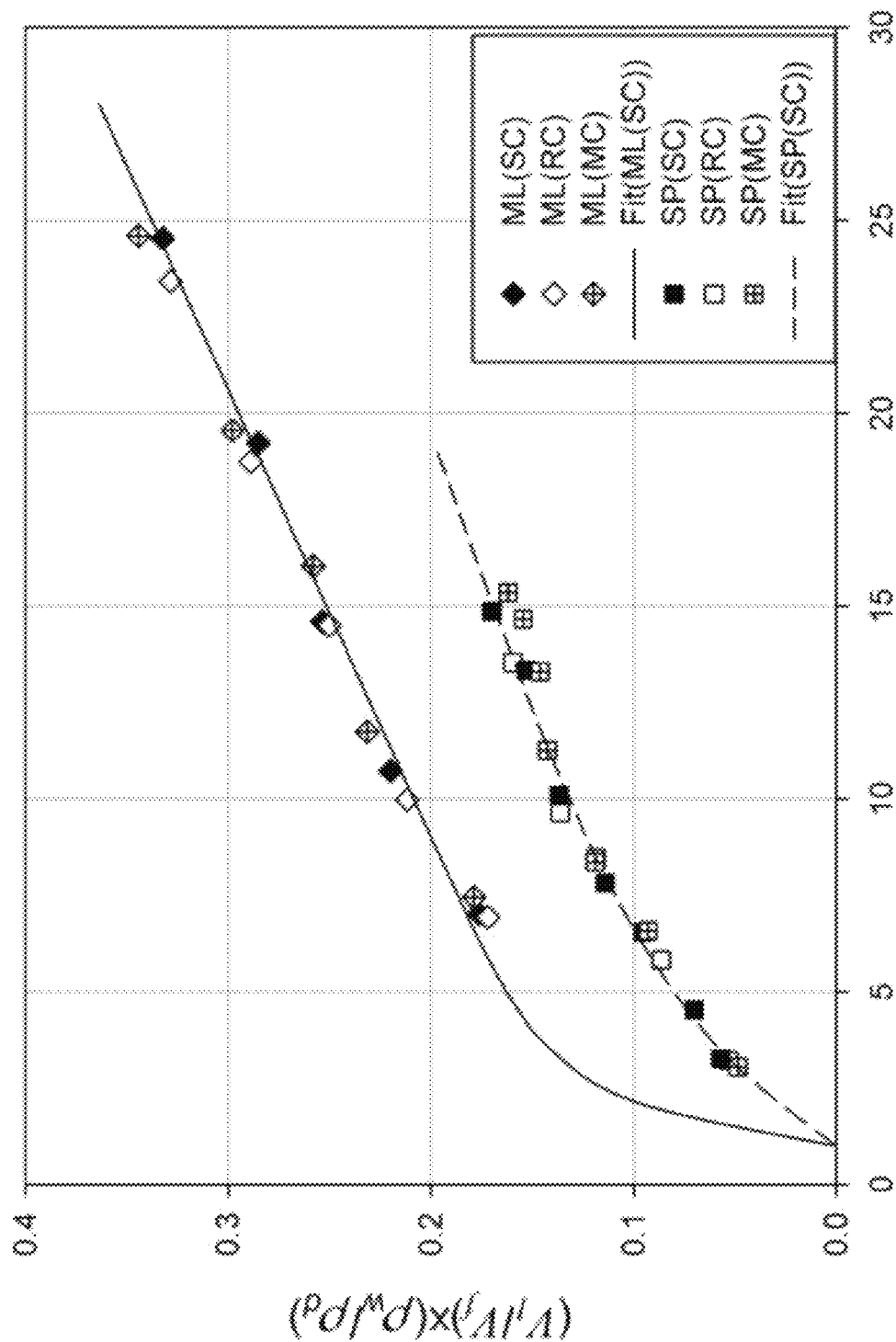
Figures 1C, 2:
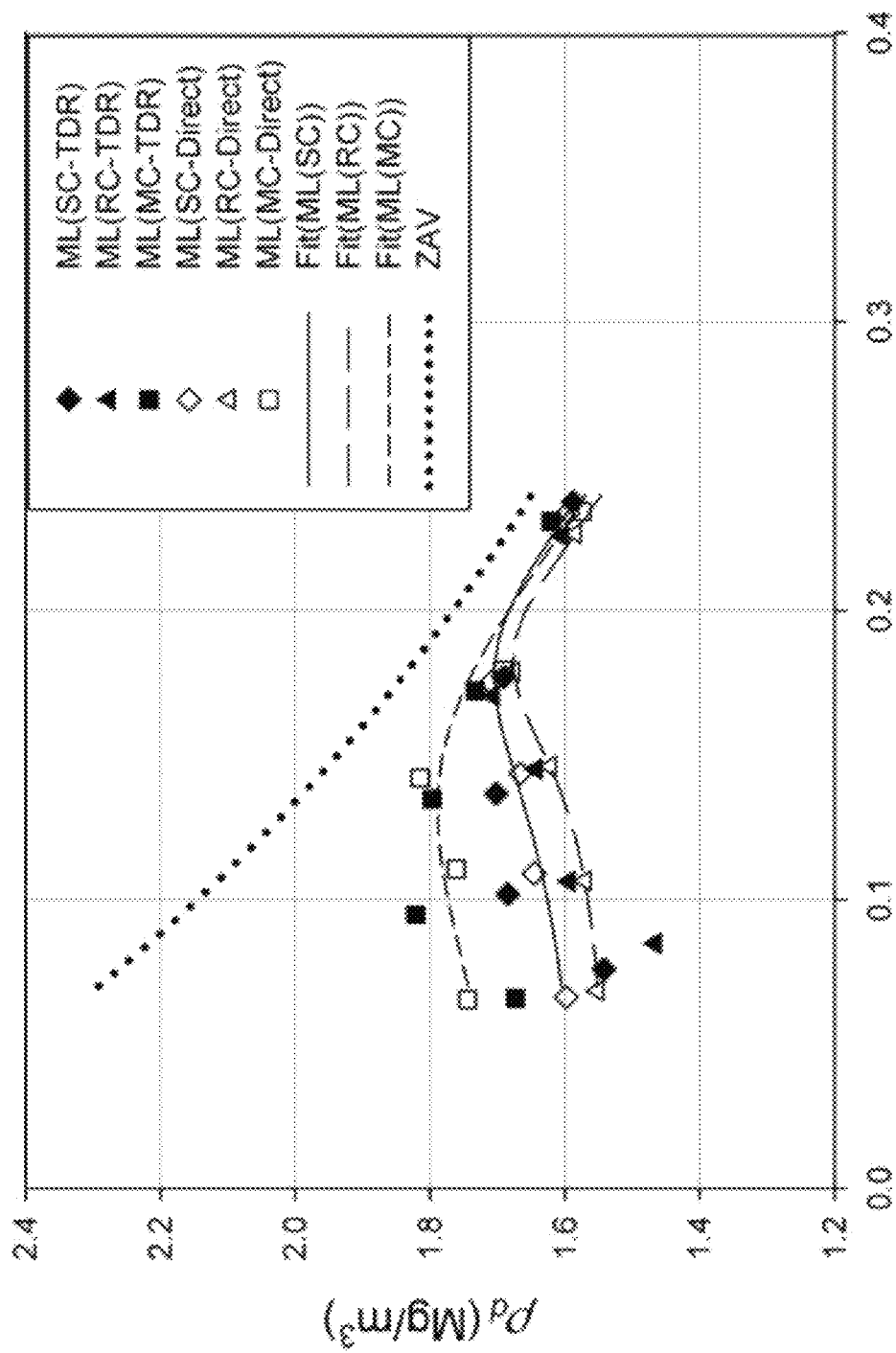
Figures 1D, 2:
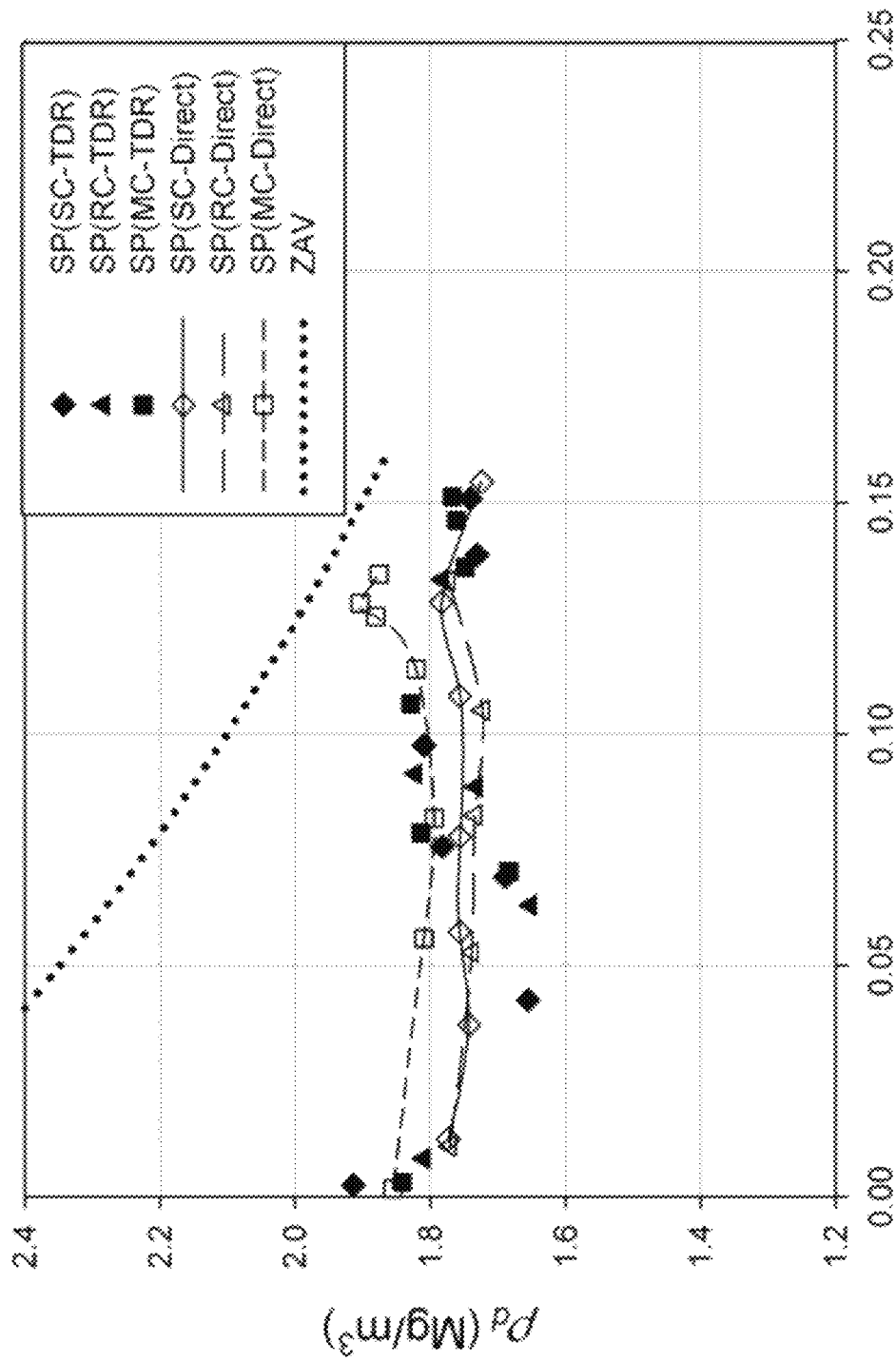
Figures 2, 2A:
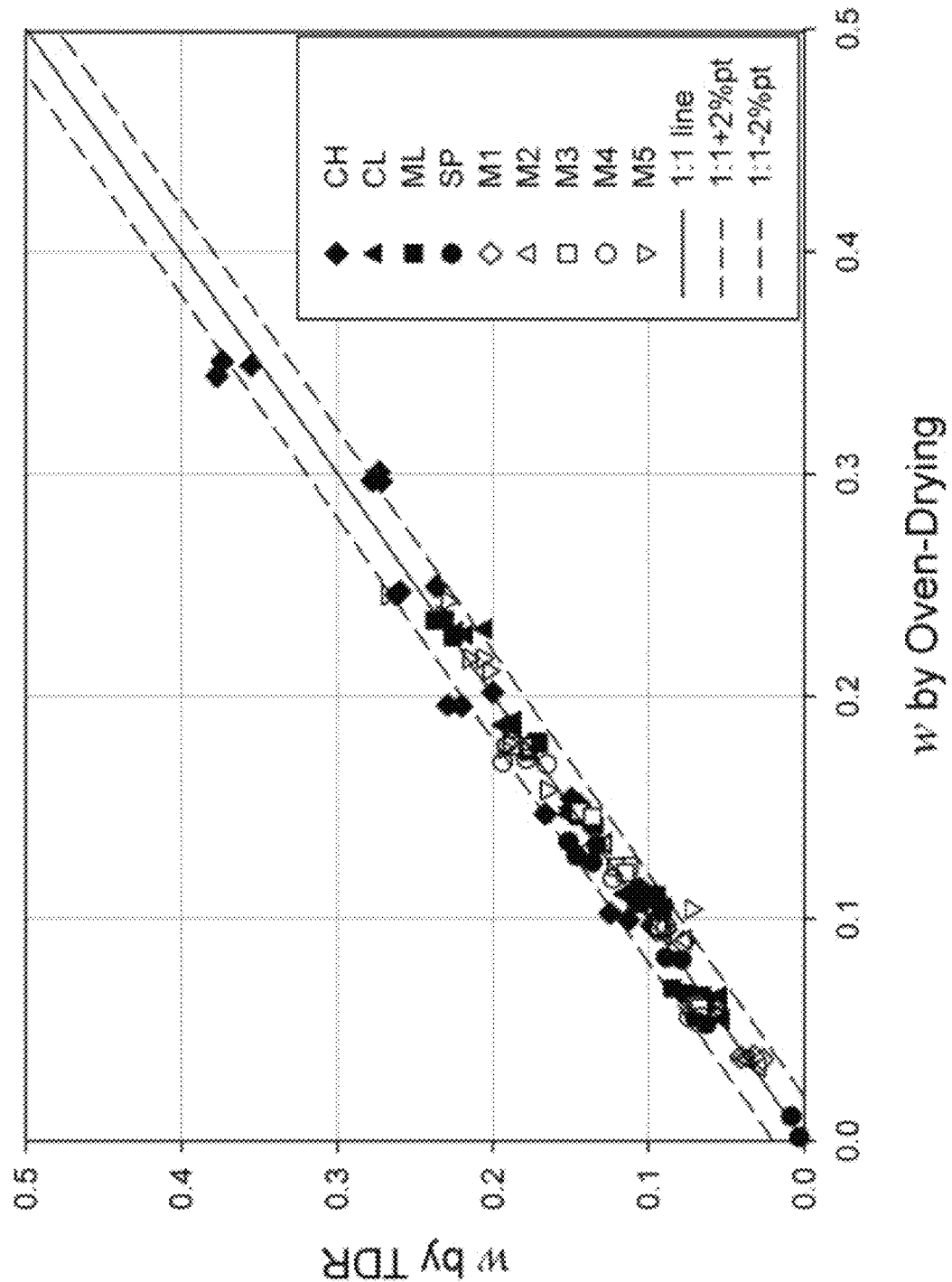
Figures 2, 2B:
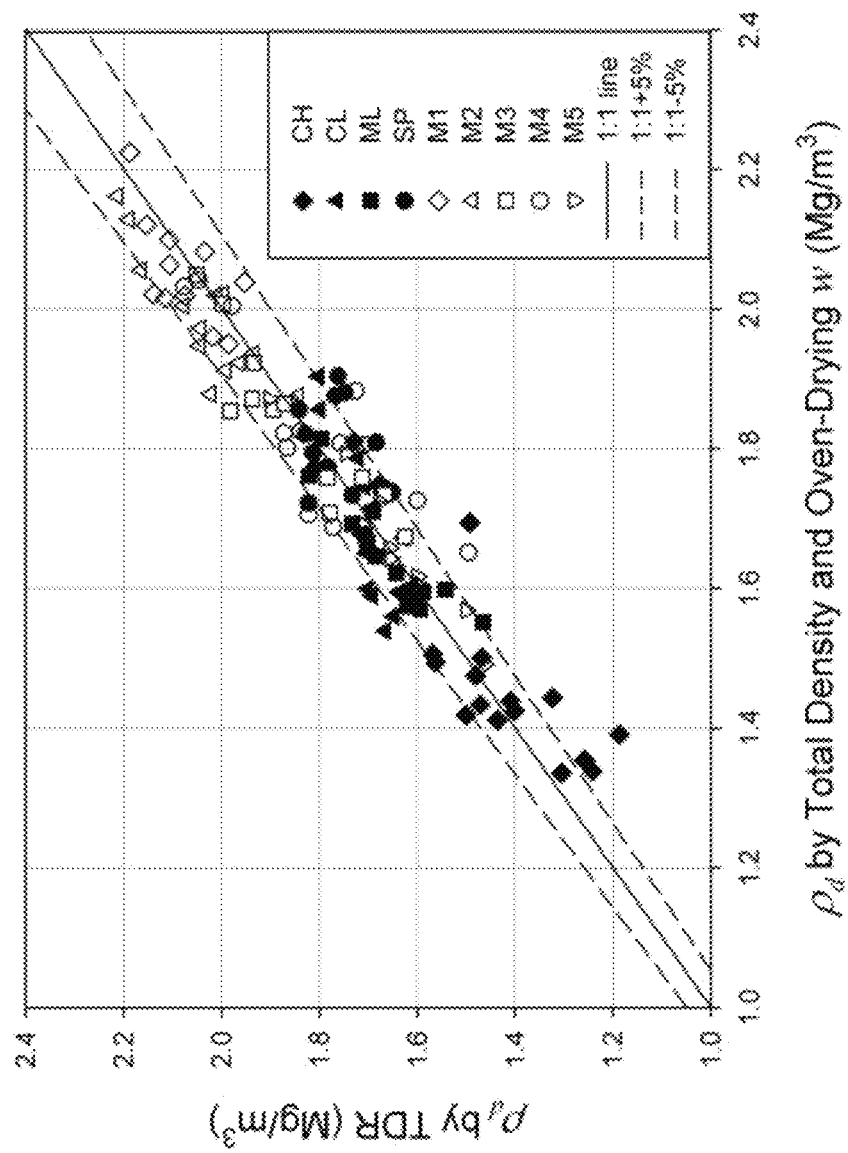
Figures 2, 3:
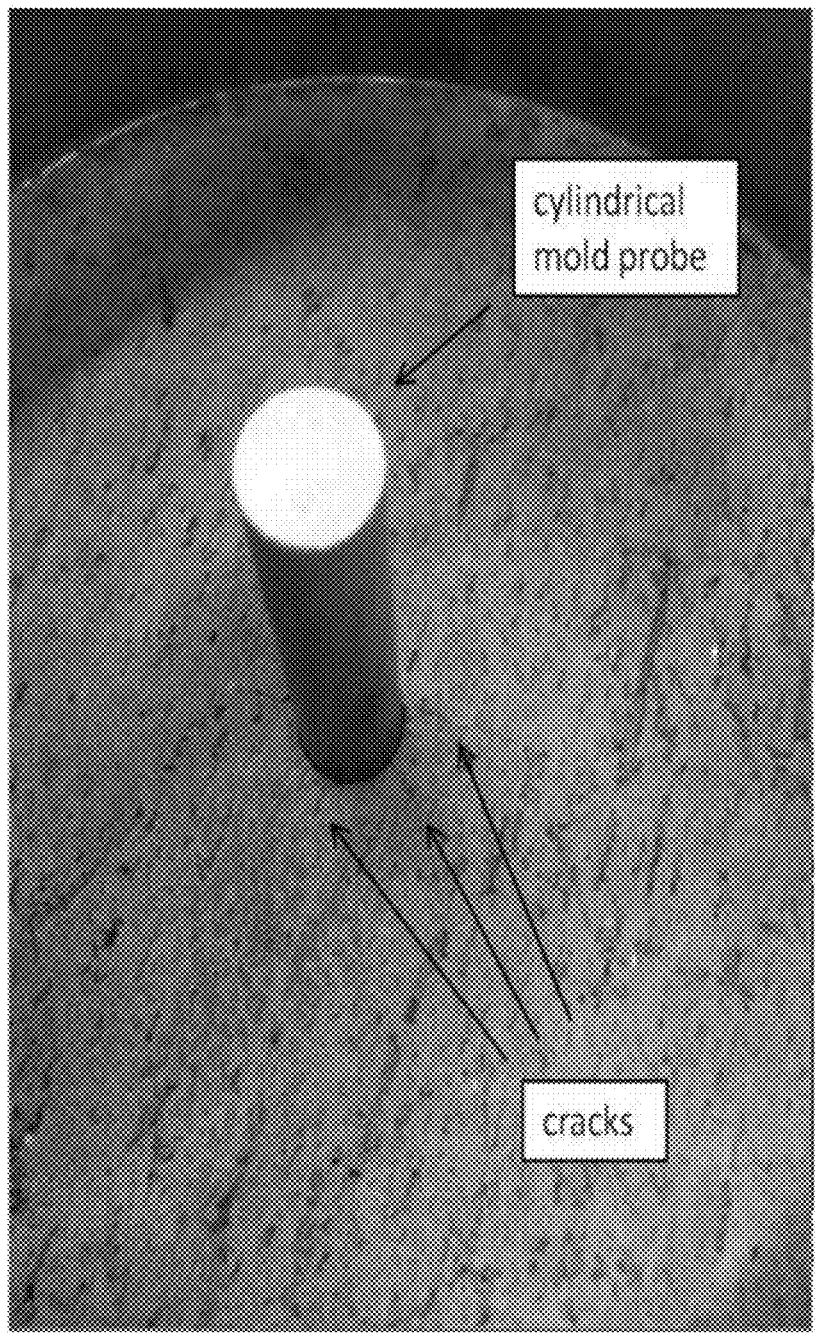
Figures 2, 3, 4, 4A:
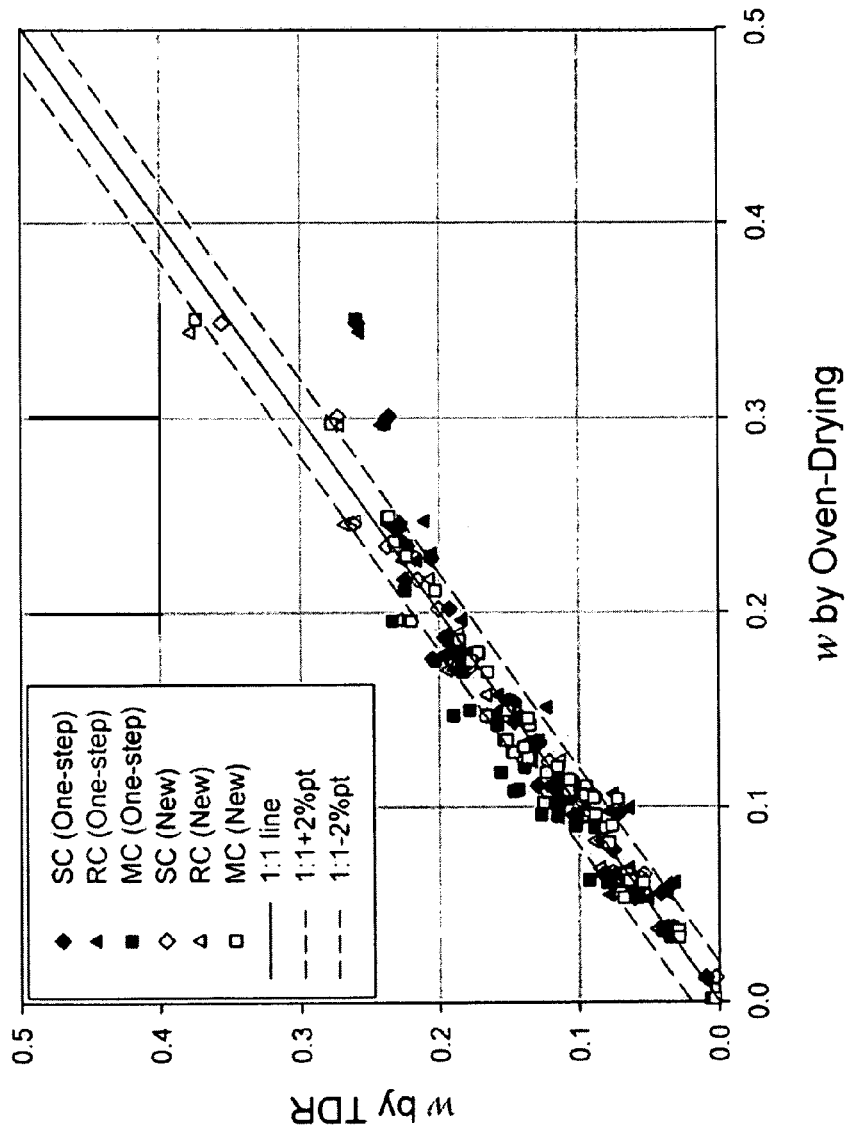
Figures 2, 3, 4, 4B:
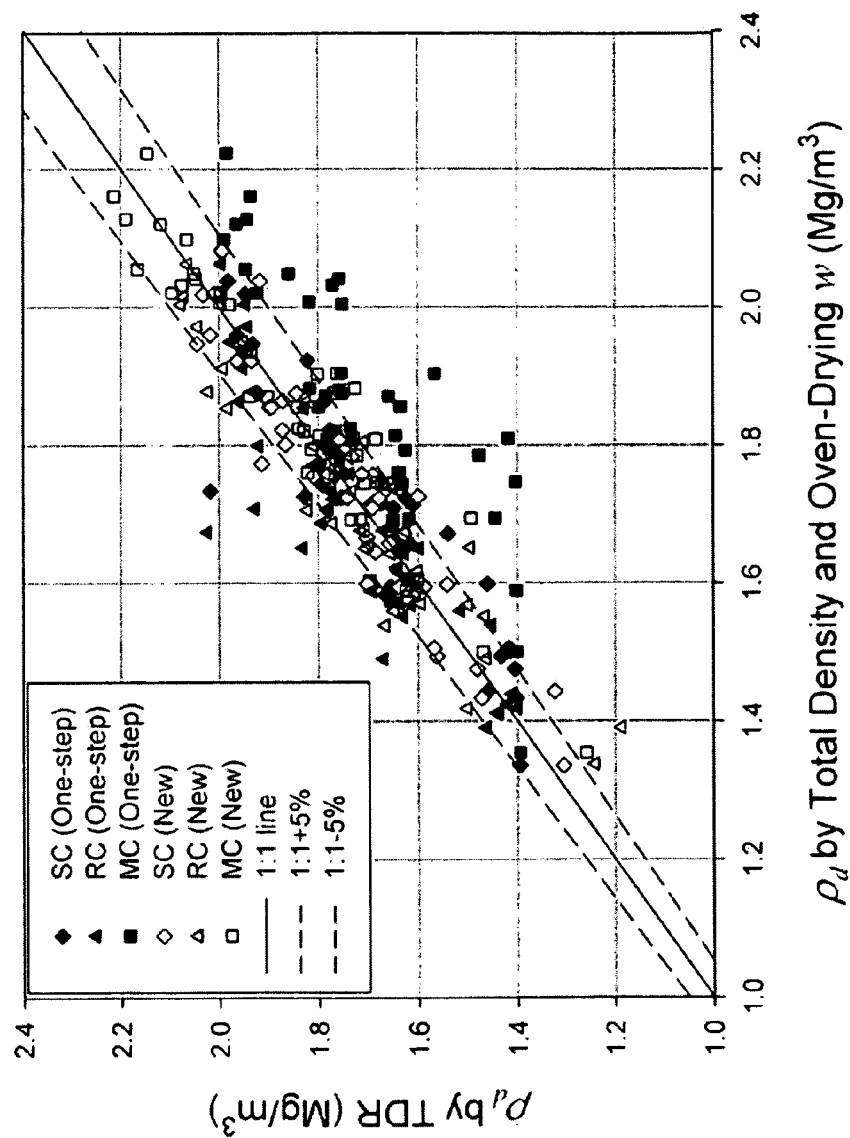
Figures 2, 3, 4, 5, 5A:
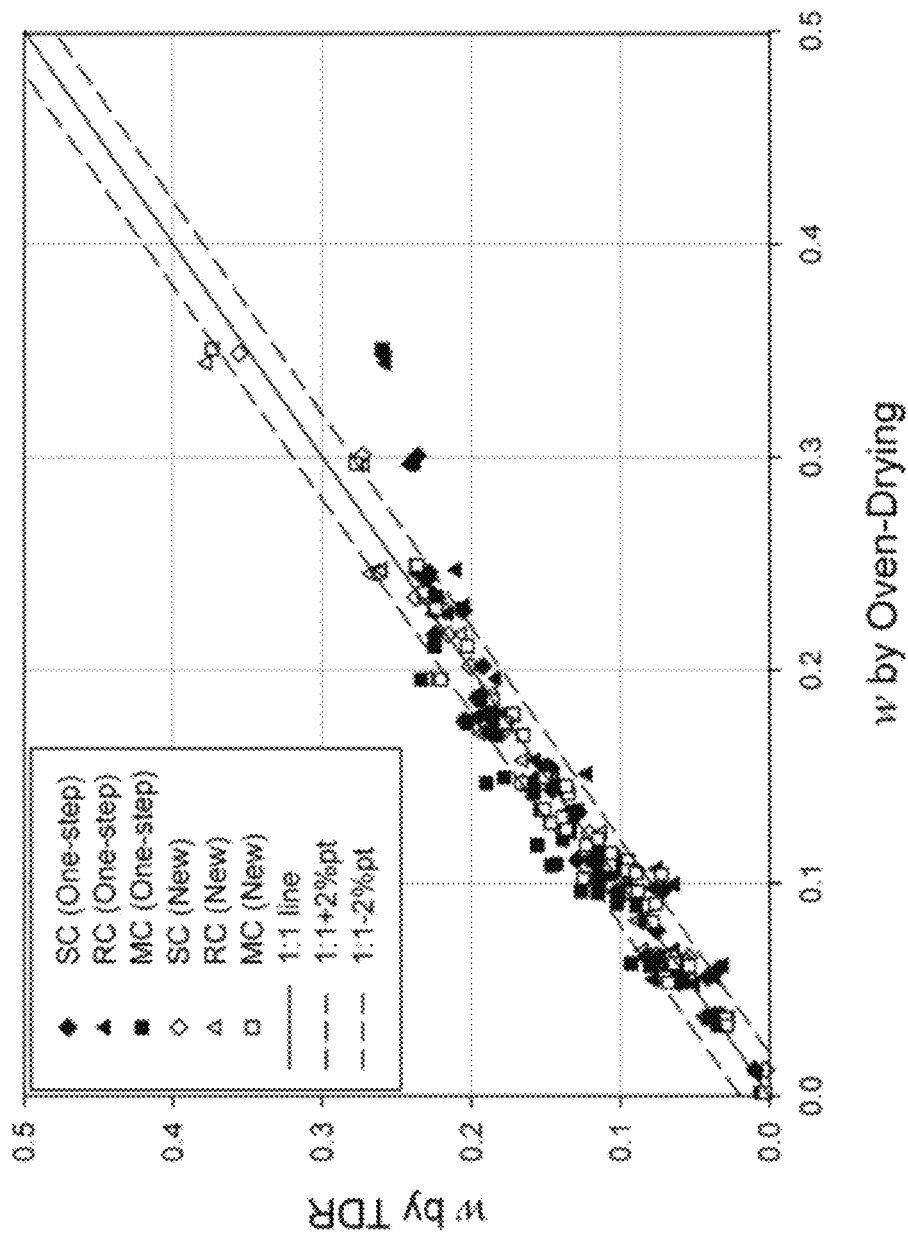
Figures 2, 3, 4, 5, 5B:
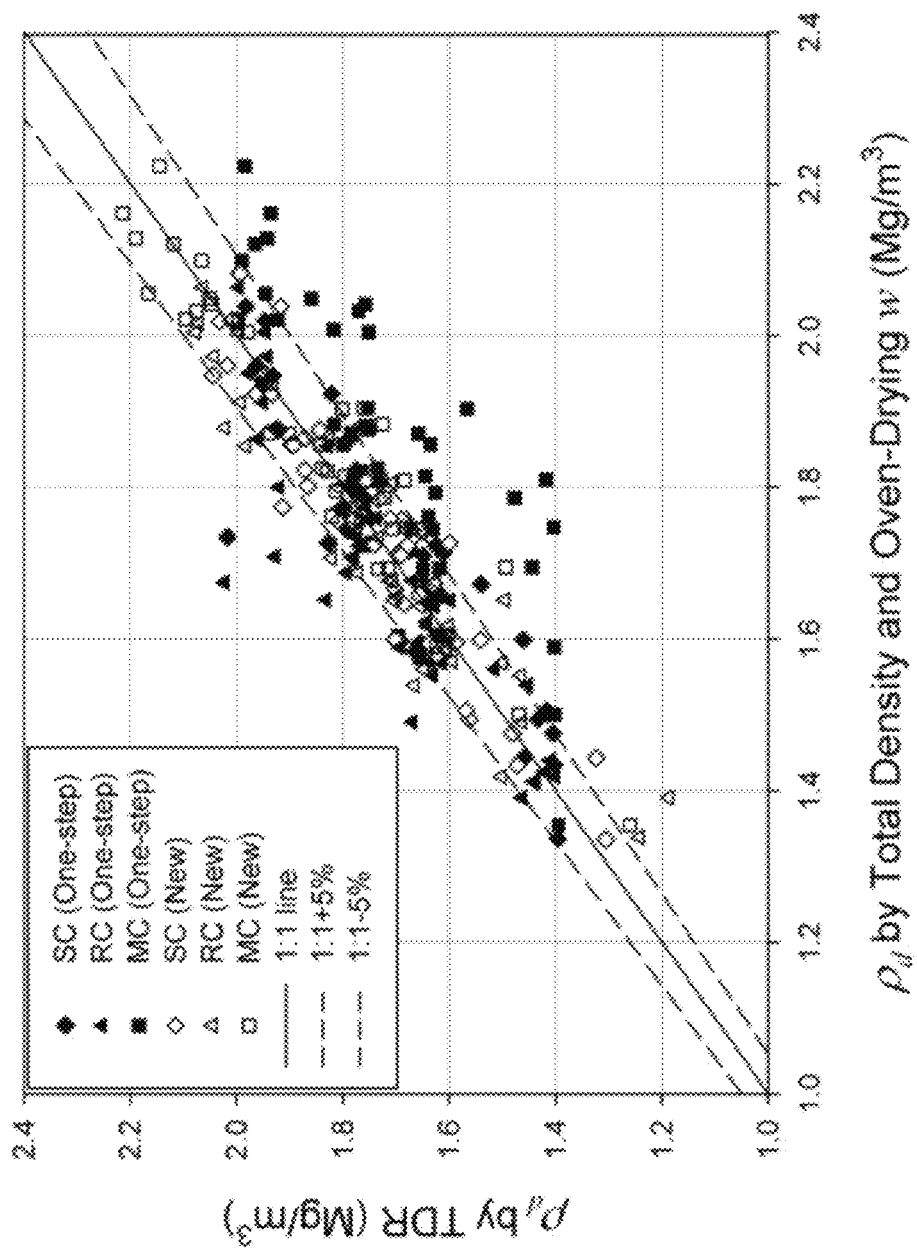
Figures 1, 3:
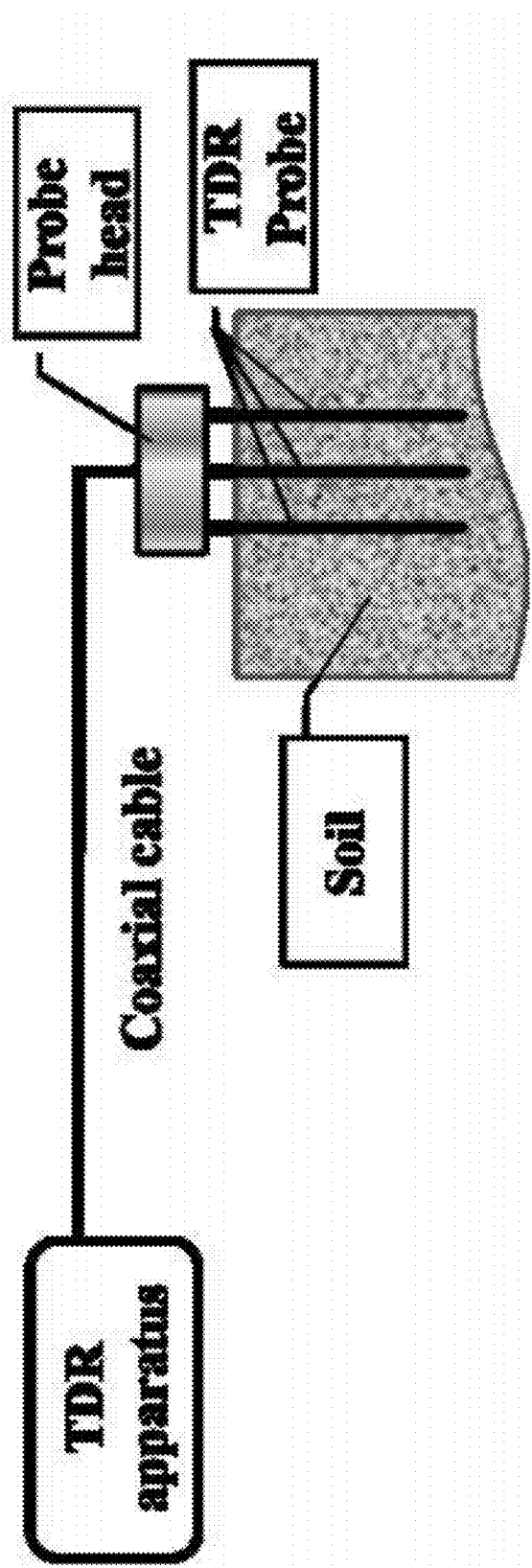
Figures 2, 3:
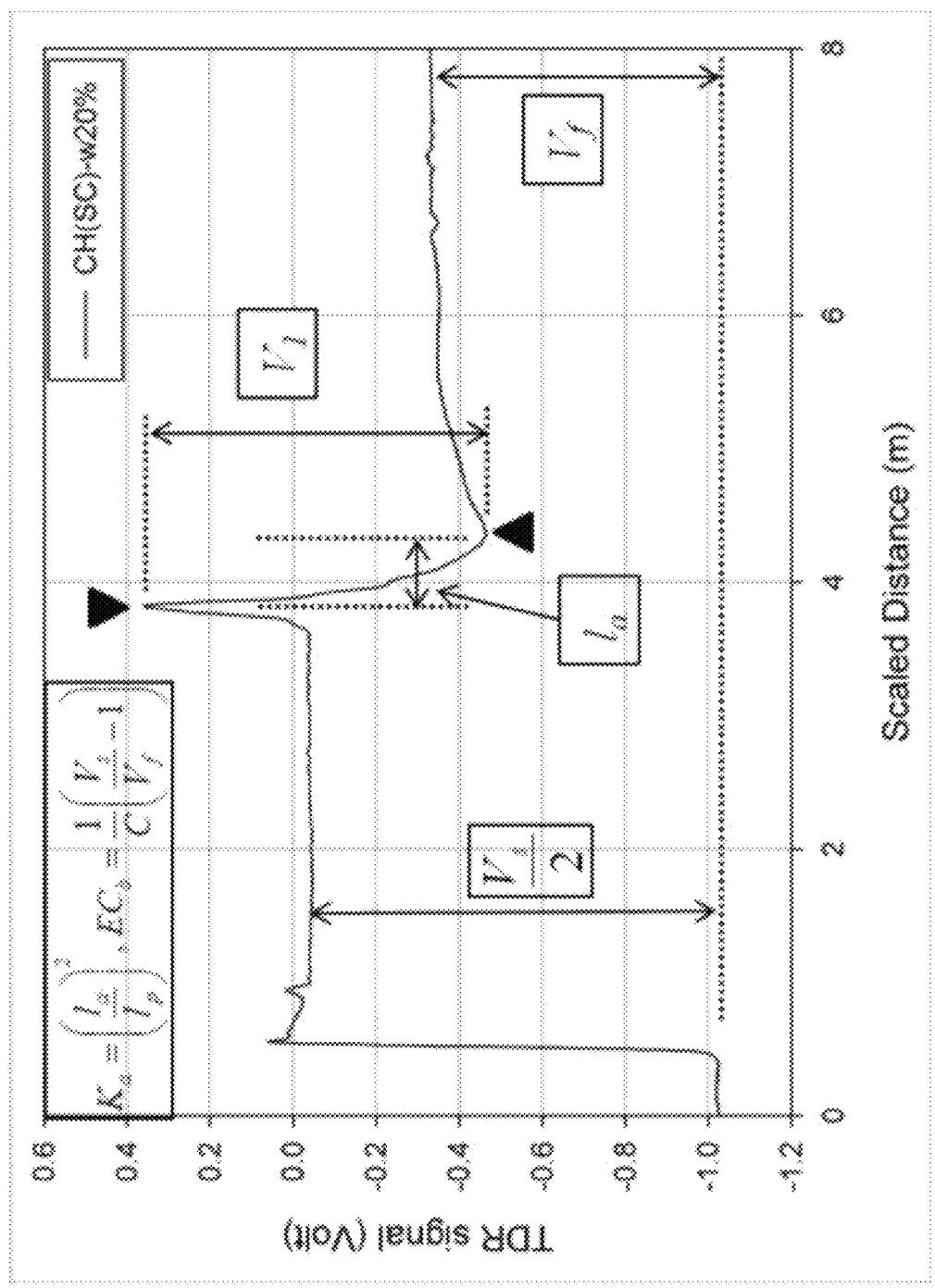
Figures 3, 3A:
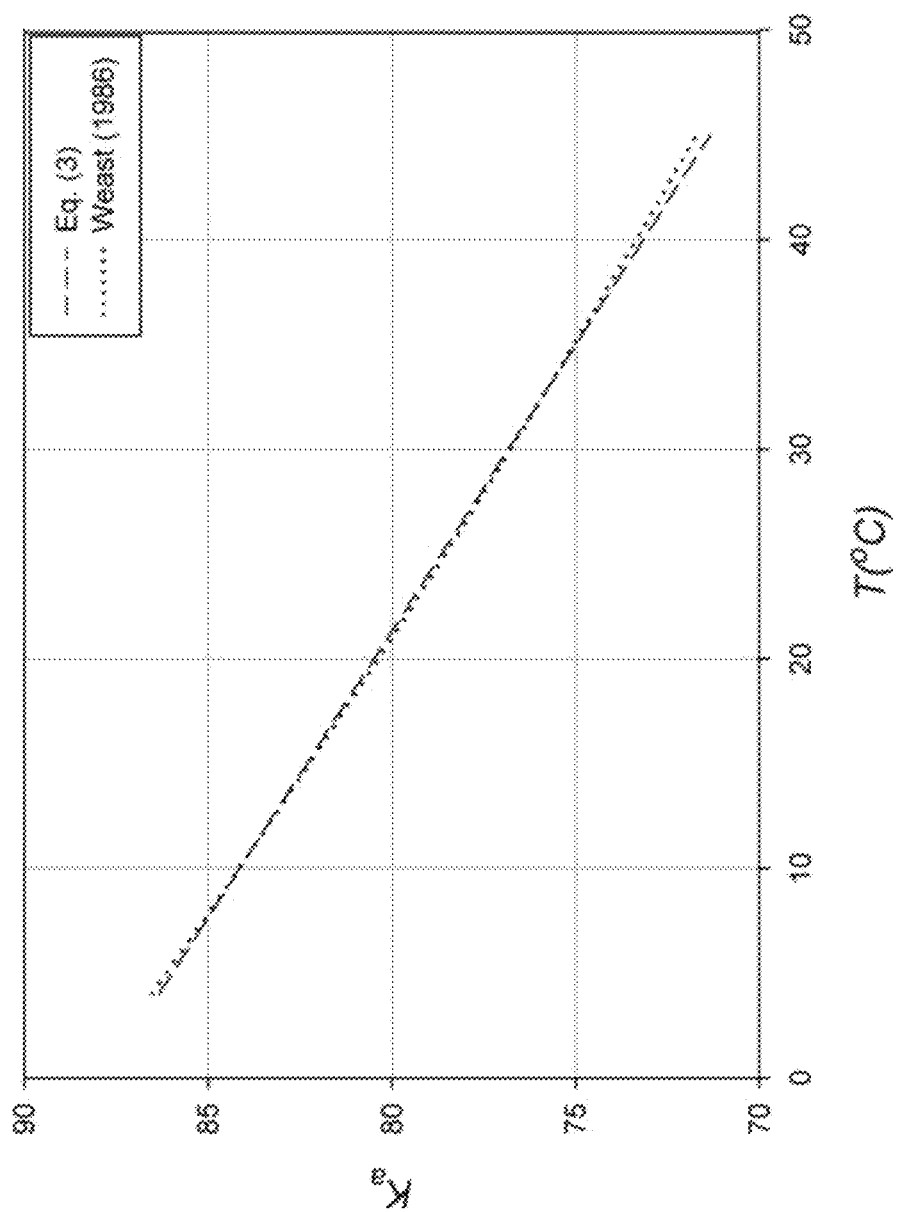
Figures 3, 3B:
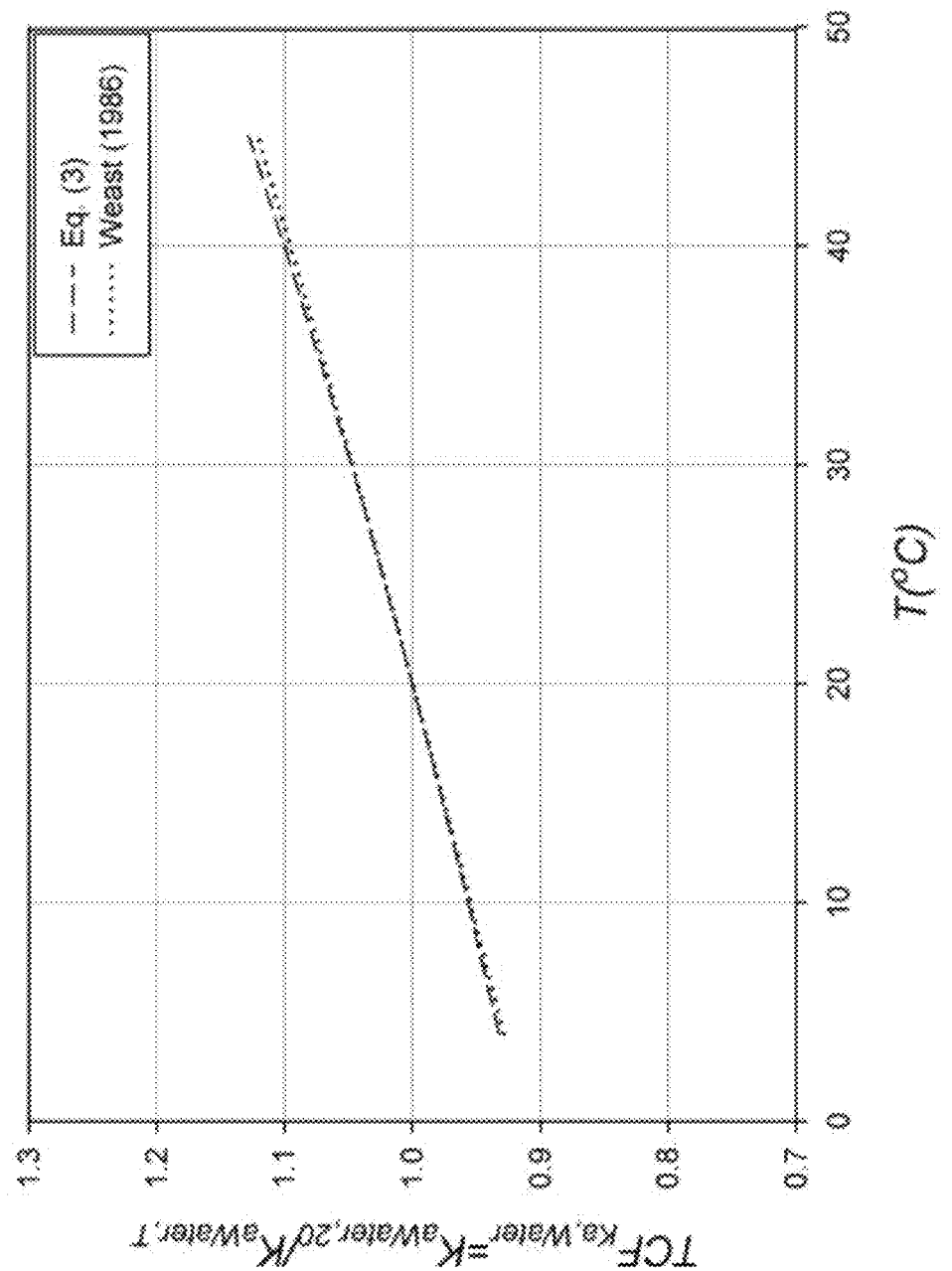
Figures 3, 4, 4A:
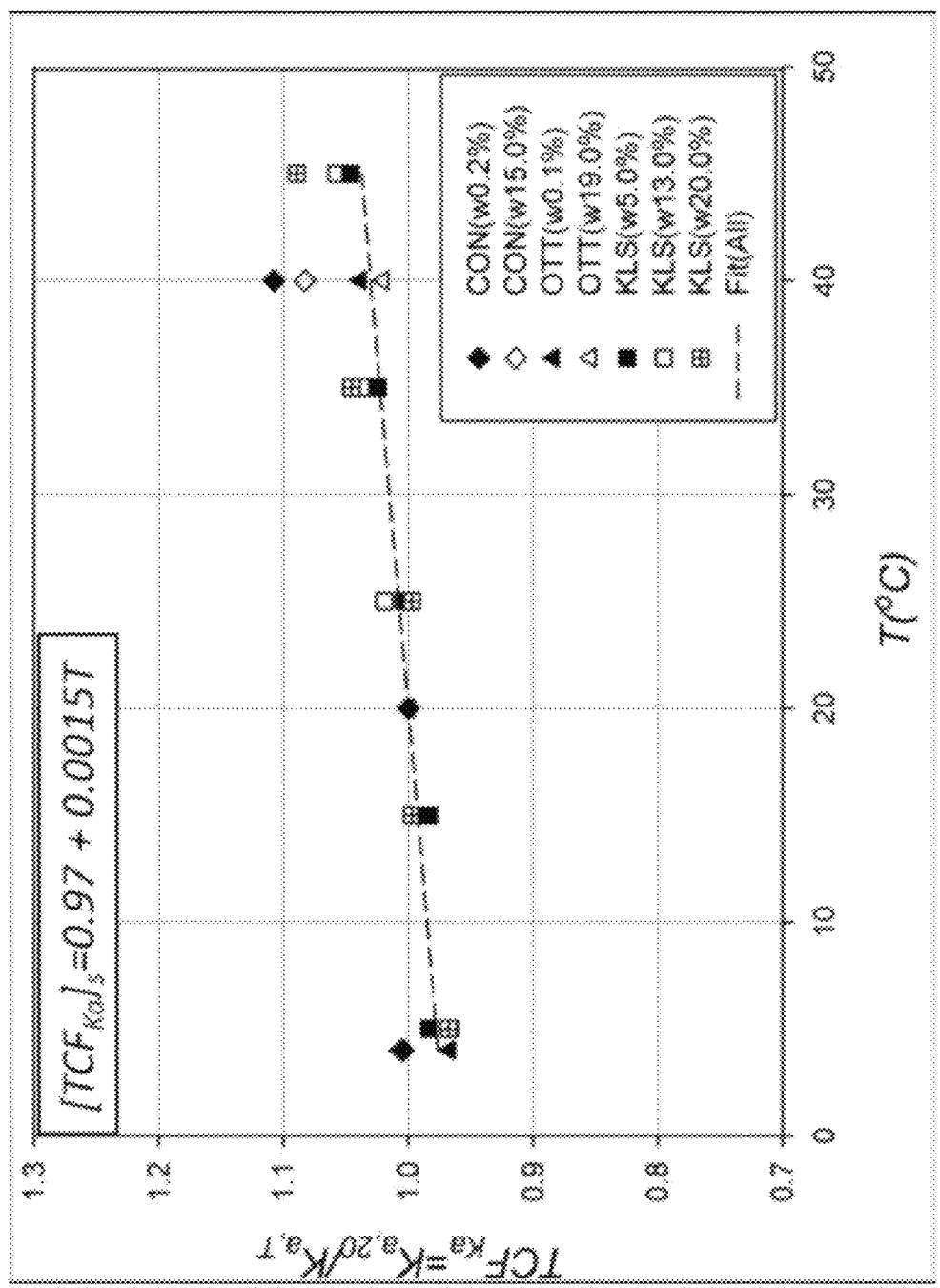
Figures 3, 4, 4B:
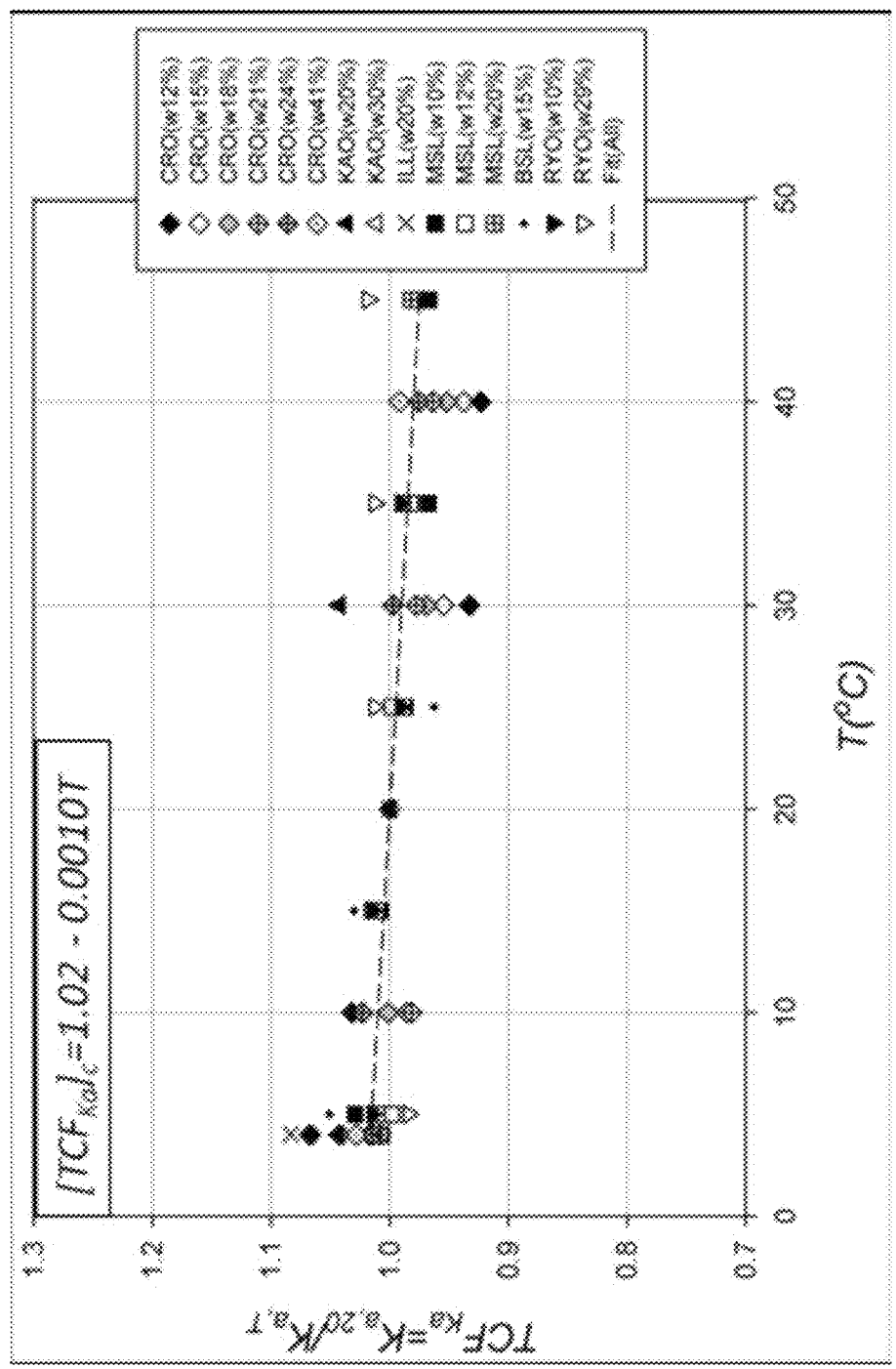
Figures 3, 4, 5, 5A:
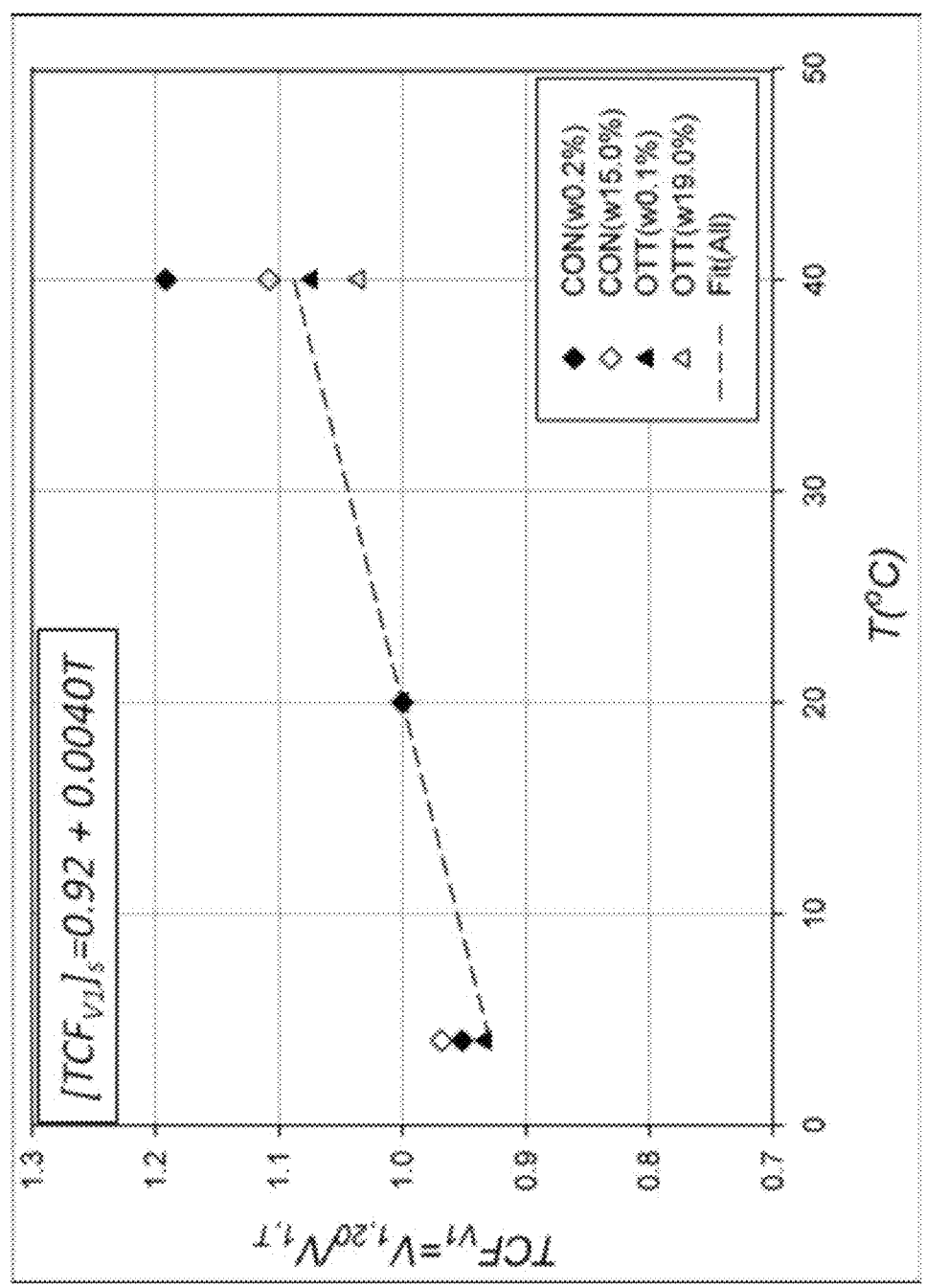
Figures 3, 4, 5, 5B:
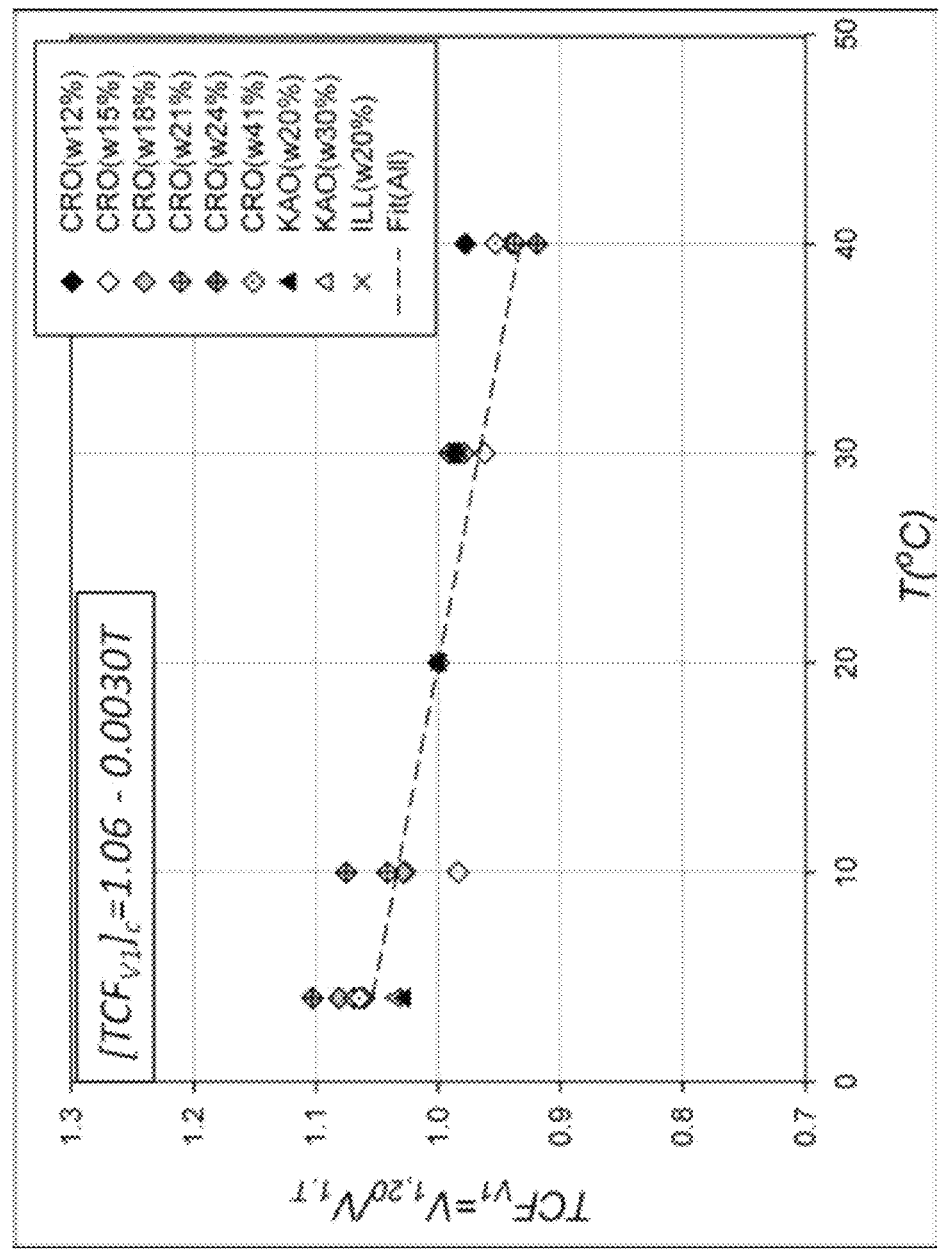
Figures 3, 4, 5, 6, 6A:
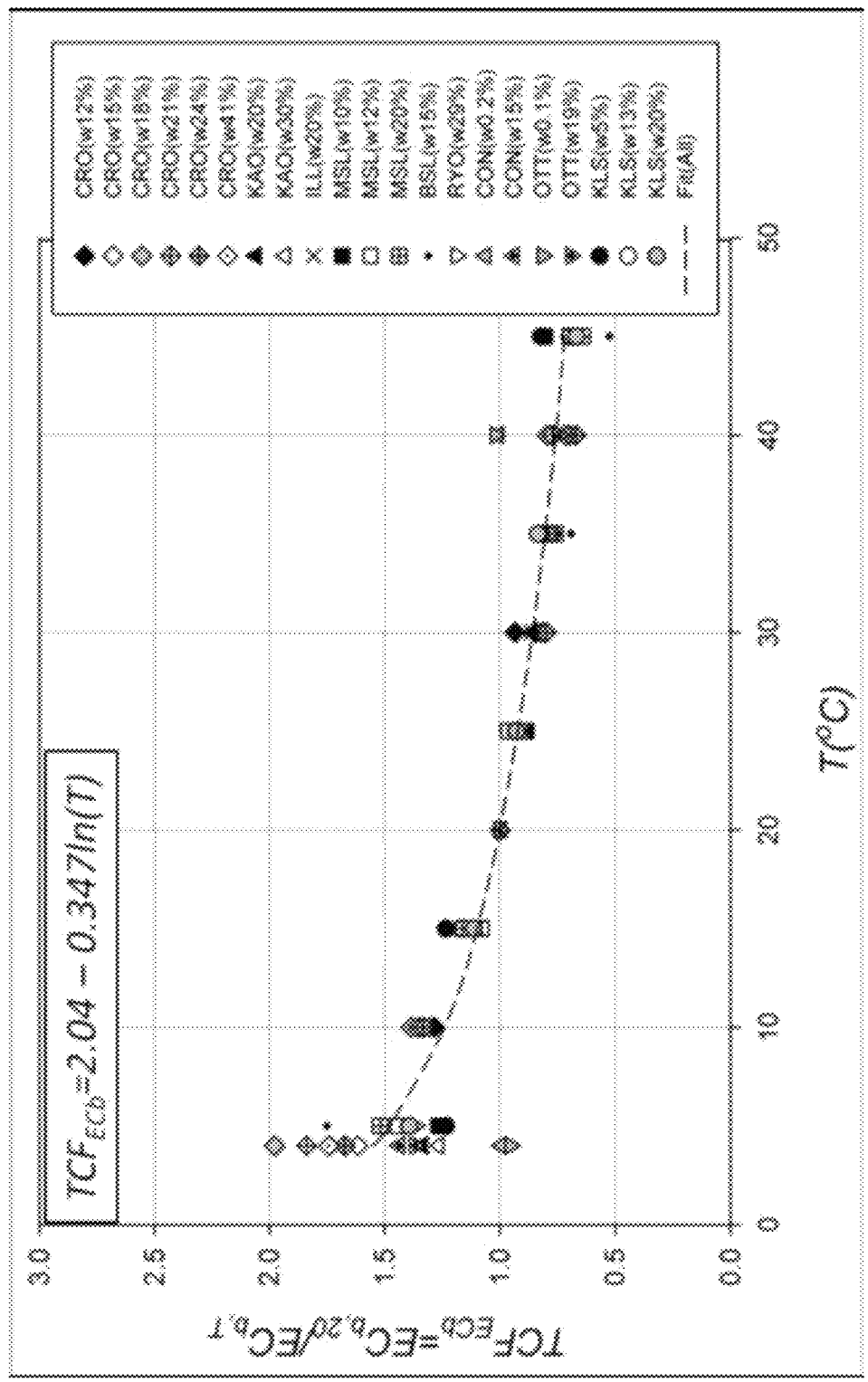
Figures 3, 4, 5, 6, 6B:
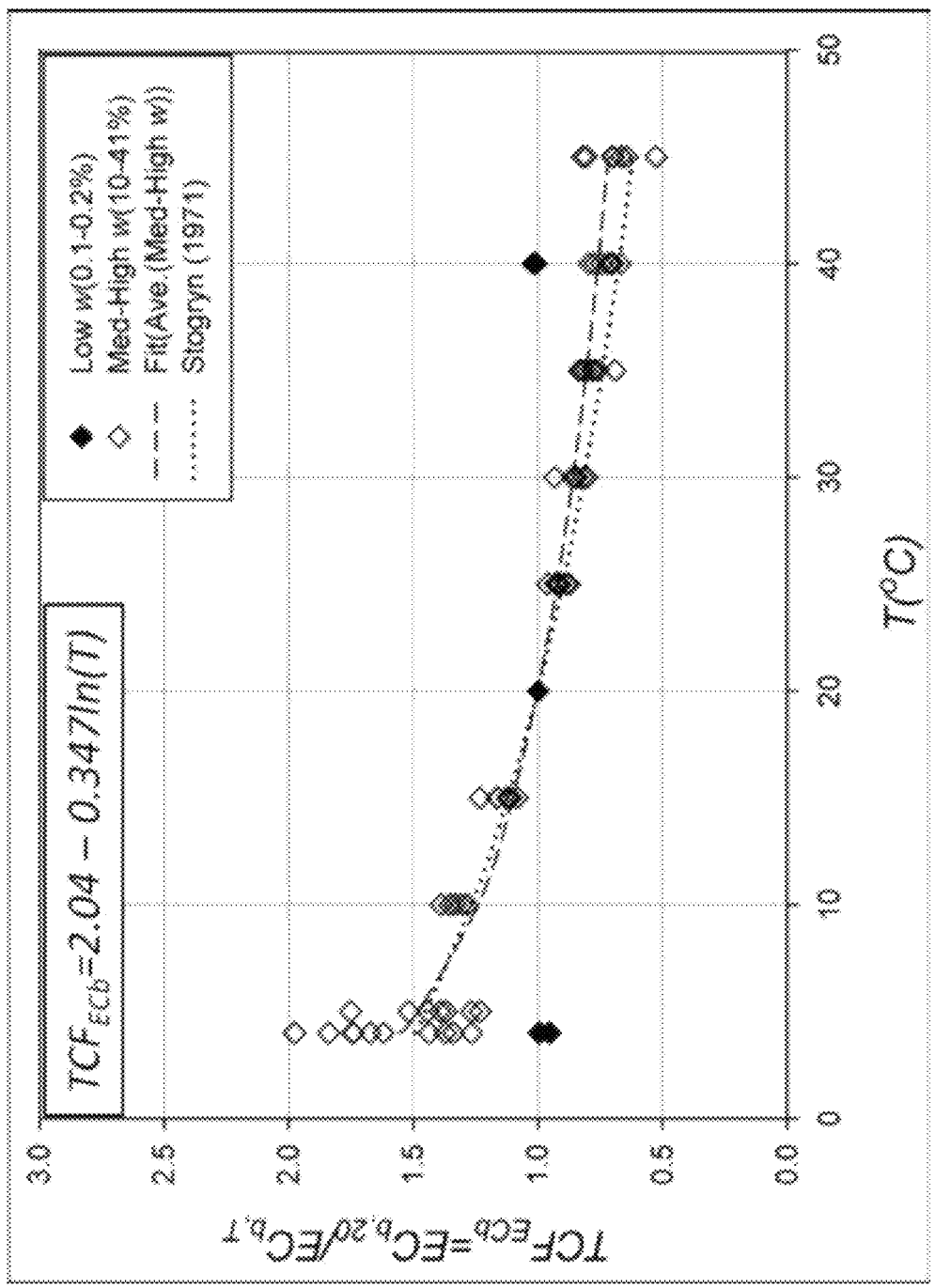
Figures 3, 4, 5, 6, 7, 7A:
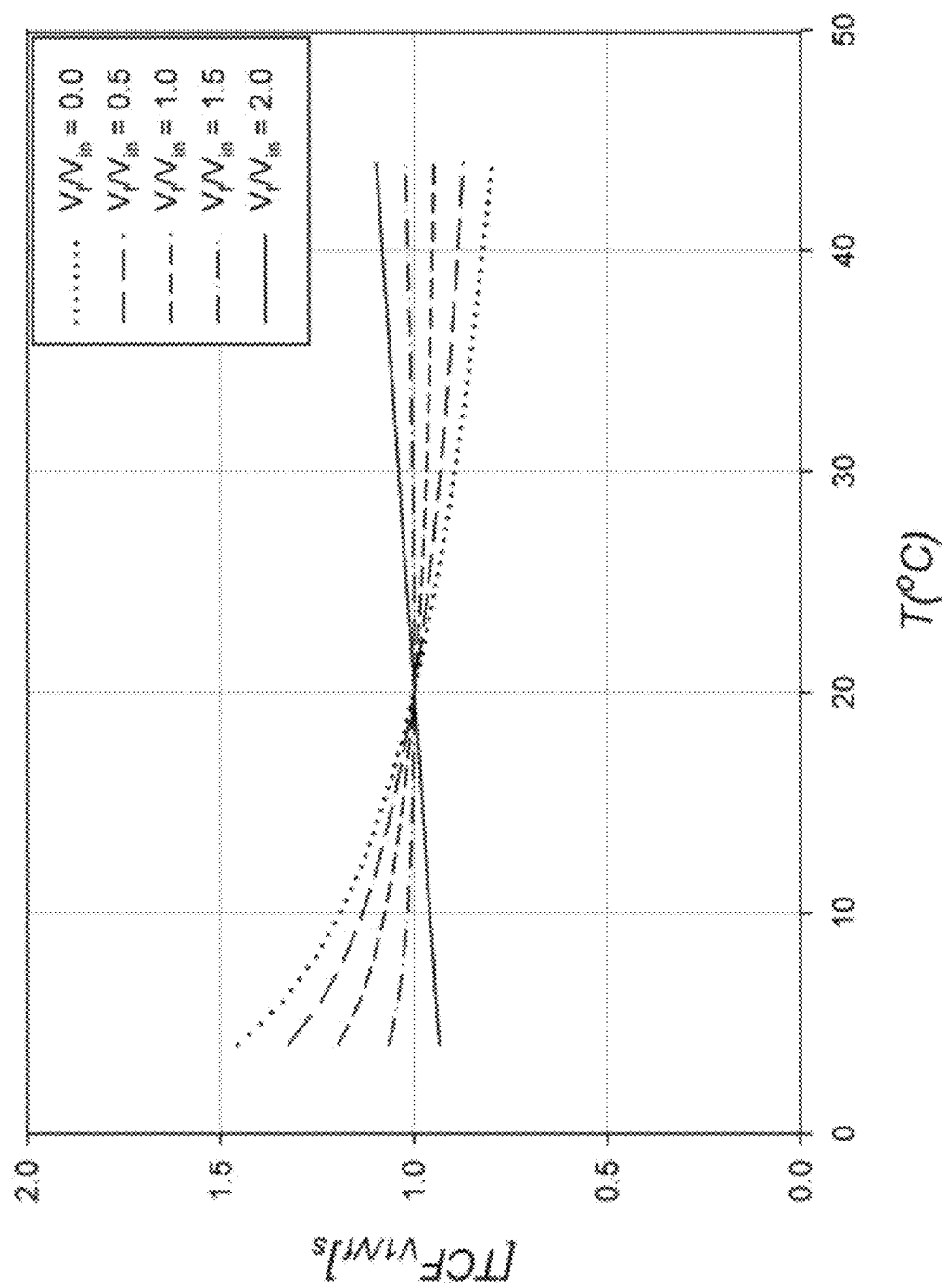
Figures 3, 4, 5, 6, 7, 7B:
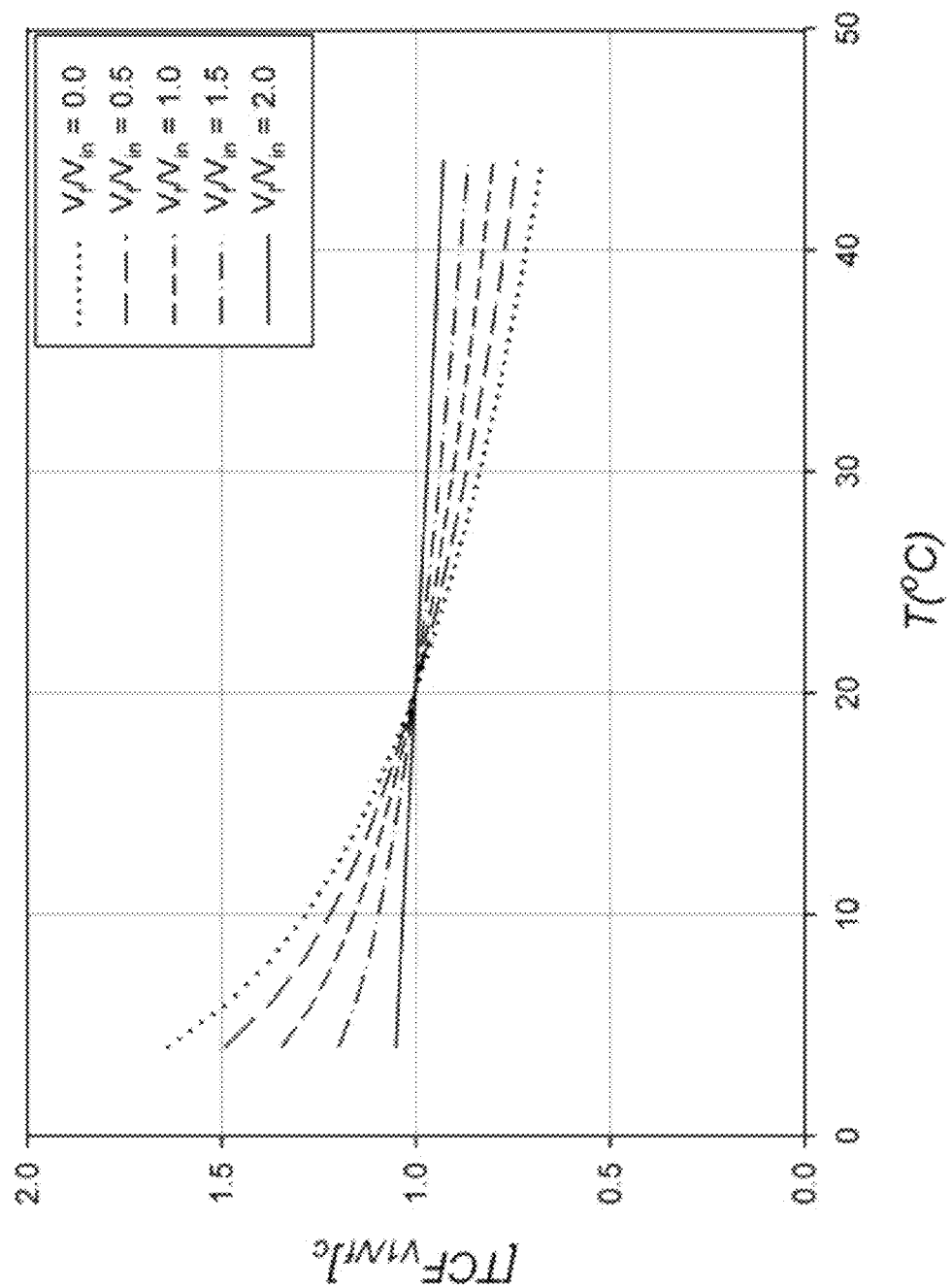
Figures 3, 4, 5, 6, 7, 8, 8A:
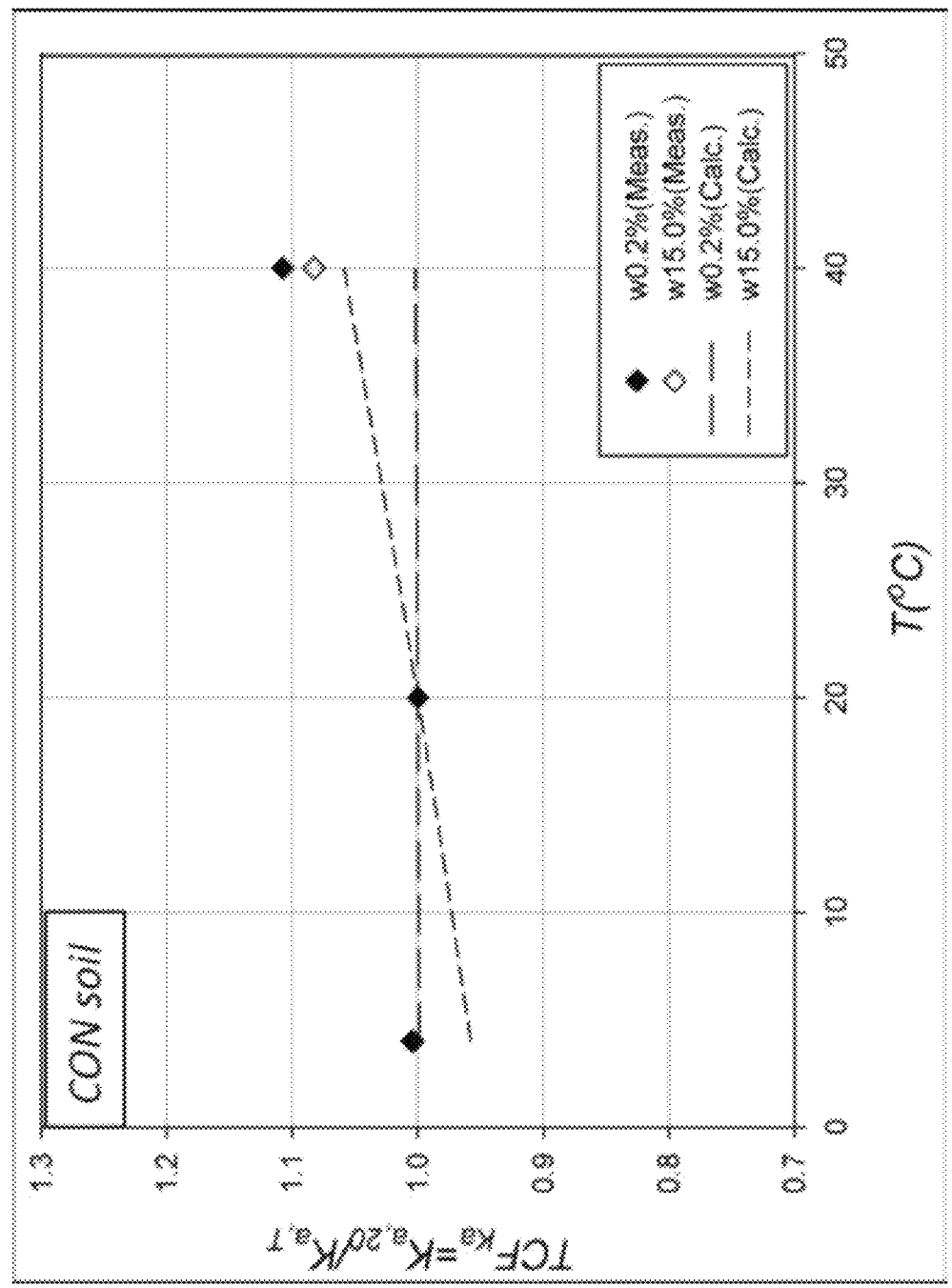
Figures 3, 4, 5, 6, 7, 8, 8B:
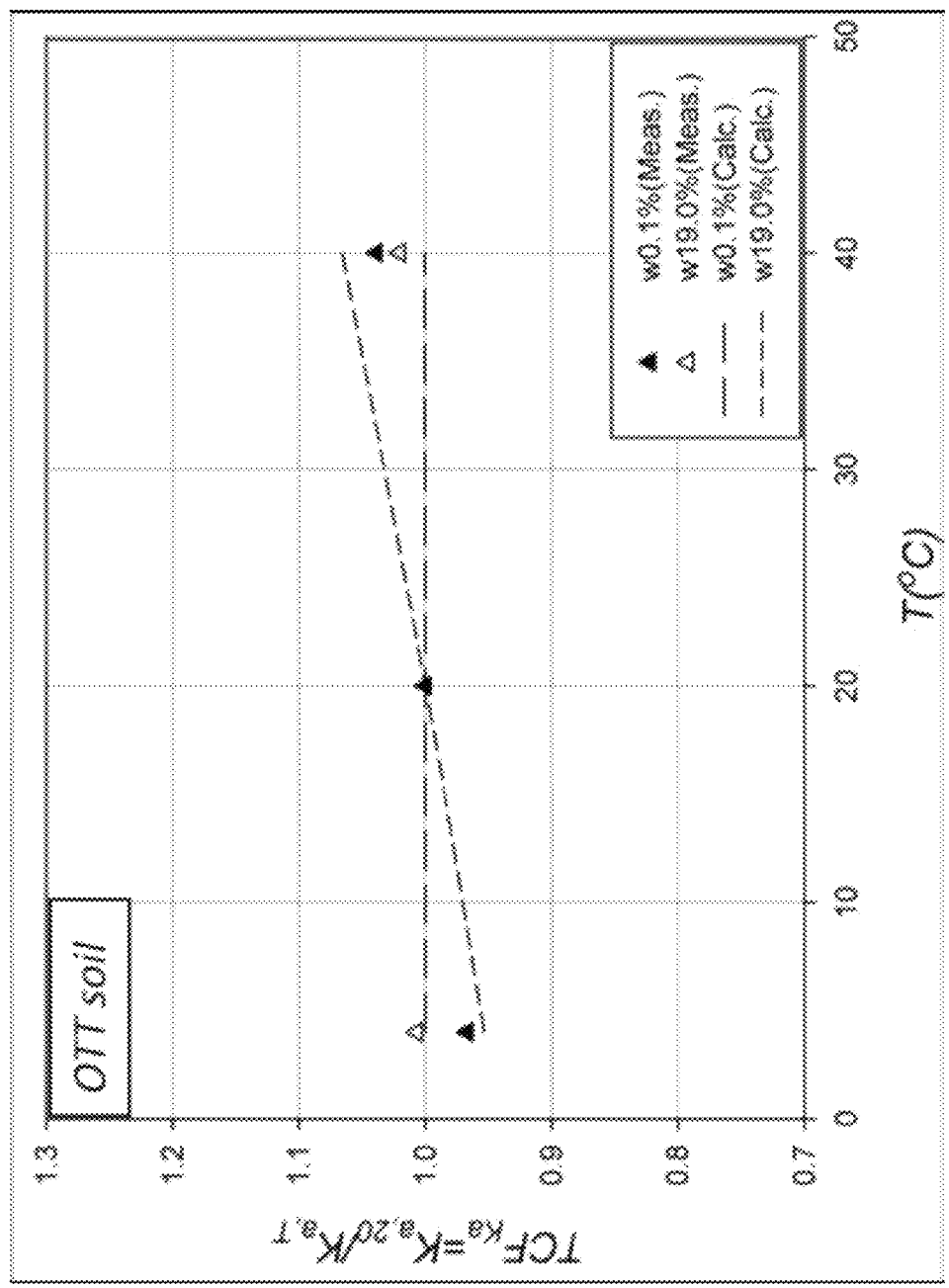
Figures 3, 4, 5, 6, 7, 8, 8C:
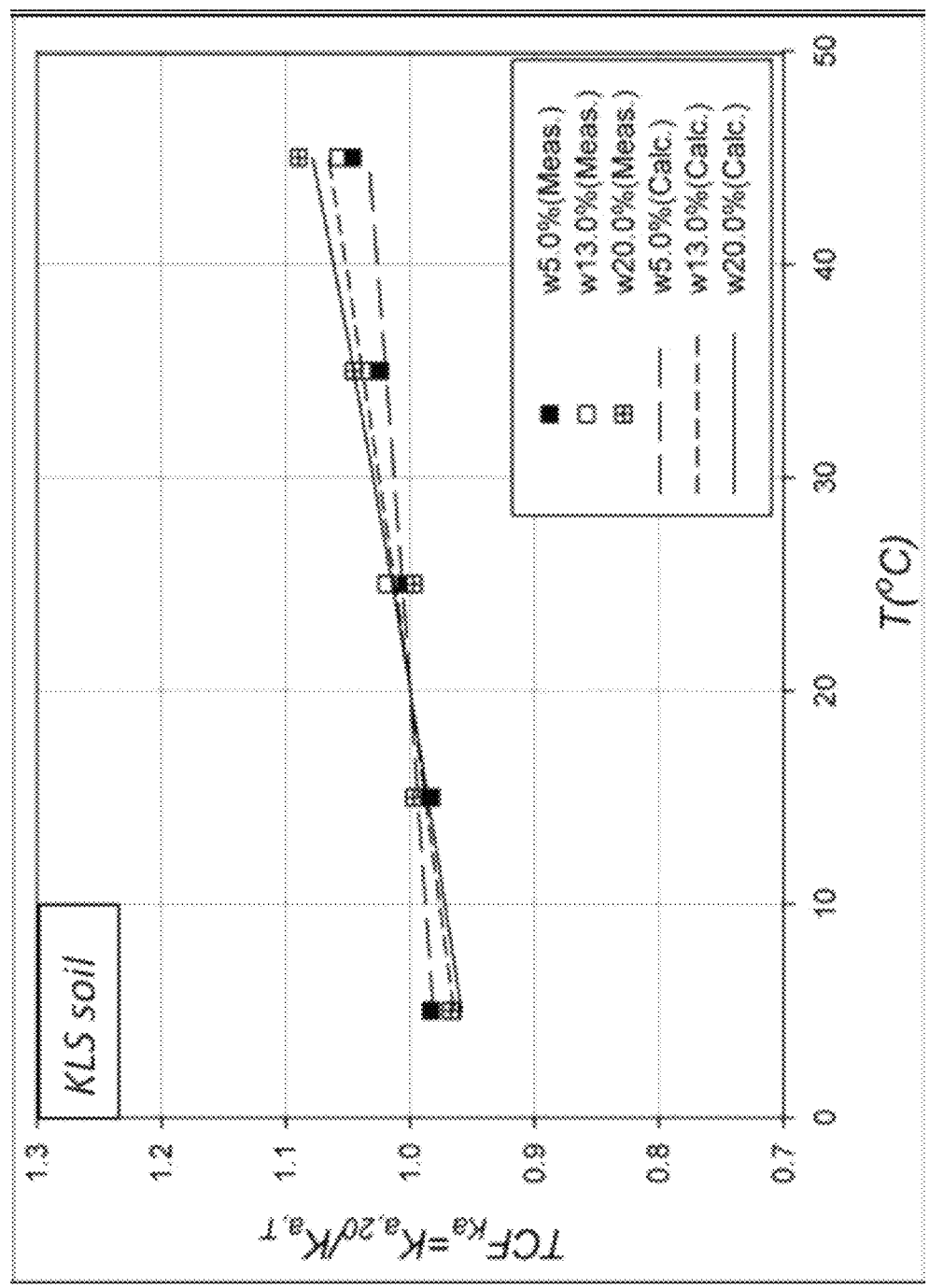
Figures 3, 4, 5, 6, 7, 8, 8D:
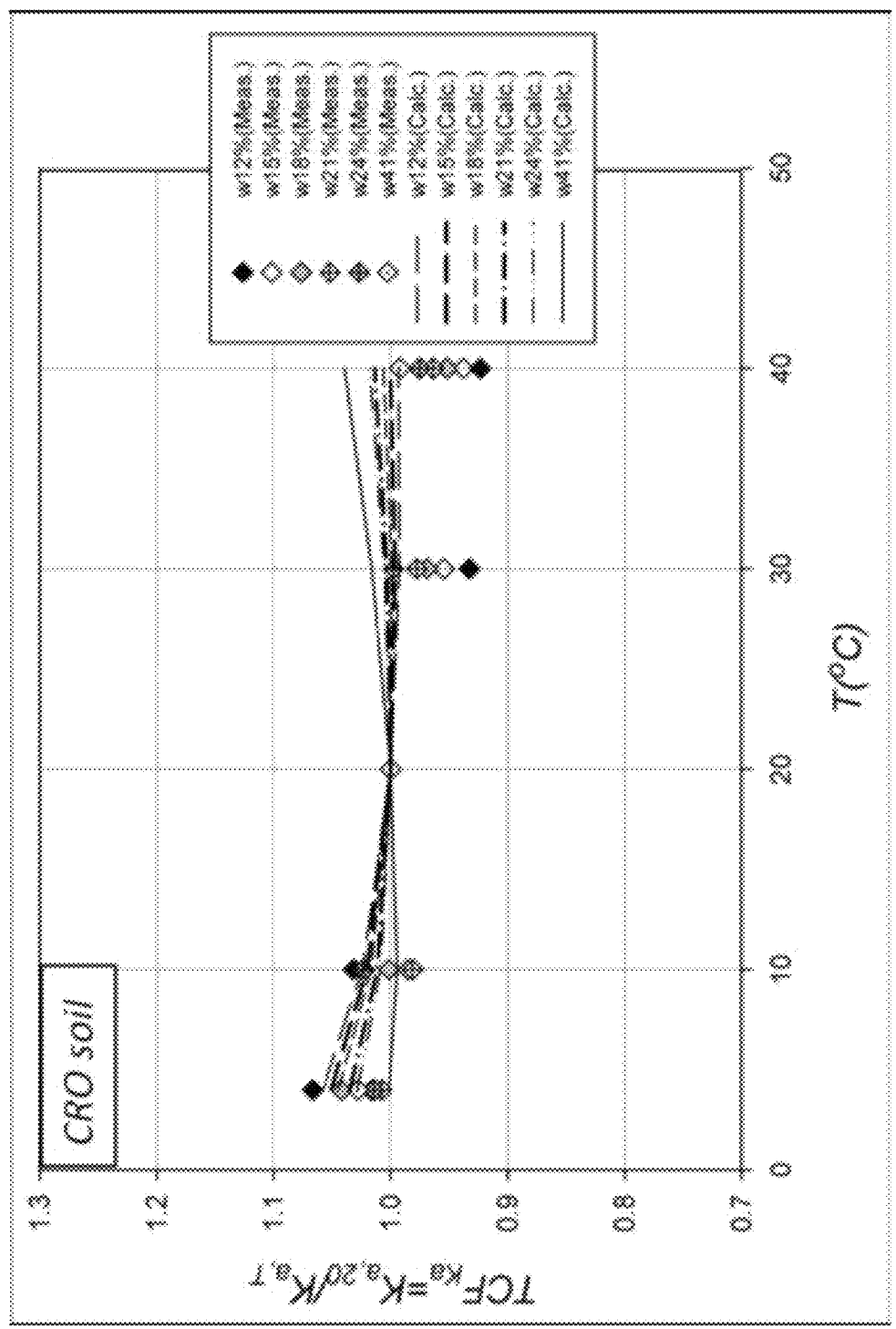
Figures 3, 4, 5, 6, 7, 8, 8E:
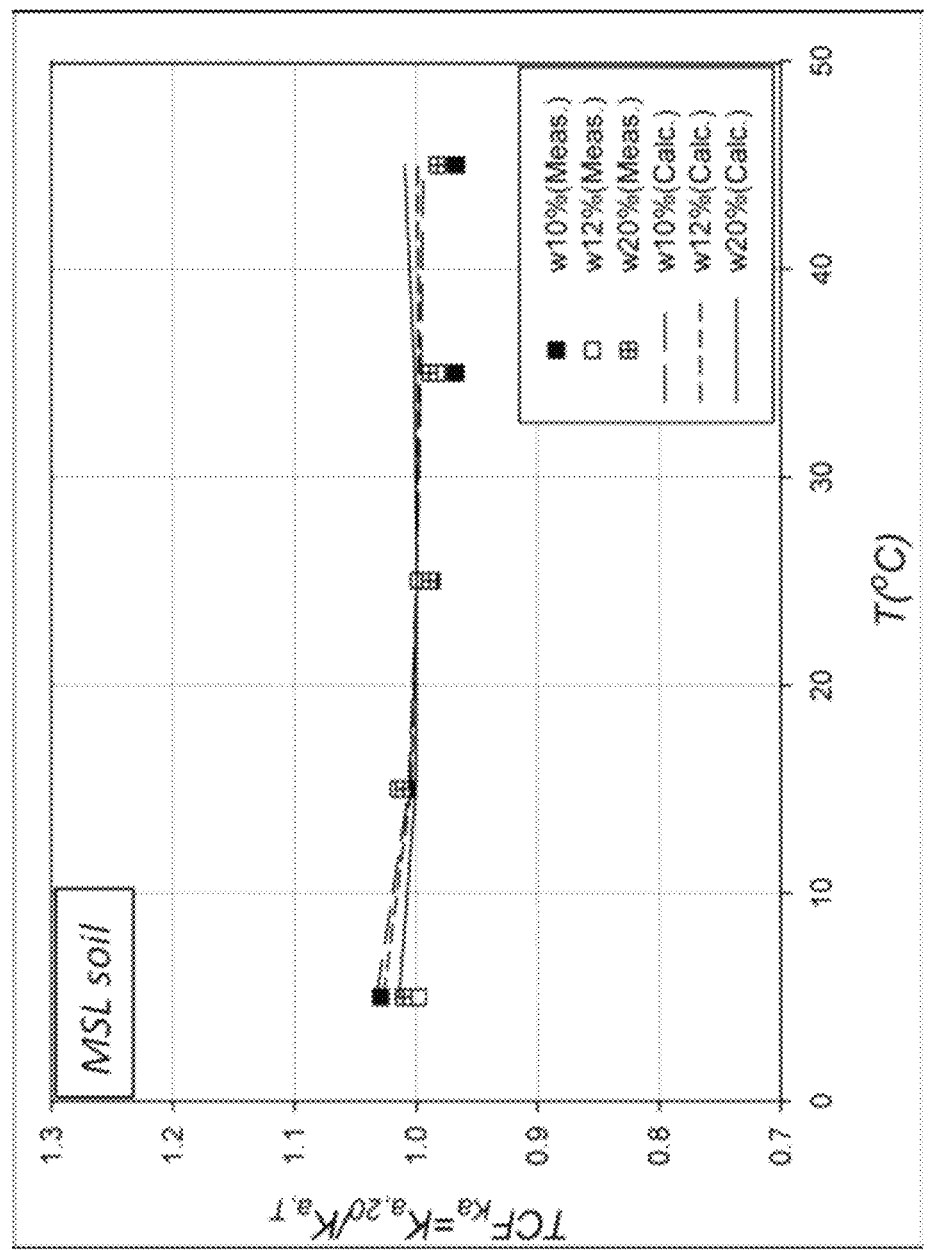
Figures 3, 4, 5, 6, 7, 8, 8F:
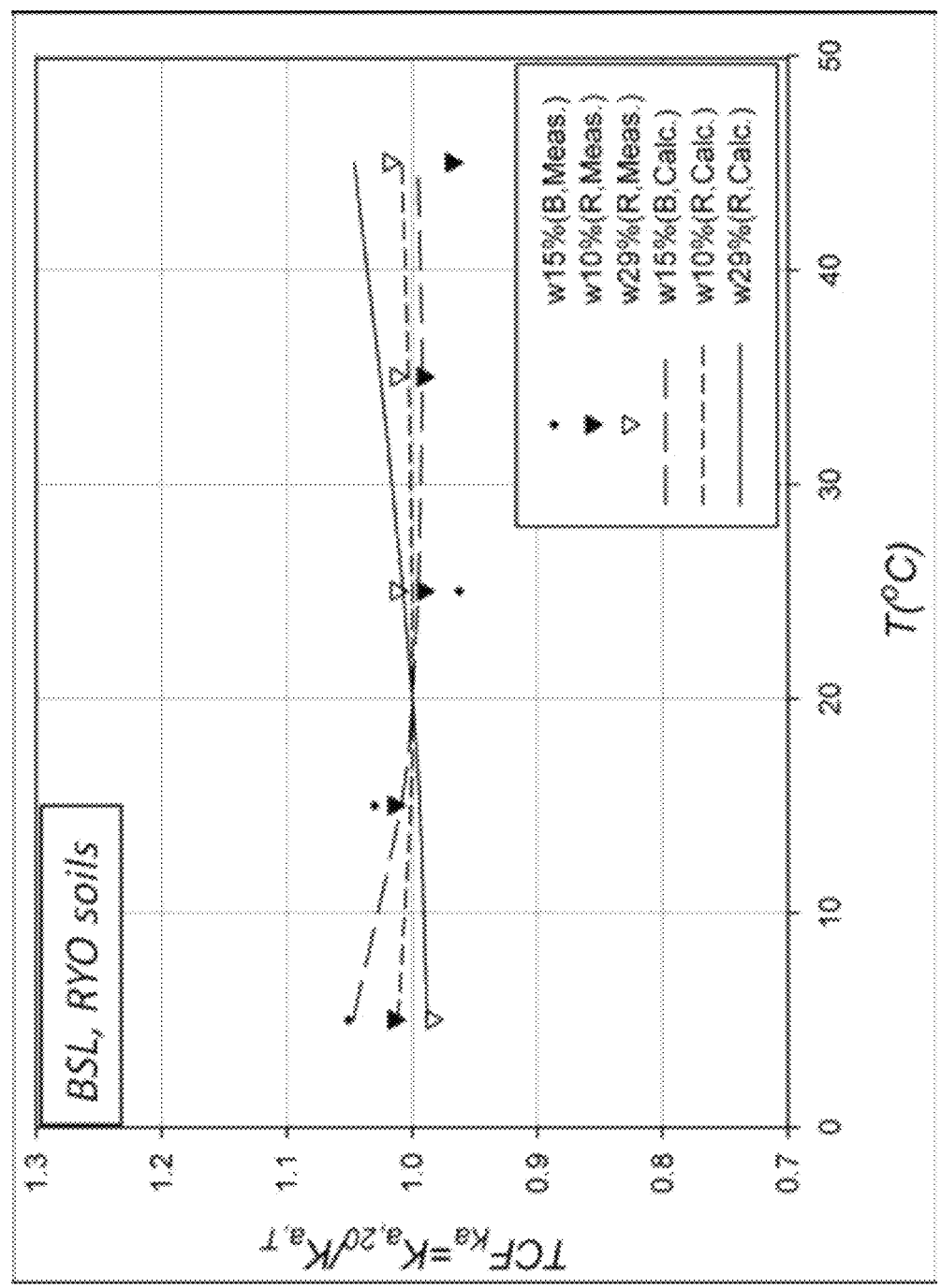
Figures 3, 4, 5, 6, 7, 8, 9, 9A:
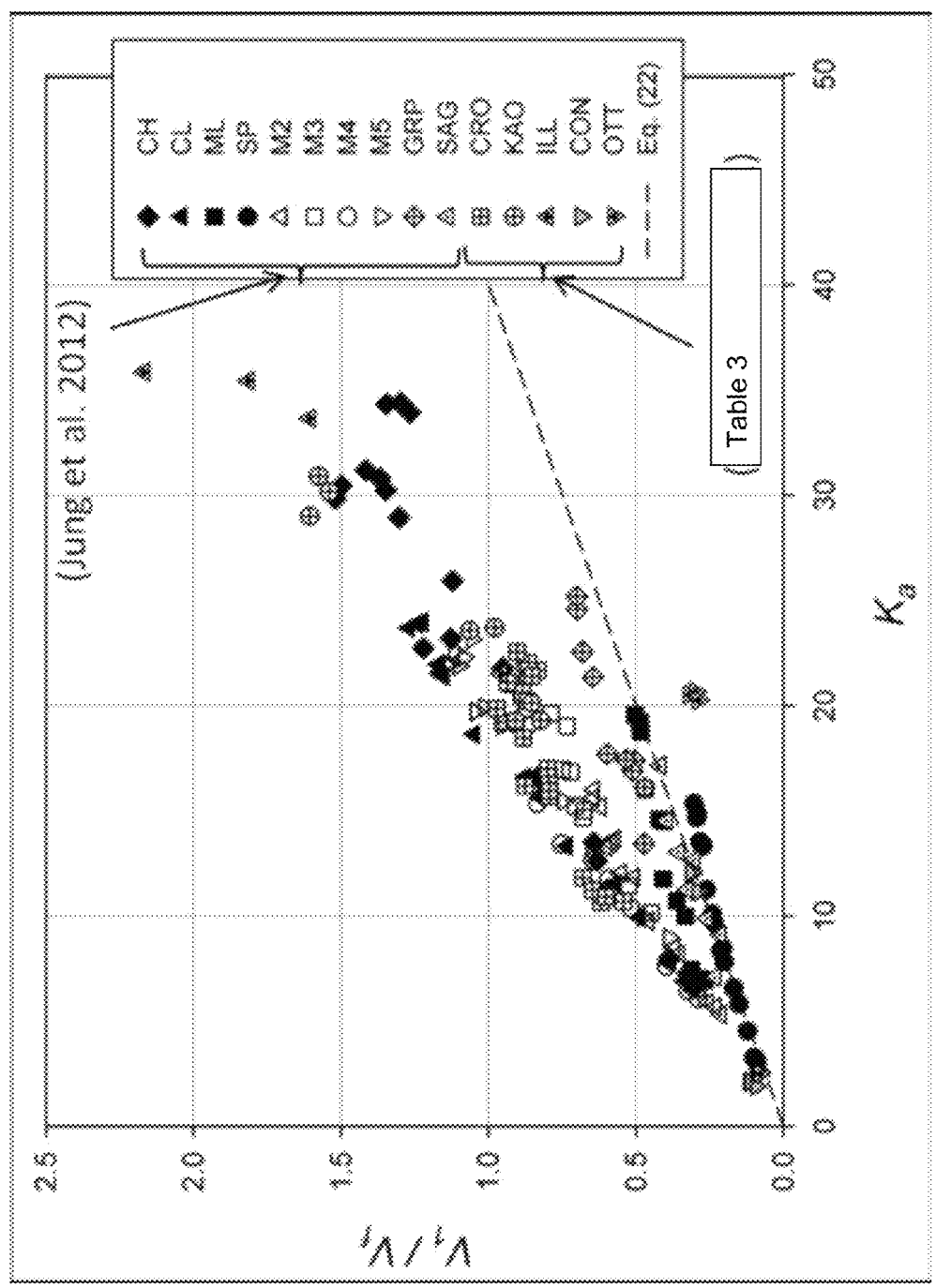
Figures 3, 4, 5, 6, 7, 8, 9, 9B:
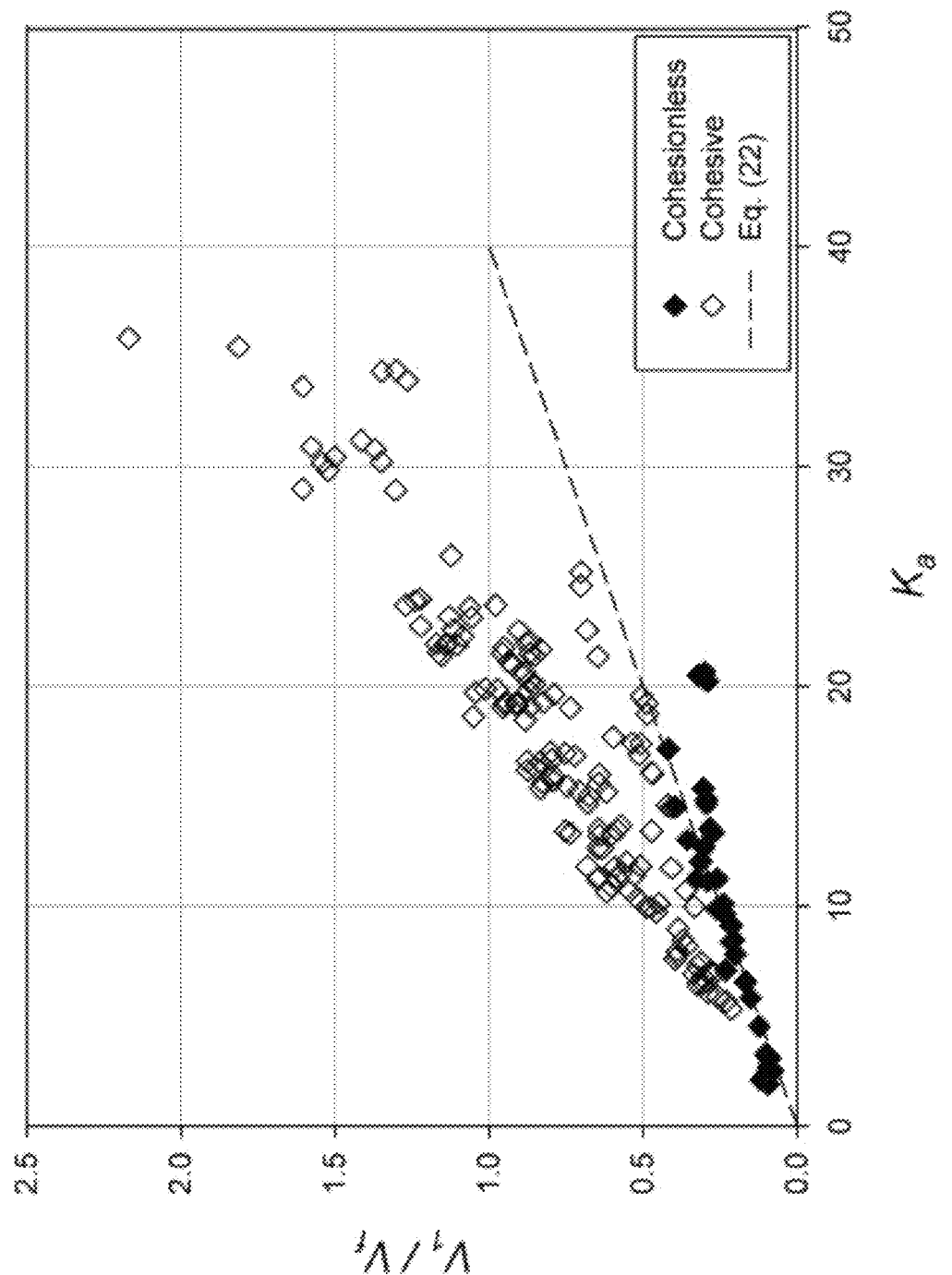
Figures 3, 4, 5, 6, 7, 8, 9, 10, 10A:
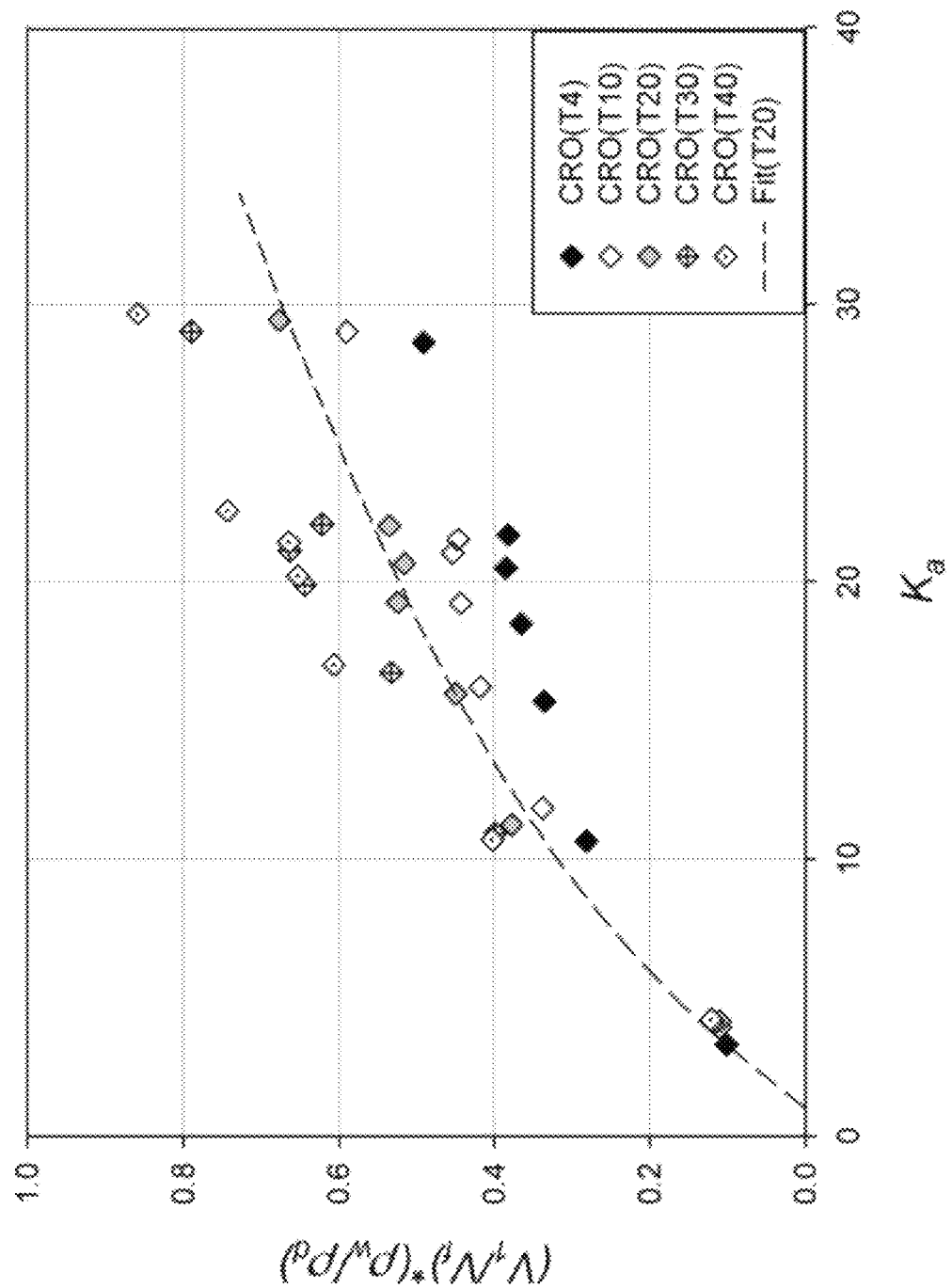
Figures 3, 4, 5, 6, 7, 8, 9, 10, 10B:
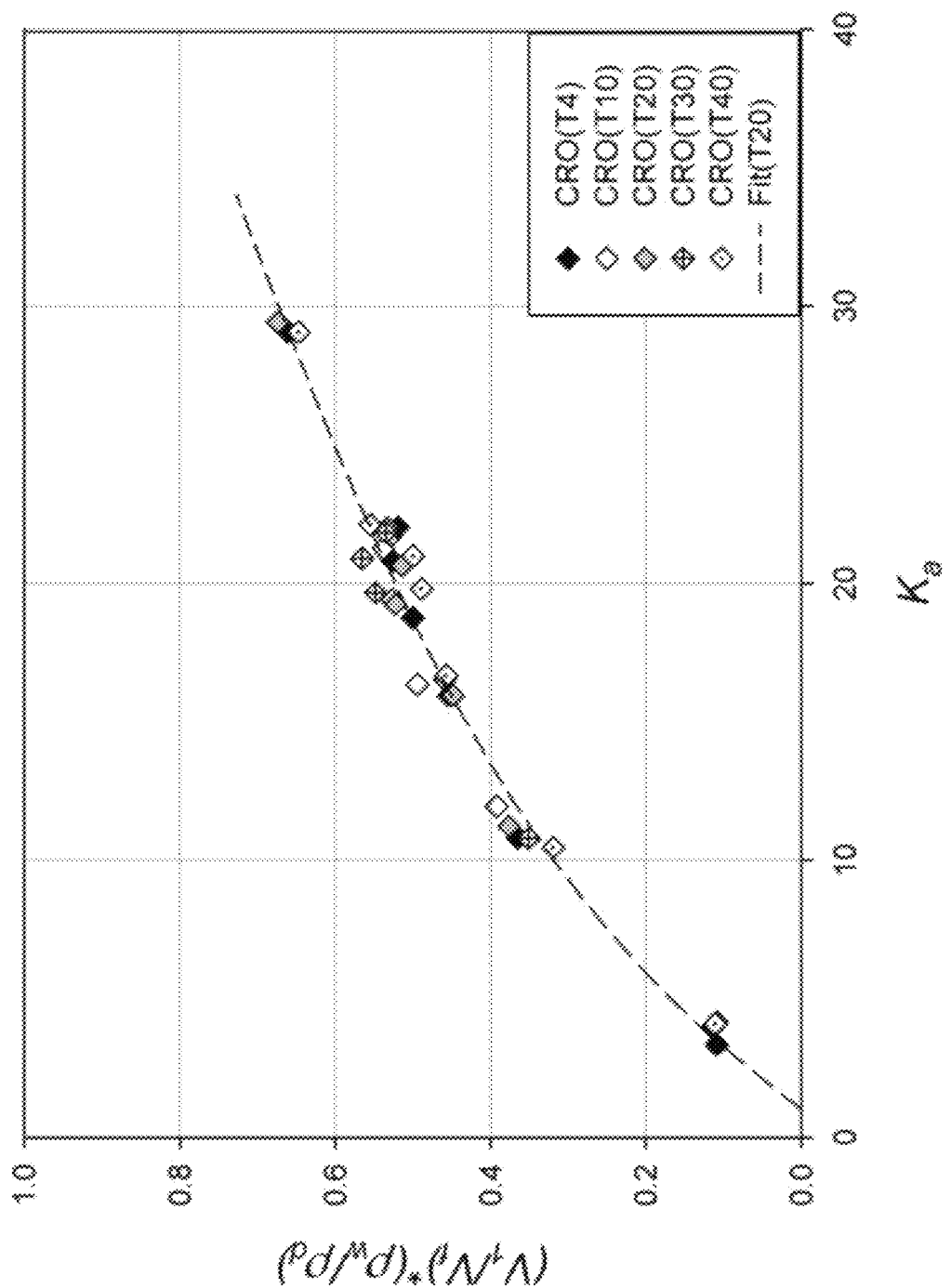
Figures 3, 4, 5, 6, 7, 8, 9, 10, 11, 11A:
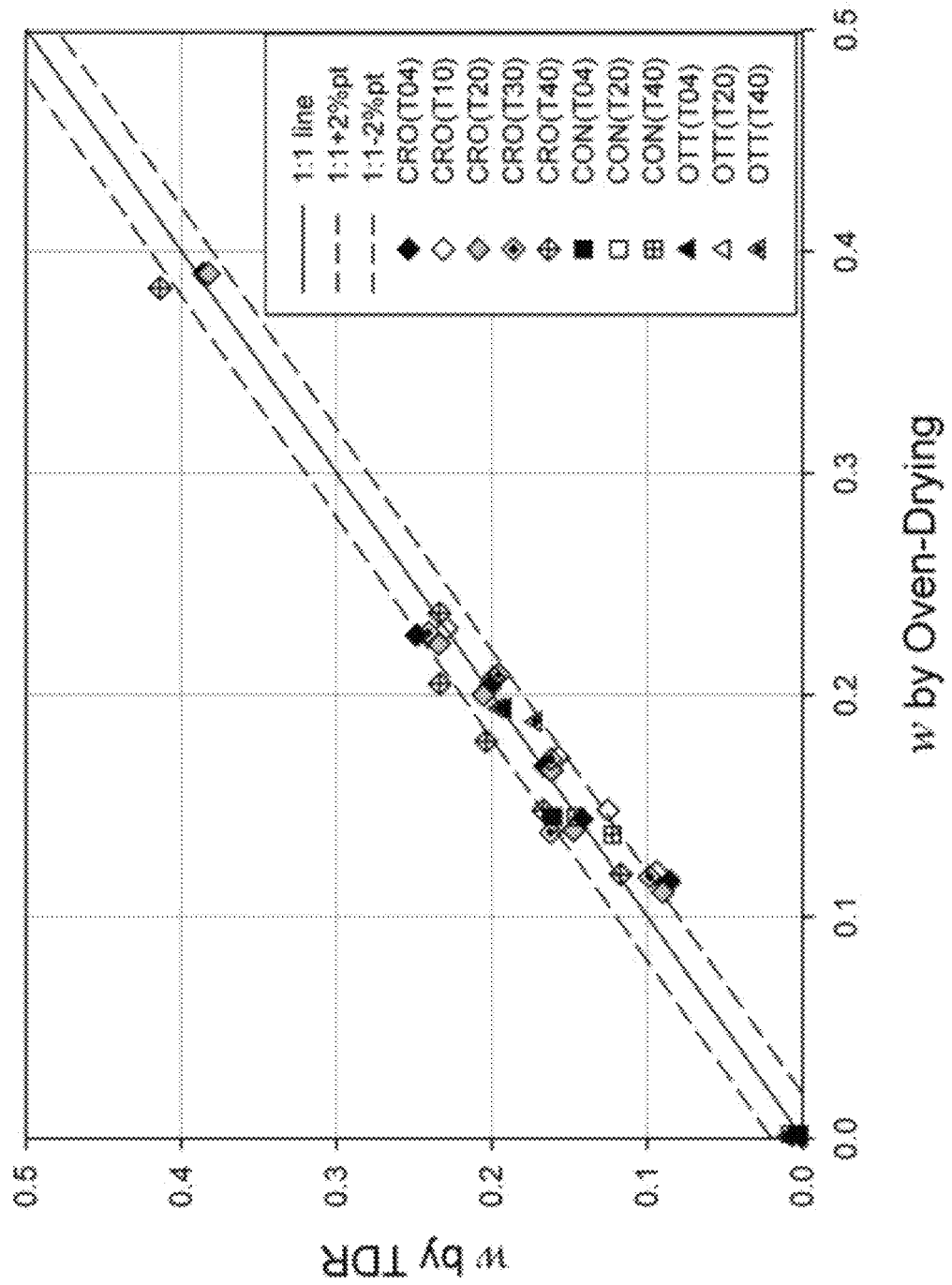
Figures 3, 4, 5, 6, 7, 8, 9, 10, 11, 11B:
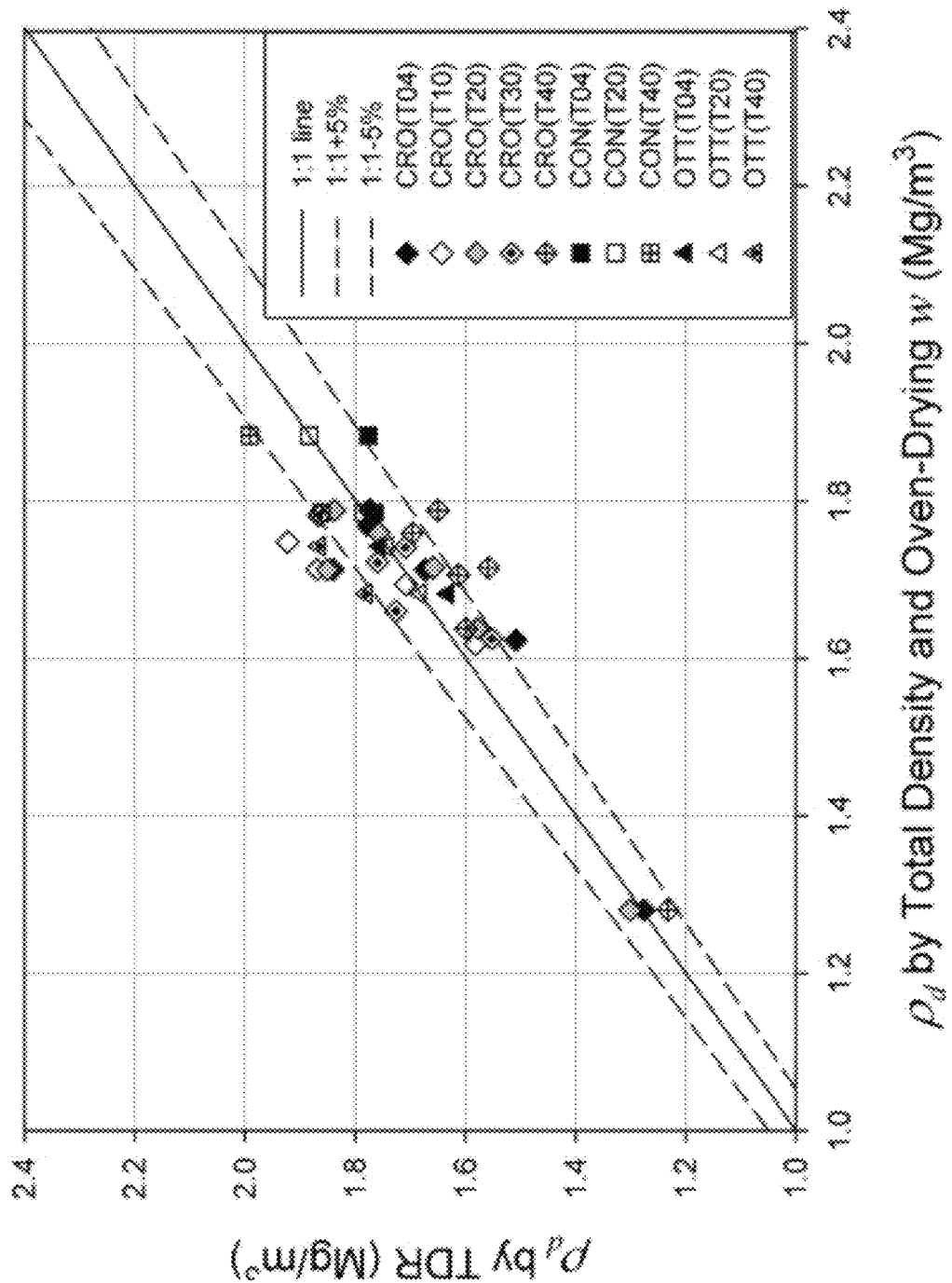

The TDR-measured parameter, $V_1$, (See FIGS. 1-2(b) and (c)) is utilized in the new method presented in this document. From the preliminary test results with ASTM Reference Soils, it is hypothesized that: 1) since $V_1$ and $V_f$ detect different compaction energy at constant w by investigating TDR waveforms, a relationship utilizing $V_1/V_f$ would properly characterize compaction behavior; 2) since a new calibration equation should be independent of compaction energy, and $V_1/V_f$ and $K_a$ are independent of compaction energy, they should be utilized in a new calibration equation.

ASTM Reference Soils were used in order to establish an experimental data set for developing the new calibration equations. Three sets of compaction tests were performed on these four soils as part of this research: Standard Compaction (SC) test, Modified Compaction (MC) test, and Reduced Compaction (RC) test. This last set of tests (RC) had compaction energy of 60% of standard compaction. The results for these compaction tests on CH soils are shown in FIG. 1-2 where MC data points are denoted by the solid squares, SC data points by the solid diamonds, and RC data points by the solid triangles. When the data for three sets of compaction tests were obtained, corresponding TDR waveforms were compared at two selected water contents. FIG. 1-2(a) presents three compaction tests data for ASTM CH soil, and FIG. 1-2(b) and FIG. 1-2(c) show corresponding TDR waveforms at water contents of 10% and 20%, respectively. The TDR waveforms for RC are denoted by dashed lines, SC by solid lines, and MC by dashed lines, shown in FIG. 1-2(*b*) and FIG. 1-2(*c*).

In FIGS. 1-2(*b*) and (*c*), the first peak marked by A is associated with a positive reflection caused by the impedance mismatch at the soil surface. The waveform of the TDR wave energy not reflected at the soil surface passes through the soil probe and is reflected by the impedance mismatch at the end of the probe. The first arrival of this reflected wave is marked by B in FIGS. 1-2(*b*) and (*c*). The TDR waveforms beyond B represent the subsequent travels of the wave through the probe, and include multiple reflections of the wave in the probe. The voltage drop between the peak and the trough of the signal is defined as $V_1$, and termed as "first voltage drop."

FIG. 1-3 represents analysis of $V_1$. FIGS. 1-3(*a*) shows configuration of cylindrical mold probe with a cable, probe head and soils in the mold. The interfaces of cable and head, head and air gap, air gap and soil surface, and probe end are denoted by $t_1$, $t_2$, $t_3$ and $t_4$, respectively. FIGS. 1-3(*b*) and (*c*) represent the zoomed-in plots of TDR waveforms between A and B for ASTM CH soils at 10% of water contents (in FIG. 1-2(*c*) with SC tests), and for deionized (DI) water, respectively. The reflections of TDR waveforms at corresponding interfaces are denoted by $t_1$ through $t_4$, shown in FIGS. 1-3(*b*) and (*c*). Due to small length of air gap, the reflections of TDR waveforms at $t_2$ and $t_3$ in FIGS. 1-3(*b*) and (*c*) look similar, but it has shown by analysis of TDR waveforms with extended length of air gap, that the reflection at $t_3$ is distinct from the one at $t_2$. The reflection at $t_3$ in FIGS. 1-3(*b*) and (*c*) corresponds to A (marked by red arrow) and indicates the start of the reflected wave at soil surface. On the other hand, the reflection at $t_3'$ in FIGS. 1-3(*b*) and (*c*) indicates the end of the reflected wave at soil surface. Analogously, the reflections at $t_4$ (corresponding to B) and $t_4'$ (corresponding to inflection point) indicate the start and end of the reflected wave at the end of the probe. Soils with low electrical conductivity and high relaxation frequency (such as sandy and silty soils) and deionized water (FIG. 1-3(*c*)) show a well-defined inflection point (reflection at $t_4'$), however clayey soils do not have one, shown in FIG. 1-3(*b*), due to high electrical conductivity and low relaxation frequency.

Thus, $V_1$ indicates the transient electromagnetic response of the first reflected wave from the end of the soil specimen. The total wave propagation includes multiple reflections, dielectric dispersion, and attenuation due to the conductive loss and cable resistance in a nonuniform and dispersive TDR system. In contrast, $V_f$ indicates the long-term electromagnetic response of the TDR system, i.e., when the reflected TDR waveform is finally stabilized. It is used with known techniques to calculate the bulk D.C. electrical conductivity, $EC_b$ of the soil.

Those skilled in the art will appreciate how several factors, such as soil types, water content, temperature, pore fluid conductivities (salinities) and TDR probe design, affect TDR waveforms, resulting in changes in $K_a$ and $EC_b$ measurements. Some have studied the influence of soil properties on TDR waveforms, showing that changes in $V_1/V_f$ are proportional to changes in dry densities (corresponding to compaction energy levels) and water contents. Another studied effects of probe geometry by the use of finite difference method and finite element method, and effects of temperature on TDR waveforms. Still another concluded that values of $EC_b$ measured by Purdue TDR field tests are approximately 80% smaller than the ones measured by Purdue TDR laboratory tests, due to different probe geometry. $K_a$ and $EC_b$ can be corrected by temperature correcting factor depending on whether the soils are cohesionless or cohesive.

The TDR waveforms beyond the first peak marked by A in FIG. 1-2 would be different depending on soil type, water content, dry density, temperature, pore fluid conductivity of the soil tested and probe geometry. Therefore, it was hypothesized that the ratio of $V_1$ to $V_f$ multiplied by the ratio of water density to soil dry density may be able to remove the effects of compaction energy, temperature and pore fluid conductivity of soil and probe geometry in TDR testing. This method is termed as "voltage and density normalization method" since $V_1$ is normalized by $V_f$ and $\rho_d$ is normalized by $\rho_w$.

FIG. 1-4 provides a plot of $$\frac{V_1}{V_f}$$

multiplied by the ratio of water density to soil dry density $$\left(\text{i.e., } \frac{V_1}{V_f} \cdot \frac{\rho_w}{\rho_d}\right)$$

versus $K_a$ for ASTM CH Reference Soil with MC, SC, and RC tests, where MC data points are denoted by the solid squares, SC data points by the solid diamonds, and RC data points by the solid triangles. The fitted line considers the following:

1. The y-axis value should be zero at $K_a=1$ which is the minimum possible value of $K_a$ (value in a vacuum). For a vacuum, $V_1$ becomes zero.
2. The y-axis value should increase with increases in $K_a$ (e.g. $K_a=81$ where there is only deionized water at room temperature), depending on pore fluid conductivity. Although the empirical value of $V_1/V_f$ for deionized water at room temperature is approximately 0.4, $\rho_d$ becomes zero (see Equation (1-8)), leading to large y-axis value.
3. Only SC data is used to obtain calibration coefficients.

Based on observation of FIG. 1-4, new calibration equation is introduced as:

$$\frac{V_1}{V_f} \frac{\rho_w}{\rho_d} = c_1 + d_1(K_a - 1) - c_1 \cdot \exp[-f_1(K_a - 1)] \qquad (1\text{-}9)$$

where $c_1$, $d_1$ and $f_1$ are soil-type dependent calibration coefficients. The coefficients with the subscript "1" denote different calibration coefficients from those in the Purdue One-step method (Equations (1-2) and (1-3)). Note that $c_1$, $d_1$ and $f_1$ can be obtained from TDR calibration tests with only soil at Standard Compaction (SC).

Most implementations of this voltage and density normalization method have the following merits over the calibration equations in the Purdue One-step method: 1) $EC_b$ is not coupled with $K_a$, 2) $V_1$ and $V_f$ are measurable, even in cases of highly conductive soils, and 3) calibration coefficients obtained from controlled laboratory environment can be applied to calibration equations for uncontrolled field environment.

Once $c_1$, $d_1$ and $f_1$ are determined and $V_1$, $V_f$ and $K_a$ are measured from TDR tests, dry density, $\rho_d$, can be directly obtained from Equation (1-10). This is an improvement over the existing Purdue One-step method. Equation (1-9), solved for $\rho_d$, becomes:

$$\rho_d = \frac{\frac{V_1}{V_f}\rho_w}{c_1 + d_1(K_a - 1) - c_1 \cdot \exp[-f_1(K_a - 1)]} \quad (1\text{-}10)$$

Once $\rho_d$ is obtained, Equation (1-1) can be solved for w, as follows:

$$w = \frac{1}{b}\left(\sqrt{K_a}\frac{\rho_w}{\rho_d} - a\right) \quad (1\text{-}11)$$

FIG. 1-5 shows the determination of $\rho_d$ from TDR measurements using Equation (1-10) compared with $\rho_d$ by direct measurements of moist density and oven-drying w for ASTM CH soils with three different compaction energy levels.

Dry density values for MC, SC and RC data points by Equation (1-10) in FIG. 1-5 are denoted by the solid squares, solid diamonds, and solid triangles, respectively. The results for the same MC, SC and RC data analyzed by the existing Purdue One-step method (Equation (1-5)) are denoted by "X". The data from the new calibration equation (Equation (1-10)) show an improvement over the Purdue One-step method and generally lie within ±5% of the 1:1 line for the majority of the data points. The two outliers have coordinates (1.7, 1.5) from MC and (1.4, 1.2) from RC. The error causing these outliers may be attributed to the following reasons. First, this error may be from $K_a$ determination by TDR test. In the compaction curve, which will be shown in FIG. 1-7, these two data points indicate one from dry of optimum for MC and another from dry of optimum for RC. It has been reported that $K_a$ determination is extremely sensitive to the presence of air gaps of soils surrounding a center rod. Unfortunately, a few cracks tend to form around a center rod when the rod was driven into cylindrical mold during TDR tests, because specimens are very hard when compacted soils are on the dry side of optimum. Second, although $K_a$, $$\sqrt{K_a}\frac{\rho_w}{\rho_d}$$

and $$\frac{V_1}{V_f}\frac{\rho_w}{\rho_d}$$

in Equations (1-1), (1-11) and (1-10) are relatively independent of compaction energy levels, the results of ASTM CH soils with different compaction energy levels have the lowest R-squared values from the fitted calibration equations compared with R-squared values from the results of other ASTM Reference Soils. In other words, engineering properties of compacted fine-grained (or cohesive) soils are greatly affected by the compaction method, the compactive effort applied, the soil type and water content.

Determination of w from TDR measurements and Equation (1-11) is compared with w by direct measurements (oven-drying) for ASTM CH soils with three different compaction levels, shown in FIG. 1-6, where SC, RC, and MC data points are denoted by the solid diamonds, solid triangles, and solid squares, respectively. The results of SC, RC, and MC data by Equation (1-4) (the Purdue One-step method) are also denoted by "X", shown in FIG. 1-6.

The results from the new calibration equation, Equation (1-11), often lie within line ±2 percentage points of the 1:1 line, providing an improvement over water content determination by the Purdue One-step method (Equation 1-4).

The data in FIGS. 1-5 and 1-6 are compared and placed together in FIG. 1-7, where SC, RC, and MC data points determined by TDR are denoted by the solid diamonds, solid triangles, and solid squares, respectively. The SC, RC, and MC data points by direct measurement and oven-drying method are denoted by the hollow diamonds, hollow triangles, and hollow squares with the dashed lines, respectively.

Note that when the soil specimens are compacted at lower water content than optimum water content, the difference between the results by TDR and the ones by direct measurement are larger. This indicates that the methodology maybe improved by choosing a more narrow range of water contents near the optimum value.

This section explains a revised process of determining the first and second reflection points, as implemented in analyzing the test data described herein.

The first and second reflection points are denoted by A and B in FIG. 1-2. The process of finding point A starts with identifying a range of TDR data where the first reflection point is likely to occur and the point with maximum y value in this region is selected. Select 5 to 11 points near the maximum point sufficient to define the peak, with approximately half of the points on the left and right of the maximum point. A second-order polynomial equation is fitted to the points, as shown in FIG. 1-8. Then the maximum y value from the second order polynomial equation is analytically determined as the first peak point, denoted by A.

Once the first reflection point is determined, a range of TDR waveform values after the first reflection point is defined and the point with minimum y-axis value is selected. Select 17 to 67 points, depending on their spacing, near the minimum point that describe the trough in the data, with half of the points on the left and right of the minimum point. A compound, hybrid arc tangent function was found to have properties for best fitting the curve:

$$V_{calc} = g_1 + g_2 \cdot \frac{2}{\pi}\mathrm{atan}(g_3 \cdot x^{g_4}) + g_5 \cdot \frac{2}{\pi}\mathrm{atan}(g_6 + g_7 \cdot x) \quad (1\text{-}12)$$

where $V_{calc}$ denotes y-axis values of fitted TDR waveform, $g_1$ through $g_7$ denote fitting coefficients, and x denote x-axis values of fitted TDR waveform. Equation (1-12) is fitted to 67 points and the second reflection point denoted by B is described in FIG. 1-9.

The point of inflection is determined by the point with maximum first derivative in the fitted line. Then, the point of maximum curvature in the fitted line is calculated by the following formulas:

$$Curv_i = \frac{V''_{calc,i}}{[1 + (V'_{calc,i})^2]^{1.5}} \quad (1\text{-}13)$$

$$V'_{calc,i} = \frac{V_{calc,i+1} - V_{calc,i}}{x_{i+1} - x_i} \quad (1\text{-}14)$$

$$V''_{calc,i} = \frac{V'_{calc,i+1} - V'_{calc,i}}{x_{i+1} - x_i} \quad (1-15)$$

where the subscript "i" denotes the number of x-axis values in the fitted line.

The tangent line and horizontal line through the point of maximum curvature are determined, and the bisection line of the two lines is obtained. The intersection point of the bisection line from the maximum curvature point and the tangent line from the point of inflection identifies the second reflection point denoted by B, shown in FIG. 1-9.

Once the first and second reflection points (A and B) are determined, $K_a$ is calculated with difference between x-axis values of points A and B by use of the following formula:

$$K_a = \left(\frac{B-A}{L_p}\right)^2 \quad (1-16)$$

where $L_p$ is the length of the probe inserted into the soil.

Parameter $V_1$ can be obtained from difference between y-axis values of points A and B. This information is then available for the new calibration equation (voltage and density normalization method).

FIG. 1-10 illustrates a method of calculating dry density $\rho_d$ and water content w of soil using the new equations disclosed herein. A plurality of spikes, such as the TDR probes shown in FIG. 3-1 are provided and driven into soil. The spikes are placed in a spaced apart relationship. The probe head is then seated on the spikes in electrical communication therewith. A TDR apparatus is in electrical communication with the probe head. The TDR apparatus applies an electrical signal into the spikes via the probe head and takes a TDR reading therefrom. The TDR signal is analyzed, and values for $K_a$, $V_1$, and $V_f$ are obtained as disclosed herein. $P_d$ and w are then calculated using Equations (1-10) and (1-11). In one embodiment, the TDR signal is analyzed and the calculations are applied using a computer in electronic communication with the TDR apparatus. The equations disclosed herein may be programmed into a computer in a conventional manner. Preferably, the computer is a portable computer, such as a laptop or tablet computer, which can easily be transported to the soil site.

Compaction energy levels for reduced compaction (RC), standard compaction (SC), and modified compaction (MC) are 360, 600, and 2700 kN-m/m$_3$, respectively (ASTM D698 (ASTM 2007c), D1557 (ASTM 2009)). With compaction level in many common engineering applications being unknown, any reliable method for predicting w and $\rho_d$ should perform under different compaction energy levels. FIGS. 2-1(a) and 2-1(b) represent the new calibration equations obtained from best fit of SC tests for low plastic silt (ASTM ML) and poorly graded sand (ASTM SP) soils. They clearly show that the new calibration equations are independent of the compaction energy levels, as the MC and RC data fit well with the fitted lines. In FIG. 2-1(b). The exponential function of Eq. (1-9) works when $K_a$ is low (i.e. low water content). FIGS. 2-1(c) and 2-1(d) demonstrate the performance of the new approach by comparing the predicted w and $\rho_d$ (by Eqs. (1-1) and (1-9)) to direct measurements (by the total density and oven-drying water content). The results of ASTM ML and SP soils by the new calibration equations capture the effects from different compaction energy levels, which is not obtainable by the existing Purdue One step TDR method (Eqs. (1-1), (1-2), and (1-3)).

While the differences between $\rho_d$ results at different w and compaction energies are not large for coarse-grain soils, the TDR measurements for the poorly graded sand (ASTM SP) soil have some limitations. At high water contents, it was observed that some water seeped out of the bottom of the compaction mold since the water that cannot hold within the sand pores tends to move downward due to gravity. Moreover, at low water content, coarse-grained soils create relatively larger porosity surrounding a center probe (in comparison with fine-grained soils), which may lead to inaccurate $K_a$ determination using the One step method. These observations may explain some of the discrepancies between measured and predicted results for ASTM SP soils.

FIG. 2-2(a) shows the results of water content by TDR measurements (Eq. (1-11)) compared with direct measurements (oven-drying (ASTM D2216 (ASTM 2010b))), and FIG. 2-2(b) represents the results of dry density by TDR measurements (Eq. (1-10)) compared with direct measurements (by the total density and water content by oven-drying) for four ASTM Reference Soils and five mixed soils (M soils), each with three different compaction energy levels. The coefficients of the new calibration equations (obtained from SC points only) for ASTM Reference Soils and M soils are presented in Table 1 below.

TABLE 1

Summary of New Calibration Coefficients

| Soil | a | b | R$^2$ (Eq. (1)) | c$_1$ | d$_1$ | f$_1$ | R$^2$ (Eq. (9)) |
|---|---|---|---|---|---|---|---|
| CH | 1.236 | 9.145 | 0.973 | 0.098 | 0.028 | 0.988 | 0.981 |
| CL | 1.066 | 8.829 | 0.990 | 0.002 | 0.033 | 0.993 | 0.993 |
| ML | 1.061 | 8.656 | 0.994 | 0.131 | 0.009 | 0.987 | 0.992 |
| SP | 0.921 | 8.565 | 0.995 | 0.077 | 0.007 | 0.298 | 0.983 |
| GRP | 1.151 | 8.003 | 0.990 | 0.117 | 0.015 | 0.999 | 0.948 |
| SAG | 0.906 | 8.517 | 0.992 | 0.059 | 0.010 | 0.985 | 0.981 |
| M1 | 0.933 | 8.009 | 0.975 | 0.032 | 0.018 | 0.962 | 0.989 |
| M2 | 0.992 | 7.735 | 0.986 | 0.032 | 0.020 | 0.953 | 0.995 |
| M3 | 1.013 | 8.163 | 0.990 | 0.069 | 0.020 | 0.978 | 0.986 |
| M4 | 1.054 | 8.022 | 0.990 | 0.077 | 0.023 | 0.966 | 0.980 |
| M5 | 1.237 | 7.366 | 0.974 | 0.018 | 0.031 | 0.998 | 0.992 |
| CCO | 1.103 | 7.483 | 0.951 | 0.014 | 0.024 | 0.999 | 0.956 |
| VHS | 1.052 | 7.894 | 0.886 | 0.036 | 0.004 | 0.240 | 0.985 |

R$^2$ values for Eq. (1) and Eq. (9) refer to Equations (1-1) and (1-9), respectively.

The results of water content generally lie within the 1:1 line ±2% point of water content, and those of dry density lie within the 1:1 line ±5% (of measured value). For water content (FIG. 2-2(a)), this result was fairly consistent for the majority of the data points from the dry side of optimum for ASTM CH soils. For dry density, a few outliers in FIG. 2-2(b) may be attributed to the following reasons. First, some error may arise from $K_a$ determination in the dry side of optimum water content due to the formation of a few cracks around the cylindrical mold probe when the solid rod was driven into the very hard soil specimen. FIG. 2-3 shows an example of the cracks adjacent to the cylindrical mold probe, for ASTM CH soils at 15% of water content.

Second, although TDR-measured $V_1/V_f$ and $K_a$ in Eqs. (1-1) and (1-9) are relatively independent of compaction energy levels, the high percentage and plastic nature of the ASTM CH soils may have resulted in a comparatively small dependency on compaction. This was shown by comparing the R-squared values from the fitted calibration equations of ASTM CH soils to the R-squared values from the other ASTM Reference Soils, shown in Table 1. Comparison showed that the ASTM CH soils have the lowest R-squared values among the other ASTM Reference Soils. In other words, it indicates that engineering properties of compacted fine-grained soils are more affected by the compaction method, the compactive effort applied, the soil type and water content.

The proposed calibration equations (Eqs. (1-1) and (1-9)) according to some embodiments use a variety of field testing results, and check whether calibration coefficients obtained from controlled laboratory tests can be applied to the field by considering different conditions from compaction energy, temperature, pore fluid conductivity and probe configuration. A "non-engineered" field denotes a field testing site with no compaction by geotechnical engineering methods, and an "engineered" field denotes a field testing site on an active construction compacted by geotechnical engineering methods. Four field testing sites were analyzed, two non-engineered (GRP and SAG soils) and two engineered field sites (CCO and VHS soils). GRP and SAG soils represent fine-grained and coarse-grained soils, respectively.

In order to evaluate the TDR test results of GRP and SAG soils, the sand cone (ASTM D1556 (ASTM 2007a)) and oven-drying (ASTM D2216 (ASTM 2010b)) methods were performed. Results of in-situ dry density from sand cone tests were reported as the average of two values obtained at the soil surface and at a depth of 10 cm (4 inches), in order to have the same depth of the soils covered by TDR tests. At each site, multiple field TDR tests (four for GRP and three for SAG soils) were performed adjacent to the two sand cone tests. On the other hand, the TDR test results were evaluated with nuclear gauge tests of CCO soils on an active construction site. Although detailed geotechnical information of the soils and site conditions was not available, the results by TDR tests were compared with the ones by nuclear gauge tests at the same test station. Lastly, the TDR and nuclear gauge tests of VHS soils were performed on an active construction site. Although the number of tests performed at the VHS test stations were different (five TDR tests, two nuclear gauge tests), the results by TDR tests were compared with the ones by nuclear gauge tests at adjacent test station. VHS soils contain large size particles which are frequently used as bases and subbases in highway construction. The engineering properties of these soils are given in Table 2 below:

TABLE 2

Properties of Soils

| Soil | USCS | Max. particle size (mm) | Finer than #200 (%) | LL | PI | Gs |
|------|------|-------------------------|---------------------|------|-------|------|
| CH | CH | 0.1 | 98.8 | 59.8 | 39.2 | 2.72 |
| CL | CL | 0.1 | 88.5 | 33.4 | 13.6 | 2.67 |
| ML | ML | 0.1 | 99.0 | 27.4 | 4.1 | 2.73 |
| SP | SP | 4.75 | 1.0 | — | N.P.[1] | 2.66 |
| GRP | CL | 4.75 | 88.0 | 31.1 | 15.8 | 2.68 |
| SAG | SM-SW | 10.0 | 25.4 | — | N.P. | 2.72 |
| M1 | SM-SC | 4.75 | 41.3 | — | N.P. | 2.76 |
| M2 | ML | 4.75 | 52.4 | 16.2 | 5.7 | 2.77 |
| M3 | CL | 4.75 | 72.9 | 28.5 | 16.2 | 2.83 |

TABLE 2-continued

Properties of Soils

| Soil | USCS | Max. particle size (mm) | Finer than #200 (%) | LL | PI | Gs |
|------|------|-------------------------|---------------------|------|-------|------|
| M4 | CL | 4.75 | 78.6 | 33.7 | 14.8 | 2.83 |
| M5 | CL | 4.75 | 84.4 | 41.0 | 21.1 | 2.82 |
| CCO | SP[†] | 4.75 | — | — | — | — |
| VHS | GW-GM | 25.0 | 8.7 | — | N.P. | — |

Note:
[†]SP for CCO soils is estimated due to the lack of the geotechnical information.
[1]N.P. stands for "non-plastic".

Results from the ASTM Reference Soils and M soils at different compaction energies were used to compare the existing Purdue One-step TDR method (ASTM D6780 (ASTM 2005)) with the new proposed methodology. FIG. 2-4(a) presents the results of water content by TDR measurements using (i) the Purdue One-step TDR method (Eqs. (1-1), (1-2), and (1-3)) and (ii) the new proposed method (Eqs. (1-1) and (1-9)) compared with direct measurements (oven-drying). Moreover, FIG. 2-4(b) presents the results of dry density by TDR measurements (also for both methods) compared with direct measurements (by the total density and water content by oven-drying). Calibration coefficients for both the Purdue One-step and the new proposed method were determined from standard compaction (SC) tests data only. FIG. 2-4(b) shows outliers from the results of reduced compaction (RC) and modified compaction (MC) using the Purdue One-step TDR method indicating that the Purdue One-step TDR method provides the results similar to the ones of standard compaction (SC). Statistically, the mean absolute error (all soils) for water content using the Purdue One-step TDR method was 0.016 compared to 0.009 using the new proposed method. Moreover, the mean absolute error (all soils) for dry density using the existing Purdue One-step TDR method was 0.089 compared to 0.055 using the new proposed method.

Electromagnetic properties of soils are temperature sensitive and it was useful to establish these effects, especially for the second calibration equation (Eq. (1-9)), which is new, and contains two measured parameters that have not been studied much. Various embodiments provide the improved and simplified temperature correction factors for apparent dielectric constant. It also explored why the temperature correction factors for cohesionless soils are similar, but reduced in magnitude from those for plain water, while those for cohesive soils have an inverse behavior compared to cohesionless soils and plain water. The behavior for cohesive soils is complicated by the presence of bound water associated with clay minerals.

Various other embodiments address the question of when is a soil considered cohesionless for the purpose of applying the temperature correction factors for TDR tests. An automatic method for determining soil type for soil temperature corrections was based on preliminary study with a ratio of two of the new measured parameters, $V_1$, and $V_f$. The automated method could easily be implemented in the data acquisition software and would allow for making temperature corrections without the use of any other information about the soil being tested. This application extends the usefulness of the TDR Method to temperatures from approximately room temperature to a range of temperatures from about 4° C. to about 40° C.

Information on soils for the United Soil Classification System (USCS), liquid limit (LL), plasticity index (PI) based on ASTM D2487 (ASTM 2010a), D422 (ASTM 2007), D4318 (2010c) and estimated specific surface area (SSA) are summarized in Table 3 below:

TABLE 3

Characteristics of Soils with Estimated SSA Values

| Soil | sand (%) | silt (%) | clay (%) | LL | PI | Estimated SSA† (m²/g) | Test range (° C.) | Comments |
|------|----------|----------|----------|----|----|-----------------------|-------------------|----------|
| CRO | 16 | 50 | 34 | 41 | 23 | 86 | 4-40 | Crosby till (CL) |
| KAO | 0 | 0 | 100 | 40 | 16 | 60 | 4-40 | Kaolinite (CL-ML) |
| ILL | 0 | 0 | 100 | 50 | 28 | 105 | 4-40 | Illite (CH-CL) |
| CON | 100 | 0 | 0 | NA | NA | NA | 4-40 | Concrete sand (SW) |
| OTT | 100 | 0 | 0 | NA | NA | NA | 4-40 | Fine sand (SP) |

Note:
†The values of SSA are calculated from the work by Mitchell (1993) and Or and Wraith (1999).

Additional data on variation of apparent dielectric constant, $K_a$ with temperature is provided in Table 4 below:

TABLE 4

Selected Physical Properties of Soils with Estimated PI Values

| Soil | sand (%) | silt (%) | clay (%) | Estimated PI† | SSA (m²/g) | Test range (° C.) | Comments |
|------|----------|----------|----------|---------------|------------|-------------------|----------|
| BSL | 23 | 60 | 17 | 33 | 125 | 5-65 | Brocko silt loam (Montmorillonitic clay fraction) |
| KLS | 86 | 11 | 3 | 4 | 17 | 5-65 | Kidman loamy sand |
| MSL | 29 | 55 | 16 | 19 | 73 | 5-65 | Millville silt loam (Kaolinitie + Montmorillonitic clay fraction) |
| RYO | 8 | 22 | 70 | 11 | 40 | 5-65 | Red-yellow Oxisol (Kaolinitie clay fraction) |

Note:
†The values of PI are calculated from the work by Mitchell (1993) and Or and Wraith (1999).

Atterberg Limits were not provided for these materials. Temperatures started at 5° C. and increased in 10° C. increments to 65° C. Values of both $K_a$ and bulk d.c. electrical conductivity, ECb were reported.

Figures 1, 2, 3, 3B:
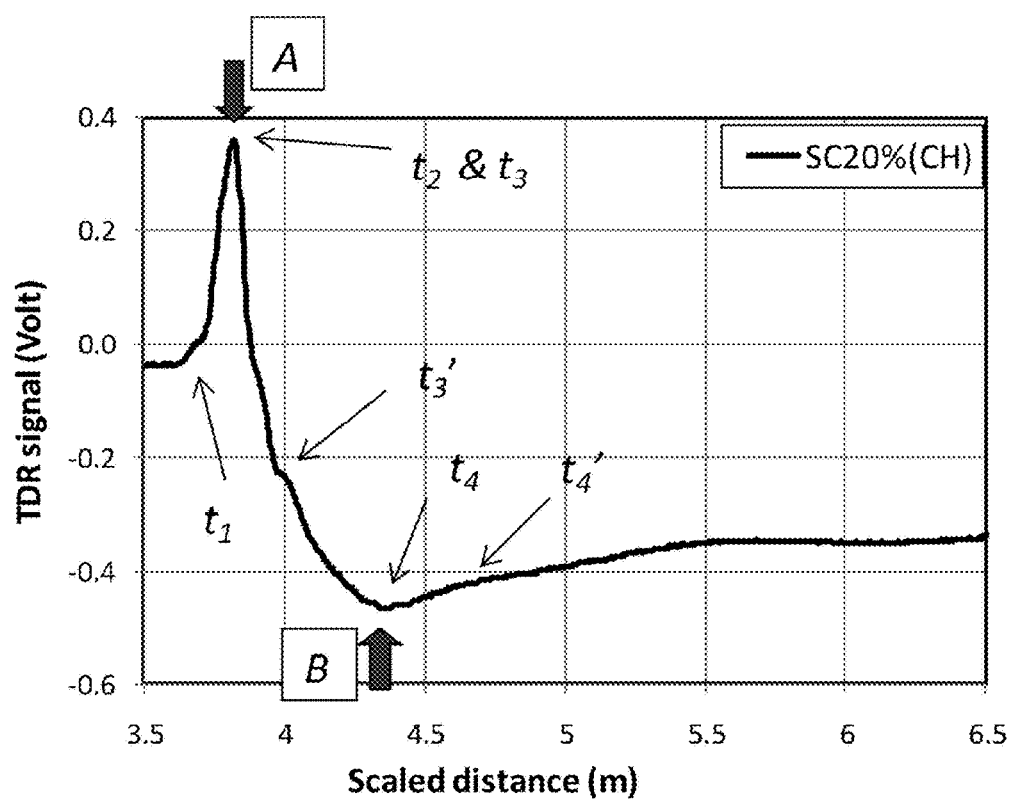
Figures 1, 2, 3, 3C:
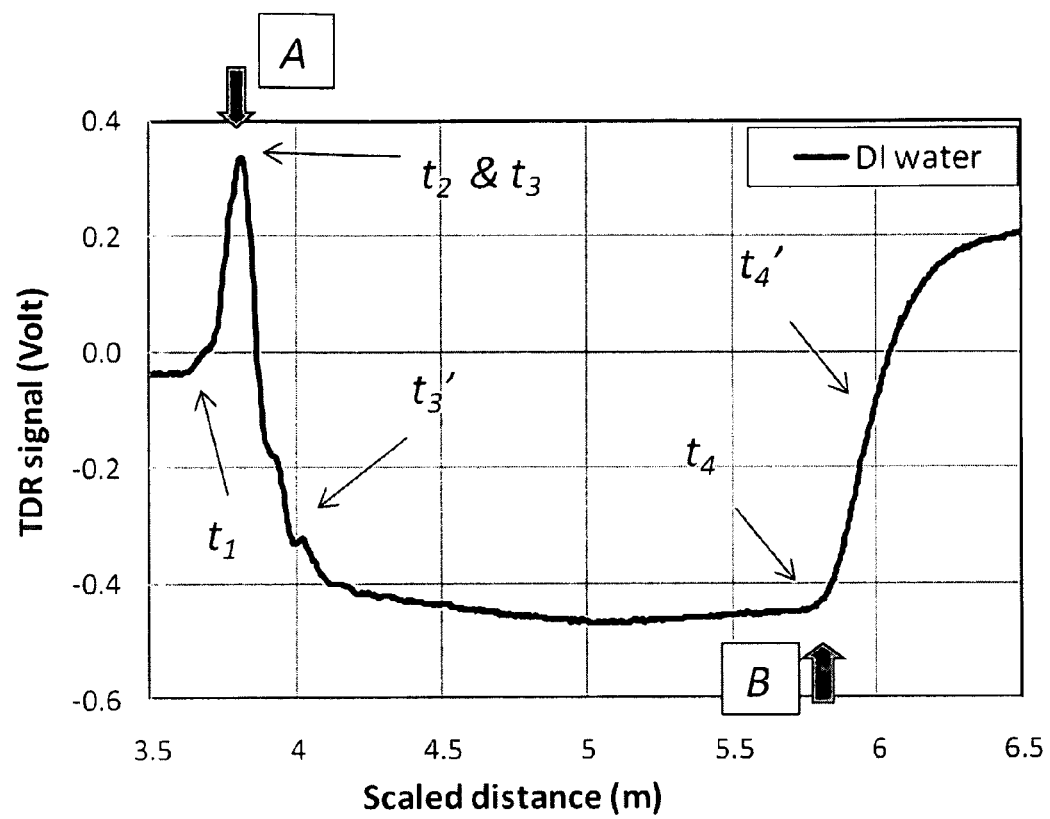

The apparent dielectric constant, $K_a$, is related to the wave propagation velocity of the electromagnetic wave in the soil probe. The velocity is dependent on the availability of polar molecules in the soil, which are commonly provided by water. While dry soil has very low values of $K_a$ in the range of 4 to 7 which are not sensitive to temperature, $K_a$ of water is temperature dependent. The values for temperature ranges of 4 to 45° C. can be described by the following linear function.

$$K_{aWater} = 87.8 - 0.366T \quad (3-3)$$

where T is temperature of water in ° C. To show the similarity, Eq. (3-3) and the one suggested by Weast (1986) are plotted in FIG. 3-3(a). Moreover, the temperature correction factor for $K_a$ in water ($TCF_{Ka\ Water}$) defined as the ratio of $K_a$ of water at 20° C. (room temperature) normalized by $K_a$ of water at T (° C.) is plotted in FIG. 3-3(b) using Eq. (3-3).

It is convenient that the measured values of $K_a$ of soil are corrected to 20° C. (room temperature) since the laboratory calibration tests for the use of Eqs. (1-1) and (1-9) are performed at room temperature. Thus, the temperature correction factor for $K_a$ of soil, $TCF_{Ka}$ is defined as:

$$TCF_{Ka} = \frac{K_{a,20}}{K_{a,T}} \quad (3-4)$$

Figures 1, 2, 3, 4:
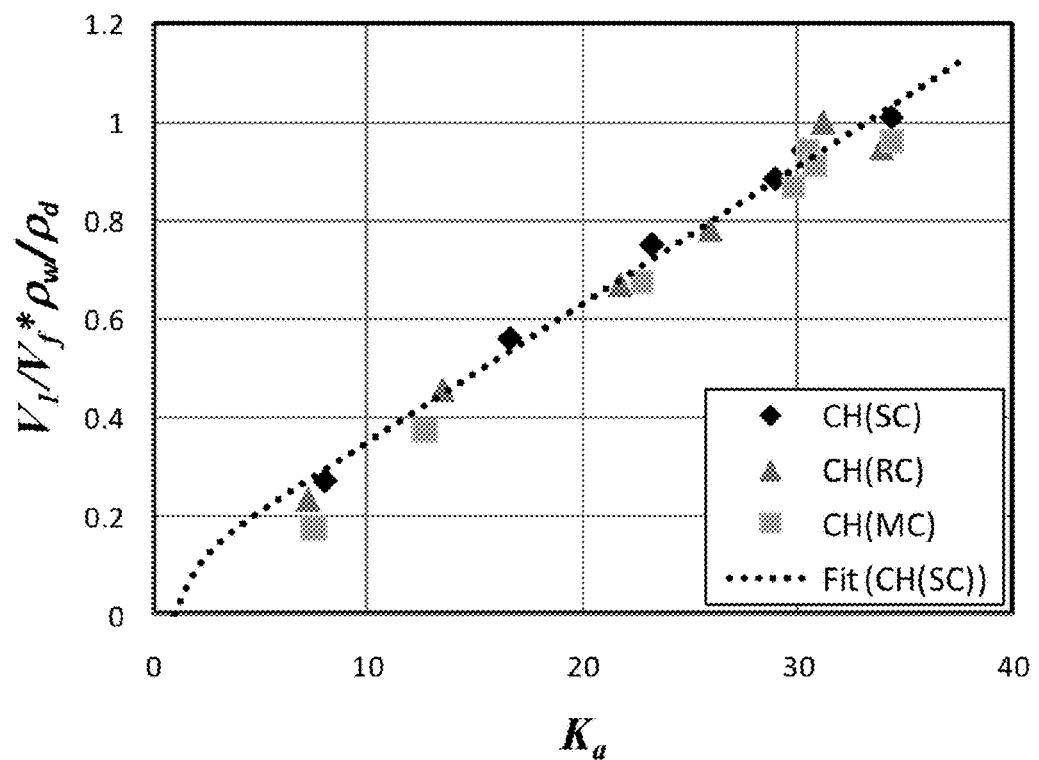

Data for cohesionless soils (CON, OTT, KLS) and cohesive soils (CRO, KAO, ILL, MSL, BSL, RYO) were analyzed and are presented in FIG. 3-4. The average of the data provides the simple linear relations as follows $$[TCF_{Ka}]_s = 0.97 + 0.0015T \quad (3-5)$$

$$[TCF_{Ka}]_c = 1.02 - 0.0010T \quad (3-6)$$

where subscript "s" and "c" denote cohesionless (or sandy) and cohesive (or clayey) soils, respectively. T is the measured temperature for a given test in ° C.

The dashed lines in FIG. 3-4 are the average of the data and represent Eqs. (3-5) and (3-6). Note that Eqs. (3-5) and (3-6) provide a reasonable approximation for the data and the magnitude of temperature corrections is very small in the temperature range from 4 to 40° C. Temperature corrections for $K_a$ would be less than 1% for tests in the range of 15 to 25° C., and these corrections may not be necessary for testing soil in this temperature range.

Cohesive soils contain clay minerals, even in relatively small amounts. The presence of the clay minerals affects the magnitude of $K_a$. Temperature corrections for $K_a$ on cohesive soils are opposite to those of water and those of cohesionless soils as described in FIGS. 3-3(b) and 3-4(a), respectively. This is due to the presence of bound water associated with clay minerals. There are two competing phenomena related to the two types of water: free water and bound water. In free water, the soil apparent dielectric constant $K_a$ decreases with an increase of temperature due to the water molecules for which rotation in the electromagnetic field is free. On the other hand, the bound water adsorbed onto the clay minerals is less mobile in the electromagnetic field, leading to smaller $K_a$ at a given temperature. As temperature increases, some of the bound water molecules are released from the clay minerals. These molecules are more mobile in the electromagnetic field, leading to the increase of $K_a$.

A process similar to that for obtaining temperature corrections for $K_a$ was used to obtain the temperature correction factors for $V_1$. The corresponding temperature correction factor to correct measured values of $V_1$ at a given temperature to those at 20° C. is defined as $$TCF_{V1} = \frac{V_{1,20}}{V_{1,T}} \tag{3-7}$$

Figures 1, 2, 3, 4, 5:
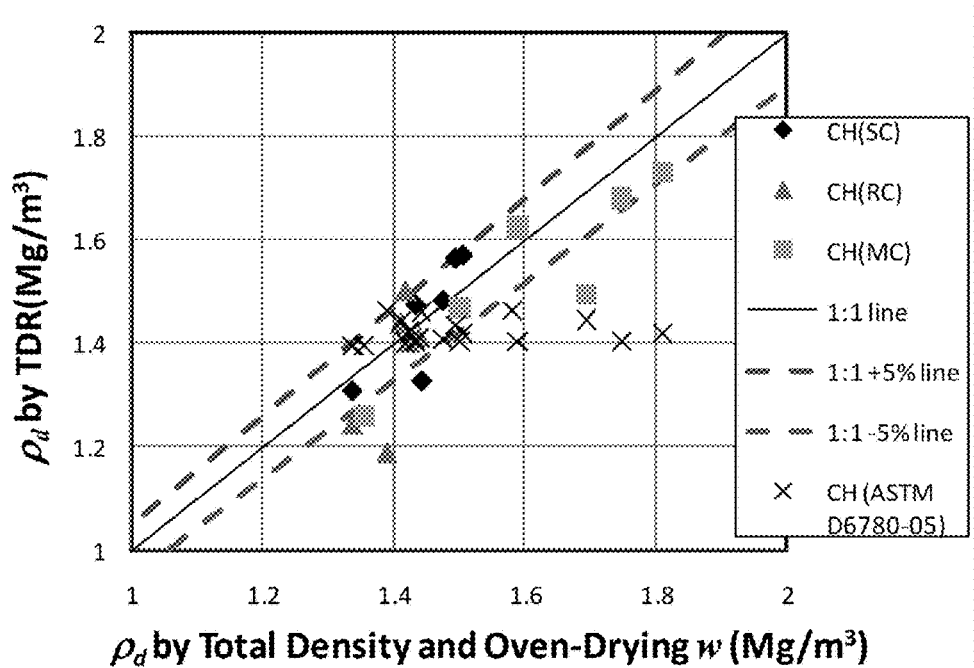
Figures 1, 2, 3, 4, 5, 6:
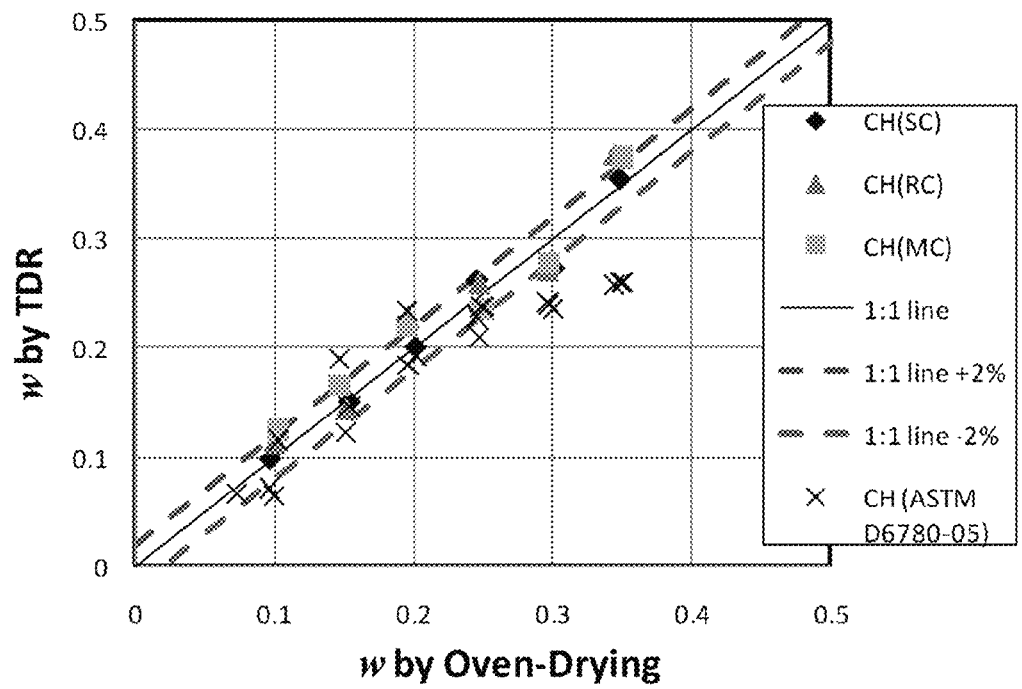
Figures 1, 2, 3, 4, 5, 6, 7:
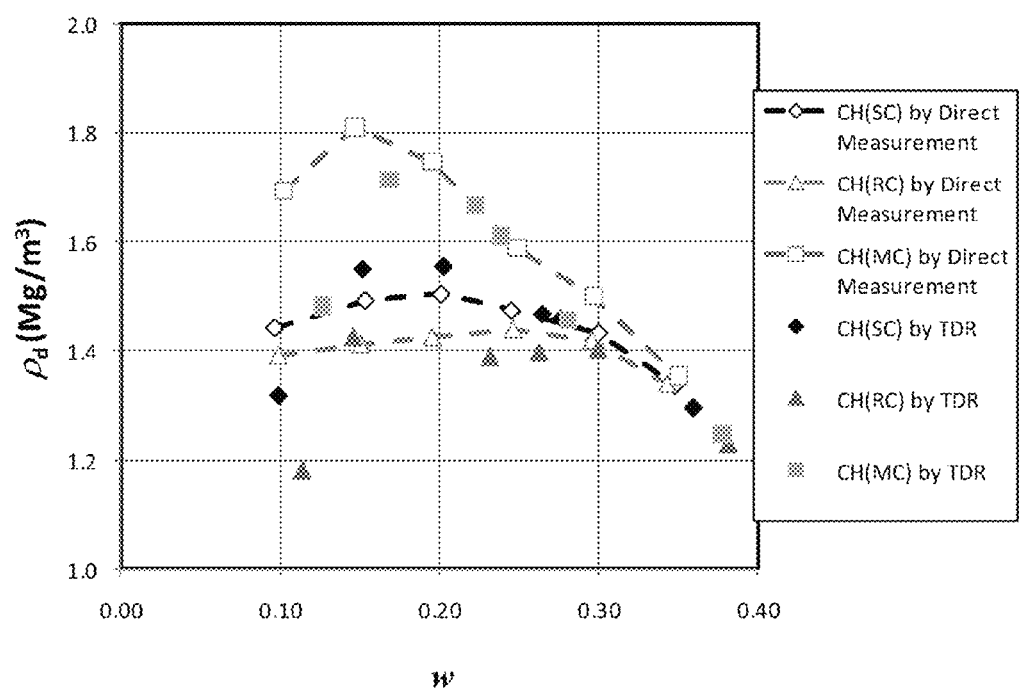
Figures 1, 2, 3, 4, 5, 6, 7, 8:
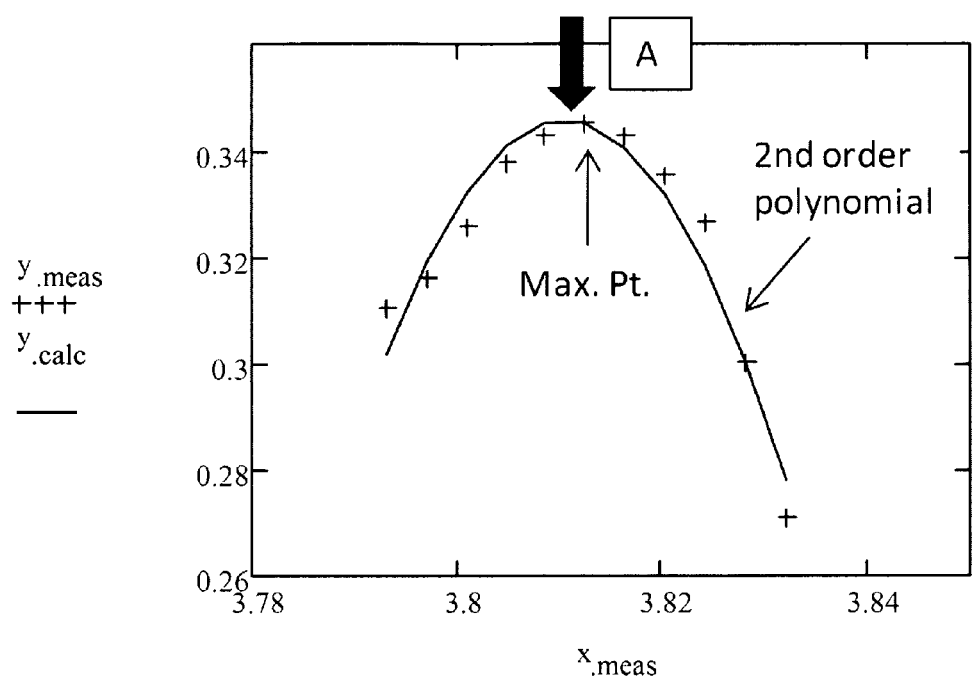
Figures 1, 2, 3, 4, 5, 6, 7, 8, 9:
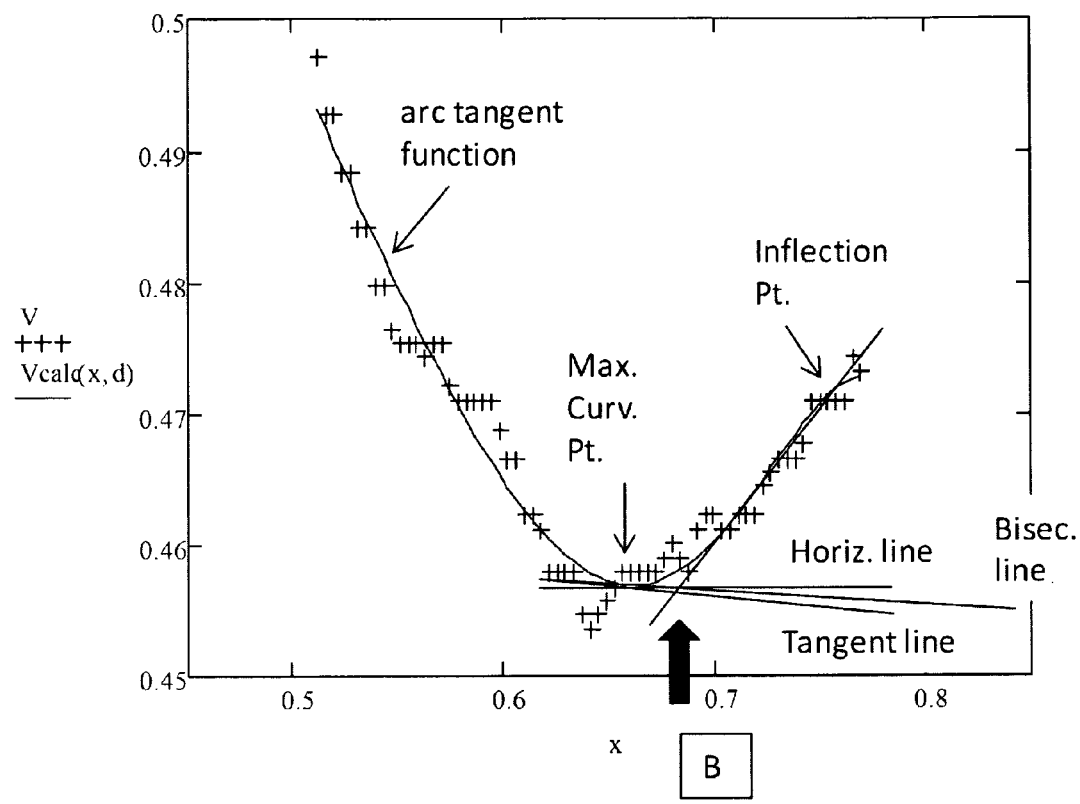
Figures 1, 2, 3, 4, 5, 6, 7, 8, 9, 10:
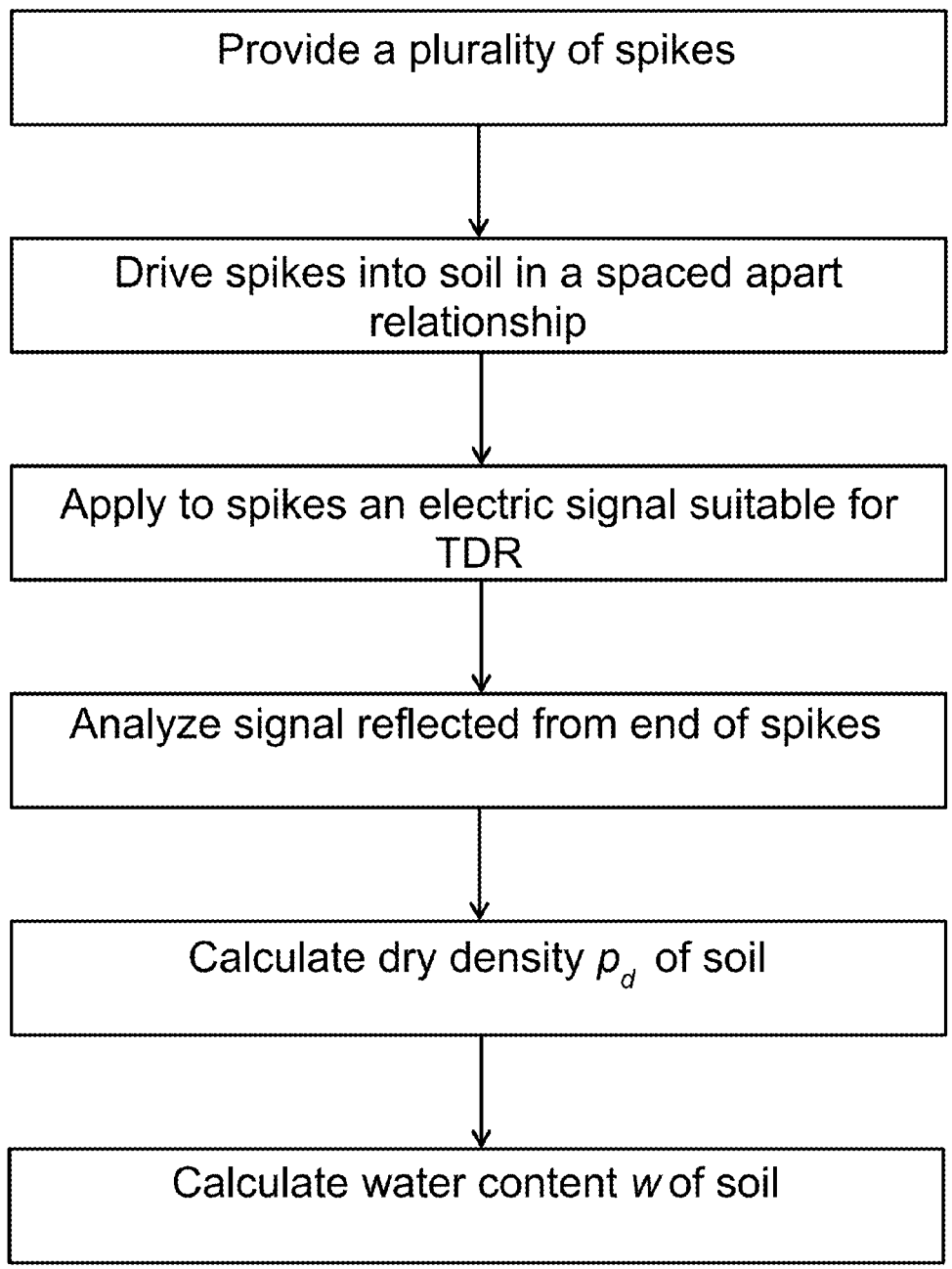

The average of the data presented in FIG. 3-5 provides the temperature correction factors for V1 on cohesionless soils (Eq. (3-8)) and cohesive soils (Eq. (3-9)).

$$[TCF_{V1}]_s = 0.92 + 0.0040T \tag{3-8}$$

$$[TCF_{V1}]_c = 1.06 - 0.0030T \tag{3-9}$$

where subscript "s" and "c" denote cohesionless (or sandy) and cohesive (or clayey) soils, respectively. T is the measured temperature for a given test in ° C.

Note that the corrections given in Eqs. (3-8) and (3-9) are small, but are slightly larger than the corrections for $K_a$ in magnitude and have the same sense, i.e. for cohesionless soils, an increase in temperature causes an increase in $TCF_{V1}$ and vice versa for cohesive soils.

The value of $V_f$, the voltage of the TDR signal after wave propagation has ceased, is the primary determinant of the bulk d.c. electrical conductivity, $EC_b$, of soil. The effects of temperature on the measured electrical conductivity and the relations to correct the electrical conductivity for changes in temperature are relatively independent of soil texture, unlike the ones for the apparent dielectric constant.

The temperature correction factor for $V_f$ of soil, $TCF_{Vf}$ is determined from the temperature correction factor associated with $EC_b$ that may be determined from $$EC_b = \frac{1}{C}\left(\frac{2V_{in}}{V_f} - 1\right) \tag{3-10}$$

where C is a constant that depends on probe geometry and the impedance of the TDR tester. $V_{in}$ and $V_f$ are the measured input and final voltage, respectively. The temperature correction factors for $EC_b$ and $V_f$ of soil are defined as $$TCF_{ECb} = \frac{EC_{b,20}}{EC_{b,T}} \tag{3-11}$$

$$TCF_{Vf} = \frac{V_{f,20}}{V_{f,T}} \tag{3-12}$$

Substituting Eq. (3-10) into Eq. (3-11) and solving for $V_{f,20}/V_{f,T}$ yields $$TCF_{Vf} = \frac{2}{\frac{V_{f,T}}{V_{in}}(1 - TCF_{ECb}) + 2TCF_{ECb}} \tag{3-13}$$

where $TCF_{ECb}$ can be described by $$TCF_{ECb} = 2.04 - 0.347 \ln(T) \tag{3-14}$$

which holds for both cohesionless and cohesive soils, shown in FIG. 3-6. Note that the temperature correction factor for $V_f$ in Eq. (13) is a function of the value of $V_f$ divided by the input voltage, $V_{in}$.

FIG. 3-6(b) shows that the data for dry soils were not included to obtain Eq. (3-14) since $EC_b$ for dry soils are relatively independent of temperature variations. Although the variations of $TCF_{ECb}$ at low temperature (4 to 5° C.) exist, it is attributed to the fact that the values of $EC_b$ at low temperature for these soils are small and this may lead to large variation of $TCF_{ECb}$ due to the definition of $TCF_{ECb}$ (Eq. (3-11)). FIGS. 3-6(a) and 6(b) also show that temperature corrections would provide a better approximation for the data for tests in the range of 15 to 25° C.

It may be convenient to provide the temperature correction factors for $V_1/V_f$ in order to apply those to Eq. (1-9) directly. The temperature correction factor to correct measured values of $V_1/V_f$ at a given temperature to those at 20° C. is defined as $$TCF_{V1/Vf} = \frac{TCF_{V1/Vf,20}}{TCF_{V1/Vf,T}} = \frac{TCF_{V1}}{TCF_{Vf}} \tag{3-15}$$

For cohesionless soils, the temperature correction factor is obtained by combining Eqs. (3-8), (3-13), and (3-14) to give $$[TCF_{V1/Vf}]_1 = \tag{3-16}$$
$$(0.46 + 0.0020T)\left[\frac{V_{f,T}}{V_{in}}(0.35\ln(T) - 1.04) + 4.08 - 0.70\ln(T)\right]$$

For cohesive soils, the temperature correction factor is obtained by combining Eqs. (3-9), (3-13), and (3-14) to give $$[TCF_{V1/Vf}]_0 = \tag{3-17}$$
$$(0.53 + 0.0015T)\left[\frac{V_{f,T}}{V_{in}}(0.35\ln(T) - 1.04) + 4.08 - 0.70\ln(T)\right]$$

Values of $TCF_{V1/Vf}$ for cohesionless and cohesive soils calculated by Eqs. (3-16) and (3-17) are given in FIGS. 3-7(a) and 3-7(b), respectively, for possible values of $Vf_1 V_{in}$ which range from zero for highly conductive soils to two for non-conductive soils.

The temperature correction factors for $V_1/V_f$ may have greater values than those for either $K_a$ or $V_1$, and the values of $V_1/V_f$ can be adjusted for temperature. Note that the temperature correction factor for $V_1/V_f$ on cohesive soils has slightly greater values than the one for cohesionless soils.

Naturally occurring soils are mixtures of soil solids, water, and air. $K_a$ of soil solids in the range of 4 to 7 is not sensitive to temperature and $K_a$ of air is 1. Since soil is not composed totally of water and $K_a$ of water is approximately 80 at room temperature, $K_a$ of the mixture would be less than $K_a$ of water and the behavior of the mixture with temperature also would be different from water.

A simple dielectric mixing model for cohesionless soil is expressed as $$(K_a(T))^\alpha = (K_{aSolids})^\alpha(1-n) + (K_{aWater}(T))^\alpha \cdot \theta + (K_{aAir})^\alpha(n-\theta) \tag{3-18}$$

where $K_{aSolids}$, $K_{aWater}$, $K_{aAir}$ are the dielectric constant of soil solids, water, and air. n is the porosity of soil and expressed as $$\left(1 - \frac{\rho_d}{G_s\rho_w}\right),$$

θ is the volumetric water content and expressed as $$\left(w\frac{\rho_d}{\rho_w}\right),$$

and $G_s$ is the specific gravity of soil solids. α is a parameter that reflects the geometry of the media with respect to the applied electromagnetic field, with $-1<\alpha<1$. α should be experimentally determined. The calculated results of Eq. (3-18) for the data on CON, OTT, KLS soils are compared with the measured data in FIGS. 3-8(a)-3-8(c), with α=0.5, $K_{aSolids}$=5, $K_{aAir}$=1, and $K_{aWater}$ given by Eq. (3-3). The results show good agreements for the calculated and measured data.

The temperature effects for cohesive soils are complicated by the presence of bound water associated with clay minerals. The three-phase dielectric mixing model described in Eq. (3-18) is not adequate for soils containing clays; thus a four-phase model is.

A dielectric mixing model for cohesive soils is expressed as $$(K_a(T))^\beta=(K_{aSolids})^\beta(1-n)+(K_{aAir})^\beta(n-\theta_{FW}(T)-\theta_{BW}(T))+(K_{aFW}(T))^\beta\cdot\theta_{FW}(T)+(K_{aFW}(T))^\beta\theta_{BW}(T) \quad (3\text{-}19)$$

where $K_{aBW}$ and $K_{aFW}$ are the dielectric constant of the bound water and free water, respectively. β is similar to α in Eq. (3-18) and should be experimentally determined, with $-1<\beta<1$. For wet soil, β is close to 0.5 but unknown, and becomes a fitting parameter. $\theta_{Fw}$ is the volume fraction of the free water and expressed as $\theta-\theta_{BW}$. $\theta_{BW}$ is the volume fraction of the bound water and temperature dependent. A simplified form of $\theta_{BW}(T)$ as follows $$\theta_{BW}(T)=x(T)A_s\rho_d \quad (3\text{-}20)$$

where $A_s$ is the specific surface area [m²/kg] and $x(T)$ is expressed as $$x(T) = \frac{a}{-d+T\cdot\ln\left(\frac{k}{8\pi^2 r^3 cf^*}T\right)} \quad (3\text{-}21)$$

where a is a constant modified from the water viscosity profiles of Low (1976) and expressed as 1621 [A K]. k is the Boltzmann constant, which equals to $1.38066\times10^{-23}$ [J/K], and r is the radius of a water molecule, r≈1.8-2.5 [A]. c and d are determined from expressing the temperature dependency of the viscosity of water, c equals to $9.5\times10^{-7}$ [Pa·s], and d equals to 2047 [K]. f* is the cutoff frequency range providing a conservative estimate for wet soils and f*≈0.8-1.0 [GHz].

The calculated results of Eqs. (3-19)-(3-21) for the data on CRO, MSL, BSL and RYO soils are compared with the measured data in FIGS. 3-8(d)-3-8(f), with β=0.2, r=2.4 [A], f*=1.0 [GHz], $K_{aSolids}$=5, and $K_{aAir}$=1. The results generally show good agreements between the calculated and measured data, however, for high water contents and temperature higher than 25° C., $TCF_{Ka}$ from the mixing model tends to over-predict temperature corrections compared to the measured data. The use of the four-phase models confirms the observed trends and uses on estimating the volumetric bound water content and properties of that bound water.

Eqs. (3-5) and (3-16) can be used for adjusting temperature effects of cohesionless soils while Eqs. (3-6) and (3-17) for cohesive soils. An automatic method to detect cohesionless or cohesive soil in the field test may be of value. From plots of measured values of $V_1/V_f$ versus $K_a$ for variety of soils, the data for each soil type are presented in FIG. 3-9(a) and a line with slope=0.025 appears to delineate cohesionless and cohesive soils, as shown in FIG. 3-9(b).

Preliminary criteria for selection of the temperature correction equations based on data measured at the time of the test become as follows $$[TCF_{Ka}]_s, [TCF_{V1/Vf}]_s \text{ if } \frac{V_1/V_f}{K_a} \leq 0.025 \quad (3\text{-}22)$$

$$[TCF_{Ka}]_c, [TCF_{V1/Vf}]_c \text{ if } \frac{V_1/V_f}{K_a} > 0.025$$

where $[TCF_{Ka}]_s$ and $[TCF_{V1/Vf}]_s$ are defined by Eqs. (3-5) and (3-16), $[TCF_{Ka}]_c$ and $[TCF_{V1/Vf}]_c$ are defined by Eqs. (3-6) and (3-17), respectively. For situations where Eq. (3-22) is used to identify the temperature correction factors, the TDR parameters should be adjusted for temperature beforehand. Note that Eq. (3-22) may be limited to tap water, since the electrical conductivity of the pore fluid can affect the magnitude of $V_1$ and $V_f$; additional study of this is warranted.

Temperature corrections are relatively small for the apparent dielectric constant, $K_a$, and generally do not need to be made for temperatures between 15 and 25° C. as can be seen from the coefficients in Eq. (3-5) for cohesionless soils and Eq. (3-6) for cohesive soils. Hence, TDR-measured $K_a$ in Eq. (1-1) is not very sensitive to temperature. For the second calibration equation (Eq. (1-9)), TDR-measured $V_1/V_f$ is very sensitive to temperature. An example of the importance for correcting data for temperature effects in Eq. (1-9) is given in FIG. 3-10, which is a plot of Eq. (1-9) for data measured at temperatures from 4 to 40° C. on CRO soil for a range of water contents from below optimum to above optimum. Eq. (1-9) represents a good fit between $K_a$ and density-normalized voltage ratio $$\frac{V_1}{V_f}\frac{\rho_w}{\rho_d}$$

but FIG. 3-10(a) showed that temperature has a strong influence on the data. The coefficients in Eq. (1-9) would have different values depending on temperature. Applying Eq. (3-6) to correct the values of $K_a$ and Eq. (3-17) to correct the values of $V_1/V_f$ provides the temperature corrected data as shown in FIG. 3-10(b). Note that data from different temperatures, when adjusted for temperature, clusters about the line determined for the test data at 20° C.

FIGS. 3-11(a) and 3-11(b) represent TDR measured values (by Eqs. (1-1) and (1-9)) plotted versus reference values determined by ASTM D2216 (ASTM 2010b) for water content and determined by direct measurement and water content for dry density results, respectively. The TDR determined water content and dry density were obtained with calibration coefficients (a, b, $c_1$, $d_1$, $f_1$) with data points at 20° C. after the temperature correction factors were applied to TDR-measured $K_a$ and $V_1/V_f$ as obtained from each TDR test. The results of water content (FIG. 3-11(a)) generally lie within the 1:1 line ±2% point of water content, and those of dry density (FIG. 3-11(b)) lie within the 1:1 line ±5% (of measured value).

All publications, prior patents and applications, and other documents cited herein are hereby incorporated by reference in their entirety as if each had been individually incorporated by reference and fully set forth. While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A method for measuring a property of soil, comprising:
providing a plurality of spikes adapted to be driven into the soil;
driving said plurality of spikes into the soil in spaced relationship;
applying to said plurality of spikes an electrical signal suitable for time domain reflectometry;
analyzing a reflected signal corresponding to the applied signal using time domain reflectometry to measure a voltage drop $V_1$;
calculating dry density $\rho_d$ of the soil using a predetermined relationship between $V_1$ and $\rho_d$; and
calculating gravimetric water content w of the soil using a predetermined relationship between $\rho_d$, and w;
wherein voltage drop $V_1$ indicates the drop in voltage between the signal reflected from a surface of the soil and the signal reflected from an end of the spikes.

2. The method of claim 1, wherein the soil has a surface and the plurality of spikes have a lower end, and wherein said analyzing a reflected signal includes measuring the apparent distance between a signal reflected from the soil and a signal reflected from the lower end of said plurality of spikes to determine an apparent length $L_a$.

3. The method of claim 2, wherein said plurality of spikes have a probe length $L_p$ and an apparent dielectric constant $K_a$ is determined as $K_a = (L_a/L_p)^2$.

4. The method of claim 1, wherein said plurality of spikes have a probe length $L_p$ and an apparent dielectric constant $K_a$ is determined as $$K_a = \left(\frac{B-A}{L_p}\right)^2$$

where B and A are the first and second reflection points of the reflected signal.

5. The method of claim 1, wherein analyzing a reflected signal includes determining an apparent dielectric constant $K_a$ of the soil and measuring a long term voltage $V_f$ of the reflected signal.

6. The method of claim 5, wherein the predetermined relationship between $V_1$ and $\rho_d$ is $$\rho_d = \frac{\frac{V_1}{V_f}\rho_w}{c_1 + d_1(K_a - 1) - c_1 \cdot \exp[-f_1(K_a - 1)]}$$

where $c_1$, $d_1$, and $f_1$ are soil specific calibration constants, and $\rho_w$ is the density water.

7. The method of claim 6, wherein the calibration constants are $c_1$, $d_1$, and $f_1$ are predetermined experimentally for a given soil using the relationship $$\frac{V_1}{V_f}\frac{\rho_w}{\rho_d} = c_1 + d_1(K_a - 1) - c_1 \cdot \exp[-f_1(K_a - 1)].$$

8. The method of claim 5, wherein the predetermined relationship between $\rho_d$, and w is $$w = \frac{1}{b}\left(\sqrt{K_a}\frac{\rho_w}{\rho_d} - a\right)$$

where a and b are soil specific calibration constants, and $\rho_w$ is the density of water.

9. The method of claim 8, wherein the calibration constants a and b are predetermined experimentally for a given soil using the relationship $$\sqrt{K_a}\frac{\rho_w}{\rho_d} = a + b \cdot w.$$

10. The method of claim 5, wherein the value of $K_a$ at a given temperature T is adjusted to a value $K_{a,20° C.}$ at a standard temperature of 20° C., where $$K_{a,20° C.} = K_{a,T} * TCF_{Ka}$$

and where $TCF_{Ka}$ = Temperature Compensation Function for $K_a$

= $0.97 + 0.0015T$ for cohesionless soils,

= $1.02 - 0.0010T$ for cohesive soils, and where $4°$ C.$\leq T \leq 40°$ C.

11. The method of claim 1, wherein the value of $V_1$ at a given temperature T is adjusted to a value $V_{1,20° C.}$ at a standard temperature of 20° C., where $$V_{1,20° C.} = V_{1,T} * TCF_{V1}$$

and where $TCF_{V1}$ = Temperature Compensation Function for $V_1$

= $0.92 + 0.0040T$ for cohesionless soils,

= $1.06 - 0.0030T$ for cohesive soils, and where $4°$ C.$\leq T \leq 40°$ C.

12. The method of claim 5, wherein the value of $V_f$ at a given temperature T is adjusted to a value $V_{f,20° C.}$ at a standard temperature of 20° C., where $$V_{f,20° C.} = V_{f,T} * TCF_{Vf}$$

and where
$TCF_{Vf}$ = Temperature Compensation Function for $V_f$ $$TCF_{Vf} \frac{2}{\frac{V_{f,T}}{V_{in}}(1 - TCF_{ECb}) + 2TCF_{ECb}}$$

and where $TCF_{Ecb} = 2.04 - 0.347 \ln(T)$.

13. A method for measuring a property of soil, comprising:
   providing a plurality of spikes adapted to be driven into the soil;
   driving said plurality of spikes into the soil in spaced relationship;
   applying to said plurality of spikes an electrical signal suitable for time domain reflectometry;
   analyzing a reflected signal corresponding to the applied signal using time domain reflectometry, including determining an apparent dielectric constant $K_a$ of the soil, measuring a long term voltage $V_f$ of the reflected signal, and measuring a voltage drop $V_1$ from reflection of the applied signal;
   adjusting the values of $K_a$, $V_f$, and $V_1$ using predetermined temperature compensation functions; and
   calculating dry density $\rho_d$ of the soil using a predetermined relationship between $K_a$, $V_f$, $V_1$, and $\rho_d$;
   wherein voltage drop $V_1$ indicates the drop in voltage between the signal reflected from a surface of the soil and the signal reflected from an end of said spikes.

14. The method of claim 13, wherein the predetermined relationship between $K_a$, $V_f$, $V_1$, and $\rho_d$ is $$\rho_d = \frac{\frac{V_1}{V_f}\rho_w}{c_1 + d_1(K_a - 1) - c_1 \cdot \exp[-f_1(K_a - 1)]}$$

where $c_1$, $d_1$, and $f_1$ are soil specific calibration constants, and $\rho_w$ is the density water.

15. The method of claim 14, wherein the calibration constants are $c_1$, $d_1$, and $f_1$ are predetermined experimentally for a given soil using the relationship $$\frac{V_1}{V_f}\frac{\rho_w}{\rho_d} = c_1 + d_1(K_a - 1) - c_1 \cdot \exp[-f_1(K_a - 1)].$$

16. An apparatus for measuring a property of soil, comprising:
   a plurality of spikes adapted to be driven into the soil;
   means for applying to said plurality of spikes an electrical signal suitable for time domain reflectometry;
   means for analyzing a reflected signal corresponding to the applied signal using time domain reflectometry to measure a voltage drop $V_1$ from reflection of the applied signal;
   means for calculating dry density $\rho_d$ of the soil using a predetermined relationship between $V_1$ and $\rho_d$; and
   means for calculating gravimetric water content w of the soil using a predetermined relationship between $\rho_d$, and w;
   wherein voltage drop $V_1$ indicates the drop in voltage between the signal reflected from a surface of the soil and the signal reflected from an end of the spikes.

17. The apparatus of claim 16 further comprising means for analyzing a reflected signal using time domain reflectometry to determine an apparent dielectric constant $K_a$ of the soil and measure a long term voltage $V_f$ of the reflected signal.

18. The apparatus of claim 17, wherein the predetermined relationship between $V_1$ and $\rho_d$ is $$\rho_d = \frac{\frac{V_1}{V_f}\rho_w}{c_1 + d_1(K_a - 1) - c_1 \cdot \exp[-f_1(K_a - 1)]}$$

where $c_1$, $d_1$, and $f_1$ are soil specific calibration constants, and $\rho_w$ is the density water.

19. The apparatus of claim 18, wherein the calibration constants are $c_1$, $d_1$, and $f_1$ are predetermined experimentally for a given soil using the relationship $$\frac{V_1}{V_f}\frac{\rho_w}{\rho_d} = c_1 + d_1(K_a - 1) - c_1 \cdot \exp[-f_1(K_a - 1)].$$

20. The apparatus of claim 17, wherein the predetermined relationship between $\rho_d$ and w is $$w = \frac{1}{b}\left(\sqrt{K_a}\frac{\rho_w}{\rho_d} - a\right)$$

where a and b are soil specific calibration constants, and $\rho_w$ is the density of water.

21. The apparatus of claim 20, wherein the calibration constants a and b are predetermined experimentally for a given soil using the relationship $$\sqrt{K_a}\frac{\rho_w}{\rho_d} = a + b \cdot w.$$

22. The apparatus of claim 16, wherein said means for analyzing the reflected signal, said means for calculating dry density $\rho_d$, and said means for calculating gravimetric water content w are a computer.

23. The method of claim 1, wherein the soil has a surface and the plurality of spikes have a lower end, and wherein said analyzing a reflected signal includes measuring a drop in voltage between a signal reflected from the soil surface and a signal reflected from the lower end of said plurality of spikes to determine voltage drop $V_1$.

24. The method of claim 13, wherein the soil has a surface and the plurality of spikes have a lower end, and wherein said analyzing a reflected signal includes measuring a drop in voltage between a signal reflected from the soil surface and a signal reflected from the lower end of said plurality of spikes to determine voltage drop $V_1$.

25. The apparatus of claim 16, wherein the soil has a surface and the plurality of spikes have a lower end, and wherein said means for analyzing a reflected signal includes means for measuring a drop in voltage between a signal reflected from the soil surface and a signal reflected from the lower end of said plurality of spikes to determine voltage drop $V_1$.

* * * * *